US009745576B2

(12) United States Patent
de Visser et al.

(10) Patent No.: US 9,745,576 B2
(45) Date of Patent: Aug. 29, 2017

(54) RNA MODULATING OLIGONUCLEOTIDES WITH IMPROVED CHARACTERISTICS FOR THE TREATMENT OF NEUROMUSCULAR DISORDERS

(71) Applicant: Prosensa Technologies B.V., Leiden (NL)

(72) Inventors: Peter Christian de Visser, Leiden (NL); Susan Allegonda Maria Mulders, Groesbeek (NL)

(73) Assignee: BIOMARIN TECHNOLOGIES B.V., Leiden (NL)

(*) Notice: Subject to any disclaimer, the term of this patent is extended or adjusted under 35 U.S.C. 154(b) by 0 days.

(21) Appl. No.: 14/522,002

(22) Filed: Oct. 23, 2014

(65) Prior Publication Data

US 2015/0148404 A1 May 28, 2015

Related U.S. Application Data

(63) Continuation of application No. PCT/NL2013/050306, filed on Apr. 23, 2013.

(60) Provisional application No. 61/636,914, filed on Apr. 23, 2012.

(30) Foreign Application Priority Data

Apr. 23, 2012 (EP) .................................... 12165139

(51) Int. Cl.
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/333* (2013.01); *C12N 2310/334* (2013.01); *C12N 2310/335* (2013.01); *C12N 2310/336* (2013.01); *C12N 2310/3341* (2013.01); *C12N 2310/346* (2013.01); *C12N 2310/3521* (2013.01); *C12N 2320/34* (2013.01)

(58) Field of Classification Search
None
See application file for complete search history.

(56) References Cited

U.S. PATENT DOCUMENTS

| | | | |
|---|---|---|---|
| 7,514,551 B2 | 4/2009 | Rabbani et al. | |
| 7,655,785 B1 | 2/2010 | Bentwich | |
| 9,057,066 B2 | 6/2015 | Hung et al. | |
| 2003/0109476 A1 | 6/2003 | Kmiec et al. | |
| 2005/0277133 A1 | 12/2005 | McSwiggen | |
| 2006/0074034 A1 | 4/2006 | Collins et al. | |
| 2007/0299027 A1 | 12/2007 | Hung et al. | |
| 2008/0015158 A1 | 1/2008 | Ichiro et al. | |
| 2011/0184050 A1* | 7/2011 | De Kimpe ........... | C12N 15/113 514/44 R |

FOREIGN PATENT DOCUMENTS

| | | | | |
|---|---|---|---|---|
| CN | 101501193 A | 8/2009 | | |
| WO | WO-9428175 A1 | 12/1994 | | |
| WO | WO-9530774 A1 | 11/1995 | | |
| WO | WO 03/004511 | 1/2003 | ............. | C07H 21/00 |
| WO | WO-03013437 A2 | 2/2003 | | |
| WO | WO-2006031267 A2 | 3/2006 | | |
| WO | WO-2006083800 A2 | 8/2006 | | |
| WO | WO-2007044362 A2 | 4/2007 | | |
| WO | WO 2008/018795 | 2/2008 | ............. | C12N 15/11 |
| WO | WO-2009008727 A2 | 1/2009 | | |
| WO | WO 2009/099326 | 8/2009 | ............. | A61K 48/00 |
| WO | WO-2010006237 A2 | 1/2010 | | |
| WO | WO-2010014592 A1 | 2/2010 | | |
| WO | WO-2010144485 A1 | 12/2010 | | |
| WO | WO 2011/097614 | 8/2011 | ............. | C07H 21/00 |
| WO | WO 2011/097641 | 8/2011 | ............. | C07H 21/04 |
| WO | WO-2012012443 A2 | 1/2012 | | |
| WO | WO-2012021985 A1 | 2/2012 | | |
| WO | WO-2012109395 A1 | 8/2012 | | |
| WO | WO-2012150960 A1 | 11/2012 | | |
| WO | WO-2013082548 A1 | 6/2013 | | |
| WO | WO-2013120003 A1 | 8/2013 | | |

OTHER PUBLICATIONS

Evers, et al., "Targeting Several CAG Expansion Diseases by a Single Antisense Oligonucleotide," *PLOS One*, vol. 6, No. 9, Sep. 1, 2011, pp. 1-11.
Gagnon, et al., "Allele-Selective Inhibition of Mutant *Huntingtin* Expression with Antisense Oligonucleotides Targeting the Expanded CAG Repeat," *Biochemistry*, vol. 49, No. 47, Oct. 28, 2010, pp. 10166-10178.
Fiszer, et al., "An Evaluation on Oligonucleotide-Based Therapeutic Strategies for PolyQ Diseases," *BMC Molecular Biology*, vol. 13, No. 1, Mar. 7, 2012, whole article.
Lee, et al., "RNase H-Mediated Degradation of Toxic RNA in Myotonic Dystrophy Type 1," *Proceedings of the National Academy of Sciences*, Feb. 27, 2012, whole document.
Magaña, et al., "Perspectives on Gene Therapy in Myotonic Dystrophy Type 1," *Journal of Neuroscience Research*, vol. 89, No. 3, Dec. 16, 2011, pp. 275-285.
Mulders, et al., "Triplet-Repeat Oligonucleotide-Mediated Reversal of RNA Toxicity in Myotonic Dystrophy" *Proceedings of the National Academy of Sciences*, vol. 106, No. 33, Aug. 18, 2009, pp. 13915-13920.
Mulders, et al., "Molecular Therapy in Myotonic Dystropy: Focus on RNA Gain-of Function," *Human Molecular Genetics*, vol. 19, No. R1, Apr. 20, 2010, pp. R90-R97.
Muntoni, et al., "Targeting RNA to Treat Neuromuscular Disease," *Nature Reviews Drug Discovery*, vol. 10, No. 8, Jan. 1, 2011, pp. 621-637.

(Continued)

*Primary Examiner* — Tracy Vivlemore
(74) *Attorney, Agent, or Firm* — Sunstein Kann Murphy & Timbers LLP

(57) ABSTRACT

The current invention provides an improved oligonucleotide and its use for treating, ameliorating, preventing, delaying and/or treating a human cis-element repeat instability associated genetic neuromuscular or neurodegenerative disorder.

6 Claims, 2 Drawing Sheets

(56) References Cited

OTHER PUBLICATIONS

Figure 1A:
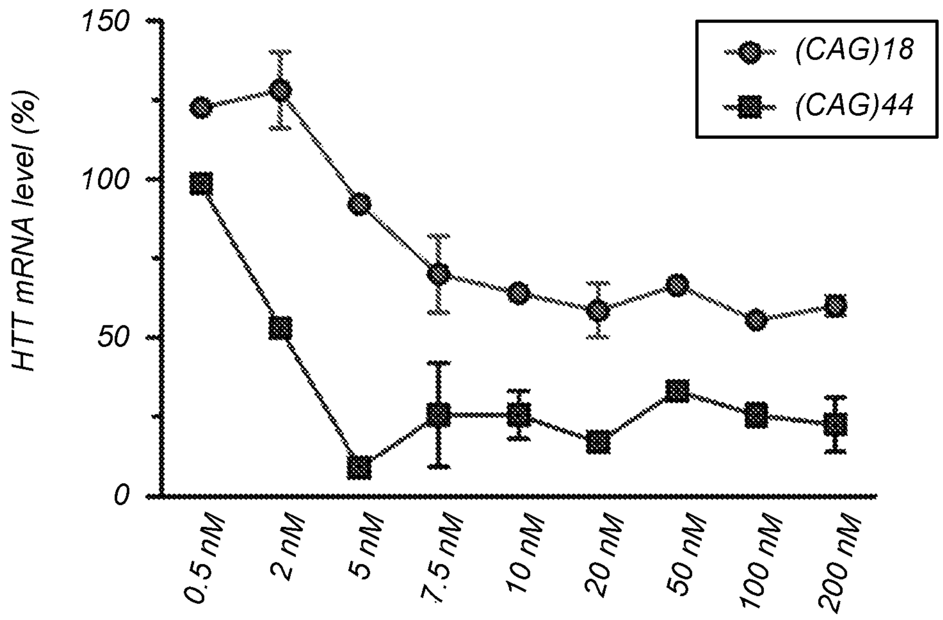

Sah, et al., "Oligonucleotide Therapeutic Approaches for Huntington Disease," *Journal of Clinical Investigation*, vol. 121, No. 2, Feb. 1, 2011, pp. 500-507.
Authorized Officer: Bucka, Alexander, International Search Report, PCT/NL2013/050306, Jul. 19, 2013, 6 pages.
ATDBIO, Ltd., "DNA Duplex Stability," http://www.atdbio.com/content/53/DNA-duplex-stability, 10 pages, 2008.
Bonifazi, E., et al., "Use of RNA Fluorescence In Situ Hybridization in the Prenatal Molecular Diagnosis of Myotonic Dystrophy Type I," Clinical Chemistry, vol. 52 (2), pp. 319-322, 2006.
Buczko, W., et al., "Modulation of Plasminogen Activator Inhibitor Type-1 Biosynthesis in Vitro and in Vivo with Oligo(nucleoside phosphorothioate)s and Related Constructs," Pharmacology & Therapeutics, vol. 76, No. 1-3, pp. 161-175, 1997.
Caplen, N.J., et al., "Rescue of polyglutamine-mediated cytotoxicity by double-stranded RNA-mediated RNA Interference Human Molecular Genetics," Human Molecular Genetics, 2002, vol. 11 (2), pp. 175-184.
Cooper, T.A., "Neutralizing Toxic RNA," Science, vol. 325, pp. 272-273, Jul. 2009.
Devor, E.J., et al., "Oligonucleotide Yield, Resuspension, and Storage," Integrated DNA Technologies, pp. 1-11, 2005.
Eder, I.E., et al., "Inhibition of LNCaP prostate cancer cells by means of androgen receptor antisense oligonucleotides," Cancer Gene Therapy, vol. 7, No. 7, pp. 997-1007, 2000.
Folini, M., et al., "Antisense oligonucleotide-mediated inhibition of hTERT, but not hTERC, induces rapid cell growth decline and apoptosis in the absence of telomere shortening in human prostate cancer cells," European Journal of Cancer, vol. 41, No. 4, pp. 624-634, 2005.
Fu, Y.H., et al., "An Unstable Triplet Repeat in a Gene Related to Myotonic Muscular Dystrophy," Science, 1992, vol. 255 (5049), pp. 1256-1258.
Furling, D., et al., "Viral Vector Producing Antisense RNA Restores Myotonic Dystrophy Myoblast Functions," Gene Therapy, 2003, vol. 10 (9), pp. 795-802.
Galderisi, U., et al., "Myotonic Dystrophy: Antisense Oligonucleotide Inhibition of DMPK Gene Exression in Vitro," Biochemical and Biophysical Research Communications, 1996, vol. 221 (3), pp. 750-754.
Handa, V., et al., "The AUUCU Repeats Responsible for Spinocerebellar Ataxia Type 10 Form Unusual RNA Hairpins," The Journal of Biological Chemistry, 2005, vol. 280 (32), pp. 29340-29345.
Harrison, J.G., et al., "Synthesis and Hybridization Analysis of a Small Library of Peptide-Oligonucleotide Conjugates," Nucleic Acids Research, 1998, vol. 26 (13), pp. 3136-3145.
Hasholt, L., et al., "Antisense Downregulation of Mutant Huntingtin in a Cell Model," Journal of Gene Medicine, 2003, vol. 5 (6), pp. 528-538.
Kandimalla, E.R., et al., "Effects of Phosphorothioate Oligodeoxyribonucleotide and Oligoribonucleotides on Human Complement and Coagulation," Bioorganic & Medicinal Chemistry Letters, vol. 8, No. 16, pp. 2103-2108, 1998.
Lebedev, Y., et al., "Oligonucleotides containing 2-aminoadenine and 5-methylcytosine are more effective as primers for PCR amplification than their nonmodified counterparts," Genetic Analysis: Biomolecular Engineering, vol. 13, pp. 15-21, 1996.
Liu, W., et al., "Specific Inhibition of Huntington's Disease Gene Expression by siRNAs in Cultured Cells," Proceedings of the Japan Academy, 2003, vol. 79, pp. 293-298.
Nakamori, M, et al., "Stabilization of Expanded (CTG)•(CAG) Repeats by Antisense Oligonucleotides," Molecular Therapy, vol. 19, No. 12, pp. 2222-2227, Dec. 2011.
Taneja, K.L., "Localization of Trinucleotide Repeat Sequences in Myotonic Dytrophy Cells Using a Single Fluorochrome-Labeled PNA Probe," BioTechniques, vol. 24, No. 3, pp. 472-476, Mar. 1998.
Thomsen, R., et al., "Dramatically improved RNA in situ hybridization signals using LNA-modified probes," RNA, vol. 11, pp. 1745-1748, 2005.
Wheeler, T.M., et al., "Reversal of RNA Dominance by Displacement of Protein Sequestered on Triplet Repeat RNA," Science, vol. 325, pp. 336-339, Jul. 2009.
Boado, R., et al., "Antisense-Mediated Down-Regulation of the Human Huntingtin Gene," The Journal of Pharmacology and Experimental Therapeutics, vol. 295, No. 1, pp. 239-243, 2000.

\* cited by examiner p=0.08
Htt mRNA levels (a.u.)
2.0
1.5
1.0
0.5
0.0
Saline
PS659

Htt mRNA levels (a.u.)
2.0
1.5
1.0
0.5
0.0
Saline
PS659

Htt mRNA levels (a.u.)
1.5
1.0
0.5
0.0
Saline
PS659

Htt mRNA levels (a.u.)
1.5
1.0
0.5
0.0
Saline
PS659

SEQUENCE LISTING

```
<160> NUMBER OF SEQ ID NOS: 221

<210> SEQ ID NO 1
<211> LENGTH: 21
<212> TYPE: RNA
<213> ORGANISM: Artificial
<220> FEATURE:
<223> OTHER INFORMATION: Oligonucleotide

<400> SEQUENCE: 1

cugcugcugc ugcugcugcu g                                              21


<210> SEQ ID NO 2
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
```

<400> SEQUENCE: 2
nugnugnugn ugnugnugnu g 21

<210> SEQ ID NO 3
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 3
cngcngcngc ngcngcngcn g 21

<210> SEQ ID NO 4
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil

<400> SEQUENCE: 4
nngnngnngn ng 12

<210> SEQ ID NO 5
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil

<400> SEQUENCE: 5
nngnngnngn ngnng 15

<210> SEQ ID NO 6
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)

<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil

<400> SEQUENCE: 6
nngnngnngn ngnngnng 18

<210> SEQ ID NO 7
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil

<400> SEQUENCE: 7
nngnngnngn ngnngnngnn g 21

<210> SEQ ID NO 8
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:

<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil

<400> SEQUENCE: 8
nngnngnngn ngnngnngnn gnng 24

<210> SEQ ID NO 9
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is U or 5-methyluracil

<400> SEQUENCE: 9
nngnngnngn ngnngnngnn gnngnng 27

<210> SEQ ID NO 10
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)

<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is U or 5-methyluracil

<400> SEQUENCE: 10
nngnngnngn ngnngnngnn gnngnngnng 30

<210> SEQ ID NO 11
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is U or 5-methyluracil
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (32)..(32)
<223> OTHER INFORMATION: n is U or 5-methyluracil

<400> SEQUENCE: 11
nngnngnngn ngnngnngnn gnngnngnng nng 33

<210> SEQ ID NO 12
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:

<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is U or 5-methyluracil
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (32)..(32)
<223> OTHER INFORMATION: n is U or 5-methyluracil
<220> FEATURE:
<221> NAME/KEY: misc_feature
<222> LOCATION: (34)..(34)
<223> OTHER INFORMATION: n is C or 5-methylcytosine
<220> FEATURE:
<221> NAME/KEY: misc_feature
<222> LOCATION: (35)..(35)
<223> OTHER INFORMATION: n is U or 5-methyluracil

<400> SEQUENCE: 12
nngnngnngn ngnngnngnn gnngnngnng nngnng 36

<210> SEQ ID NO 13
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine

<400> SEQUENCE: 13
ngnngnngnn gn 12

<210> SEQ ID NO 14
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)

<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine

<400> SEQUENCE: 14
ngnngnngnn gnngn 15

<210> SEQ ID NO 15
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine

<400> SEQUENCE: 15
ngnngnngnn gnngnngn 18

<210> SEQ ID NO 16
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine

<400> SEQUENCE: 16
ngnngnngnn gnngnngnng n 21

<210> SEQ ID NO 17
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 17
ngnngnngnn gnngnngnng nngn 24

<210> SEQ ID NO 18
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (27)..(27)

<223> OTHER INFORMATION: n is C or 5-methylcytosine

<400> SEQUENCE: 18
ngnngnngnn gnngnngnng nngnngn 27

<210> SEQ ID NO 19
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine

<400> SEQUENCE: 19
ngnngnngnn gnngnngnng nngnngnngn 30

<210> SEQ ID NO 20
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:

<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (33)..(33)
<223> OTHER INFORMATION: n is C or 5-methylcytosine

<400> SEQUENCE: 20
ngnngnngnn gnngnngnng nngnngnngn ngn 33

<210> SEQ ID NO 21
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (33)..(33)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is C or 5-methylcytosine
<220> FEATURE:
<221> NAME/KEY: misc_feature
<222> LOCATION: (36)..(36)
<223> OTHER INFORMATION: n is C or 5-methylcytosine

<400> SEQUENCE: 21
ngnngnngnn gnngnngnng nngnngnngn ngnngn 36

<210> SEQ ID NO 22
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)

<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine

<400> SEQUENCE: 22
nngnngnngn ng 12

<210> SEQ ID NO 23
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine

<400> SEQUENCE: 23
nngnngnngn ngnng 15

<210> SEQ ID NO 24
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine

<400> SEQUENCE: 24
nngnngnngn ngnngnng 18

<210> SEQ ID NO 25
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:

<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine

<400> SEQUENCE: 25
nngnngnngn ngnngnngnn g 21

<210> SEQ ID NO 26
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine

<400> SEQUENCE: 26
nngnngnngn ngnngnngnn gnng 24

<210> SEQ ID NO 27
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)

<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is C or 5-methylcytosine

<400> SEQUENCE: 27
nngnngnngn ngnngnngnn gnngnng 27

<210> SEQ ID NO 28
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is C or 5-methylcytosine

<400> SEQUENCE: 28
nngnngnngn ngnngnngnn gnngnngnng 30

<210> SEQ ID NO 29
<211> LENGTH: 33
<212> TYPE: RNA
<213> ORGANISM: Artificial
<220> FEATURE:
<223> OTHER INFORMATION: Oligonucleotide
<220> FEATURE:

<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (32)..(32)
<223> OTHER INFORMATION: n is C or 5-methylcytosine

<400> SEQUENCE: 29
nngnngnngn ngnngnngnn gnngnngnng nng 33

<210> SEQ ID NO 30
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine
<220> FEATURE:
<221> NAME/KEY: misc_feature
<222> LOCATION: (22)..(22)

<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (32)..(32)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is C or 5-methylcytosine
<220> FEATURE:
<221> NAME/KEY: misc_feature
<222> LOCATION: (35)..(35)
<223> OTHER INFORMATION: n is C or 5-methylcytosine

<400> SEQUENCE: 30
nngnngnngn ngnngnngnn gnngnngnng nngnng 36

<210> SEQ ID NO 31
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine

<400> SEQUENCE: 31
nnnnnnnnnn nn 12

<210> SEQ ID NO 32
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:

<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine

<400> SEQUENCE: 32
nnnnnnnnnn nnnnn 15

<210> SEQ ID NO 33
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine

<400> SEQUENCE: 33
nnnnnnnnnn nnnnnnnn 18

<210> SEQ ID NO 34
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)

<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is C or 5-methylcytosine

<400> SEQUENCE: 34
nnnnnnnnnn nnnnnnnnnn n 21

<210> SEQ ID NO 35
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine

<400> SEQUENCE: 35
nnnnnnnnnn nnnnnnnnnn nnnn 24

<210> SEQ ID NO 36
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:

<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (27)..(27)
<223> OTHER INFORMATION: n is C or 5-methylcytosine

<400> SEQUENCE: 36
nnnnnnnnnn nnnnnnnnnn nnnnnnn 27

<210> SEQ ID NO 37
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)

<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is U or 5-methyluracil
<220> FEATURE:
<221> NAME/KEY: misc_feature
<222> LOCATION: (29)..(29)
<223> OTHER INFORMATION: n is U or 5-methyluracil
<220> FEATURE:
<221> NAME/KEY: misc_feature
<222> LOCATION: (30)..(30)
<223> OTHER INFORMATION: n is C or 5-methylcytosine

<400> SEQUENCE: 37
nnnnnnnnnn nnnnnnnnnn nnnnnnnnnn 30

<210> SEQ ID NO 38
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:

<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is U or 5-methyluracil
<220> FEATURE:
<221> NAME/KEY: misc_feature
<222> LOCATION: (29)..(29)
<223> OTHER INFORMATION: n is U or 5-methyluracil
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is U or 5-methyluracil
<220> FEATURE:
<221> NAME/KEY: misc_feature
<222> LOCATION: (32)..(32)
<223> OTHER INFORMATION: n is U or 5-methyluracil
<220> FEATURE:
<221> NAME/KEY: misc_feature
<222> LOCATION: (33)..(33)
<223> OTHER INFORMATION: n is C or 5-methylcytosine

<400> SEQUENCE: 38
nnnnnnnnnn nnnnnnnnnn nnnnnnnnnn nnn 33

<210> SEQ ID NO 39
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)

<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is U or 5-methyluracil
<220> FEATURE:
<221> NAME/KEY: misc_feature
<222> LOCATION: (29)..(29)
<223> OTHER INFORMATION: n is U or 5-methyluracil
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is U or 5-methyluracil
<220> FEATURE:
<221> NAME/KEY: misc_feature
<222> LOCATION: (32)..(32)
<223> OTHER INFORMATION: n is U or 5-methyluracil
<220> FEATURE:
<221> NAME/KEY: misc_feature
<222> LOCATION: (33)..(33)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is U or 5-methyluracil
<220> FEATURE:
<221> NAME/KEY: misc_feature
<222> LOCATION: (35)..(35)
<223> OTHER INFORMATION: n is U or 5-methyluracil
<220> FEATURE:
<221> NAME/KEY: misc_feature
<222> LOCATION: (36)..(36)
<223> OTHER INFORMATION: n is C or 5-methylcytosine

<400> SEQUENCE: 39
nnnnnnnnnn nnnnnnnnnn nnnnnnnnnn nnnnnn 36

<210> SEQ ID NO 40
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine

<400> SEQUENCE: 40
ggnggnggng gn 12

<210> SEQ ID NO 41
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine

<400> SEQUENCE: 41
ggnggnggng gnggn 15

<210> SEQ ID NO 42
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine

<400> SEQUENCE: 42
ggnggnggng gnggnggn 18

<210> SEQ ID NO 43
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine

<400> SEQUENCE: 43
ggnggnggng gnggnggngg n 21

<210> SEQ ID NO 44
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 44
ggnggnggng gnggnggngg nggn 24

<210> SEQ ID NO 45
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine

<400> SEQUENCE: 45
ggnggnggng gnggnggngg nggnggn 27

<210> SEQ ID NO 46
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)

<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine

<400> SEQUENCE: 46
ggnggnggng gnggnggngg nggnggnggn 30

<210> SEQ ID NO 47
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (33)..(33)
<223> OTHER INFORMATION: n is C or 5-methylcytosine

<400> SEQUENCE: 47
ggnggnggng gnggnggngg nggnggnggn ggn 33

<210> SEQ ID NO 48
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (33)..(33)
<223> OTHER INFORMATION: n is C or 5-methylcytosine
<220> FEATURE:
<221> NAME/KEY: misc_feature
<222> LOCATION: (36)..(36)
<223> OTHER INFORMATION: n is C or 5-methylcytosine

<400> SEQUENCE: 48
ggnggnggng gnggnggngg nggnggnggn ggnggn 36

<210> SEQ ID NO 49
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:

<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine

<400> SEQUENCE: 49
nggnggnggn gg 12

<210> SEQ ID NO 50
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine

<400> SEQUENCE: 50
nggnggnggn ggngg 15

<210> SEQ ID NO 51
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine

<400> SEQUENCE: 51
nggnggnggn ggnggngg 18

<210> SEQ ID NO 52
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine

<400> SEQUENCE: 52
nggnggnggn ggnggnggng g 21

<210> SEQ ID NO 53
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)

<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine

<400> SEQUENCE: 53
nggnggnggn ggnggnggng gngg 24

<210> SEQ ID NO 54
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine

<400> SEQUENCE: 54
nggnggnggn ggnggnggng gnggngg 27

<210> SEQ ID NO 55
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine

<400> SEQUENCE: 55
nggnggnggn ggnggnggng gnggnggngg 30

<210> SEQ ID NO 56
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:

<221> NAME/KEY: misc_feature
<222> LOCATION: (31)..(31)
<223> OTHER INFORMATION: n is C or 5-methylcytosine

<400> SEQUENCE: 56
nggnggnggn ggnggnggng gnggnggngg ngg 33

<210> SEQ ID NO 57
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is C or 5-methylcytosine

<400> SEQUENCE: 57
nggnggnggn ggnggnggng gnggnggngg nggngg 36

<210> SEQ ID NO 58
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
<222> LOCATION: (4)..(4)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (8)..(8)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil

<400> SEQUENCE: 58
ngnnnngnnn ngnnn 15

<210> SEQ ID NO 59
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
<222> LOCATION: (4)..(4)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (8)..(8)

<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil
<220> FEATURE:
<221> NAME/KEY: misc_feature
<222> LOCATION: (16)..(16)
<223> OTHER INFORMATION: n is A or 2,6-diaminopurine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (19)..(19)
<223> OTHER INFORMATION: n is A or 2,6-diaminopurine
<220> FEATURE:
<221> NAME/KEY: misc_feature
<222> LOCATION: (20)..(20)
<223> OTHER INFORMATION: n is U or 5-methyluracil

<400> SEQUENCE: 59
ngnnnngnnn ngnnnngnnn 20

<210> SEQ ID NO 60
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
<222> LOCATION: (4)..(4)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (8)..(8)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil
<220> FEATURE:
<221> NAME/KEY: misc_feature
<222> LOCATION: (16)..(16)
<223> OTHER INFORMATION: n is A or 2,6-diaminopurine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (19)..(19)
<223> OTHER INFORMATION: n is A or 2,6-diaminopurine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is A or 2,6-diaminopurine
<220> FEATURE:
<221> NAME/KEY: misc_feature
<222> LOCATION: (23)..(23)
<223> OTHER INFORMATION: n is A or 2,6-diaminopurine
<220> FEATURE:
<221> NAME/KEY: misc_feature
<222> LOCATION: (24)..(24)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is U or 5-methyluracil

<400> SEQUENCE: 60
ngnnnngnnn ngnnnngnnn ngnnn 25

<210> SEQ ID NO 61
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
<222> LOCATION: (4)..(4)
<223> OTHER INFORMATION: n is A or 2,6-diaminopurine
<220> FEATURE:

<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (8)..(8)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil
<220> FEATURE:
<221> NAME/KEY: misc_feature
<222> LOCATION: (16)..(16)
<223> OTHER INFORMATION: n is A or 2,6-diaminopurine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (19)..(19)
<223> OTHER INFORMATION: n is A or 2,6-diaminopurine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is A or 2,6-diaminopurine
<220> FEATURE:
<221> NAME/KEY: misc_feature
<222> LOCATION: (23)..(23)
<223> OTHER INFORMATION: n is A or 2,6-diaminopurine
<220> FEATURE:
<221> NAME/KEY: misc_feature
<222> LOCATION: (24)..(24)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is A or 2,6-diaminopurine
<220> FEATURE:
<221> NAME/KEY: misc_feature
<222> LOCATION: (28)..(28)
<223> OTHER INFORMATION: n is A or 2,6-diaminopurine
<220> FEATURE:
<221> NAME/KEY: misc_feature
<222> LOCATION: (29)..(29)
<223> OTHER INFORMATION: n is A or 2,6-diaminopurine
<220> FEATURE:
<221> NAME/KEY: misc_feature
<222> LOCATION: (30)..(30)
<223> OTHER INFORMATION: n is U or 5-methyluracil

<400> SEQUENCE: 61
ngnnnngnnn ngnnnngnnn ngnnnngnnn 30

<210> SEQ ID NO 62
<211> LENGTH: 35
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
<222> LOCATION: (4)..(4)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (8)..(8)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil
<220> FEATURE:
<221> NAME/KEY: misc_feature
<222> LOCATION: (16)..(16)
<223> OTHER INFORMATION: n is A or 2,6-diaminopurine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (19)..(19)
<223> OTHER INFORMATION: n is A or 2,6-diaminopurine
<220> FEATURE:
<221> NAME/KEY: misc_feature
<222> LOCATION: (20)..(20)

<223> OTHER INFORMATION: n is U or 5-methyluracil
<220> FEATURE:
<221> NAME/KEY: misc_feature
<222> LOCATION: (21)..(21)
<223> OTHER INFORMATION: n is A or 2,6-diaminopurine
<220> FEATURE:
<221> NAME/KEY: misc_feature
<222> LOCATION: (23)..(23)
<223> OTHER INFORMATION: n is A or 2,6-diaminopurine
<220> FEATURE:
<221> NAME/KEY: misc_feature
<222> LOCATION: (24)..(24)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is A or 2,6-diaminopurine
<220> FEATURE:
<221> NAME/KEY: misc_feature
<222> LOCATION: (28)..(28)
<223> OTHER INFORMATION: n is A or 2,6-diaminopurine
<220> FEATURE:
<221> NAME/KEY: misc_feature
<222> LOCATION: (29)..(29)
<223> OTHER INFORMATION: n is A or 2,6-diaminopurine
<220> FEATURE:
<221> NAME/KEY: misc_feature
<222> LOCATION: (30)..(30)
<223> OTHER INFORMATION: n is U or 5-methyluracil
<220> FEATURE:
<221> NAME/KEY: misc_feature
<222> LOCATION: (31)..(31)
<223> OTHER INFORMATION: n is A or 2,6-diaminopurine
<220> FEATURE:
<221> NAME/KEY: misc_feature
<222> LOCATION: (33)..(33)
<223> OTHER INFORMATION: n is A or 2,6-diaminopurine
<220> FEATURE:
<221> NAME/KEY: misc_feature
<222> LOCATION: (34)..(34)
<223> OTHER INFORMATION: n is A or 2,6-diaminopurine
<220> FEATURE:
<221> NAME/KEY: misc_feature
<222> LOCATION: (35)..(35)
<223> OTHER INFORMATION: n is U or 5-methyluracil

<400> SEQUENCE: 62
ngnnnngnnn ngnnnngnnn ngnnnngnnn ngnnn 35

<210> SEQ ID NO 63
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine

<400> SEQUENCE: 63
nnggnnggnn gg 12

<210> SEQ ID NO 64
<211> LENGTH: 16
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine

<400> SEQUENCE: 64
nnggnnggnn ggnngg 16

<210> SEQ ID NO 65
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:

<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine

<400> SEQUENCE: 65
nnggnnggnn ggnnggnngg 20

<210> SEQ ID NO 66
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is A or 2,6-diaminopurine

<400> SEQUENCE: 66
nnggnnggnn ggnnggnngg nngg 24

<210> SEQ ID NO 67
<211> LENGTH: 28
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is A or 2,6-diaminopurine

<400> SEQUENCE: 67
nnggnnggnn ggnnggnngg nnggnngg 28

<210> SEQ ID NO 68

<211> LENGTH: 32
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is A or 2,6-diaminopurine
<220> FEATURE:
<221> NAME/KEY: misc_feature
<222> LOCATION: (29)..(29)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is A or 2,6-diaminopurine

<400> SEQUENCE: 68
nnggnnggnn ggnnggnngg nnggnnggnn gg 32

<210> SEQ ID NO 69
<211> LENGTH: 36
<212> TYPE: RNA
<213> ORGANISM: Artificial

<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is A or 2,6-diaminopurine
<220> FEATURE:
<221> NAME/KEY: misc_feature
<222> LOCATION: (29)..(29)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is A or 2,6-diaminopurine
<220> FEATURE:
<221> NAME/KEY: misc_feature
<222> LOCATION: (33)..(33)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is A or 2,6-diaminopurine

<400> SEQUENCE: 69
nnggnnggnn ggnnggnngg nnggnnggnn ggnngg 36

<210> SEQ ID NO 70
<211> LENGTH: 23
<212> TYPE: DNA
<213> ORGANISM: Artificial
<220> FEATURE:
<223> OTHER INFORMATION: Primer

<400> SEQUENCE: 70
atggcgaccc tggaaaagct gat 23

<210> SEQ ID NO 71
<211> LENGTH: 17
<212> TYPE: DNA
<213> ORGANISM: Artificial
<220> FEATURE:
<223> OTHER INFORMATION: Primer

<400> SEQUENCE: 71
tgaggcagca gcggctg 17

<210> SEQ ID NO 72
<211> LENGTH: 20
<212> TYPE: DNA
<213> ORGANISM: Artificial
<220> FEATURE:
<223> OTHER INFORMATION: Primer

<400> SEQUENCE: 72
ggacttcgag caagagatgg 20

<210> SEQ ID NO 73
<211> LENGTH: 20
<212> TYPE: DNA
<213> ORGANISM: Artificial
<220> FEATURE:
<223> OTHER INFORMATION: Primer

<400> SEQUENCE: 73
agcactgtgt tggcgtacag 20

<210> SEQ ID NO 74
<211> LENGTH: 18
<212> TYPE: DNA
<213> ORGANISM: Artificial
<220> FEATURE:
<223> OTHER INFORMATION: Primer

<400> SEQUENCE: 74
cgccgcctcc tcagcttc 18

<210> SEQ ID NO 75
<211> LENGTH: 24
<212> TYPE: DNA
<213> ORGANISM: Artificial
<220> FEATURE:
<223> OTHER INFORMATION: Primer

<400> SEQUENCE: 75
gagagttcct tctttggtcg gtgc 24

<210> SEQ ID NO 76
<211> LENGTH: 23
<212> TYPE: DNA
<213> ORGANISM: Artificial
<220> FEATURE:
<223> OTHER INFORMATION: Primer

<400> SEQUENCE: 76
tgggaaacag ataaaactcc aga 23

<210> SEQ ID NO 77
<211> LENGTH: 26
<212> TYPE: DNA
<213> ORGANISM: Artificial
<220> FEATURE:
<223> OTHER INFORMATION: Primer

<400> SEQUENCE: 77
aatatgacct tgtgatagaa cgaaag 26

<210> SEQ ID NO 78
<211> LENGTH: 20
<212> TYPE: DNA
<213> ORGANISM: Artificial
<220> FEATURE:
<223> OTHER INFORMATION: Primer

<400> SEQUENCE: 78
aaatgagctg gtgcagaagg 20

<210> SEQ ID NO 79
<211> LENGTH: 19
<212> TYPE: DNA
<213> ORGANISM: Artificial
<220> FEATURE:
<223> OTHER INFORMATION: Primer

<400> SEQUENCE: 79
ggctgccatg tcatcgtat 19

<210> SEQ ID NO 80
<211> LENGTH: 13481
<212> TYPE: DNA
<213> ORGANISM: Homo sapiens

<400> SEQUENCE: 80
gctgccggga cgggtccaag atggacggcc gctcaggttc tgcttttacc tgcggcccag 60
agccccattc attgccccgg tgctgagcgg cgccgcgagt cggcccgagg cctccgggga 120
ctgccgtgcc gggcgggaga ccgccatggc gaccctggaa aagctgatga aggccttcga 180
gtccctcaag tccttccagc agcagcagca gcagcagcag cagcagcagc agcagcagca 240
gcagcagcag cagcagcagc aacagccgcc accgccgccg ccgccgccgc cgcctcctca 300
gcttcctcag ccgccgccgc aggcacagcc gctgctgcct cagccgcagc cgcccccgcc 360
gccgcccccg ccgccacccg gcccggctgt ggctgaggag ccgctgcacc gaccaaagaa 420
agaactttca gctaccaaga aagaccgtgt gaatcattgt ctgacaatat gtgaaaacat 480
agtggcacag tctgtcagaa attctccaga atttcagaaa cttctgggca tcgctatgga 540
actttttctg ctgtgcagtg atgacgcaga gtcagatgtc aggatggtgg ctgacgaatg 600
cctcaacaaa gttatcaaag ctttgatgga ttctaatctt ccaaggttac agctcgagct 660
ctataaggaa attaaaaaga atggtgcccc tcggagtttg cgtgctgccc tgtggaggtt 720
tgctgagctg gctcacctgg ttcggcctca gaaatgcagg ccttacctgg tgaaccttct 780
gccgtgcctg actcgaacaa gcaagagacc cgaagaatca gtccaggaga ccttggctgc 840
agctgttccc aaaattatgg cttcttttgg caattttgca aatgacaatg aaattaaggt 900

-continued

```
tttgttaaag gccttcatag cgaacctgaa gtcaagctcc cccaccattc ggcggacagc    960
ggctggatca gcagtgagca tctgccagca ctcaagaagg acacaatatt tctatagttg   1020
gctactaaat gtgctcttag gcttactcgt tcctgtcgag gatgaacact ccactctgct   1080
gattcttggc gtgctgctca ccctgaggta tttggtgccc ttgctgcagc agcaggtcaa   1140
ggacacaagc ctgaaaggca gcttcggagt gacaaggaaa gaaatggaag tctctccttc   1200
tgcagagcag cttgtccagg tttatgaact gacgttacat catacacagc accaagacca   1260
caatgttgtg accggagccc tggagctgtt gcagcagctc ttcagaacgc ctccacccga   1320
gcttctgcaa accctgaccg cagtcggggg cattgggcag ctcaccgctg ctaaggagga   1380
gtctggtggc cgaagccgta gtgggagtat tgtggaactt atagctggag gggttcctc    1440
atgcagccct gtcctttcaa gaaaacaaaa aggcaaagtg ctcttaggag aagaagaagc   1500
cttggaggat gactctgaat cgagatcgga tgtcagcagc tctgccttaa cagcctcagt   1560
gaaggatgag atcagtggag agctggctgc ttcttcaggg gtttccactc cagggtcagc   1620
aggtcatgac atcatcacag aacagccacg gtcacagcac acactgcagg cggactcagt   1680
ggatctggcc agctgtgact tgacaagctc tgccactgat ggggatgagg aggatatctt   1740
gagccacagc tccagccagg tcagcgccgt cccatctgac cctgccatgg acctgaatga   1800
tgggacccag gcctcgtcgc ccatcagcga cagctcccag accaccaccg aagggcctga   1860
ttcagctgtt accccttcag acagttctga aattgtgtta gacggtaccg acaaccagta   1920
tttgggcctg cagattggac agccccagga tgaagatgag gaagccacag gtattcttcc   1980
tgatgaagcc tcggaggcct tcaggaactc ttccatggcc cttcaacagg cacatttatt   2040
gaaaaacatg agtcactgca ggcagccttc tgacagcagt gttgataaat ttgtgttgag   2100
agatgaagct actgaaccgg gtgatcaaga aaacaagcct tgccgcatca aaggtgacat   2160
tggacagtcc actgatgatg actctgcacc tcttgtccat tgtgtccgcc ttttatctgc   2220
ttcgtttttg ctaacagggg gaaaaaatgt gctggttccg gacagggatg tgagggtcag   2280
cgtgaaggcc ctggccctca gctgtgtggg agcagctgtg gccctccacc cggaatcttt   2340
cttcagcaaa ctctataaag ttcctcttga caccacggaa taccctgagg aacagtatgt   2400
ctcagacatc ttgaactaca tcgatcatgg agacccacag gttcgaggag ccactgccat   2460
tctctgtggg accctcatct gctccatcct cagcaggtcc cgcttccacg tgggagattg   2520
gatgggcacc attagaaccc tcacaggaaa tacattttct ttggcggatt gcattccttt   2580
gctgcggaaa acactgaagg atgagtcttc tgttacttgc aagttagctt gtacagctgt   2640
gaggaactgt gtcatgagtc tctgcagcag cagctacagt gagttaggac tgcagctgat   2700
catcgatgtg ctgactctga ggaacagttc ctattggctg gtgaggacag agcttctgga   2760
aacccttgca gagattgact tcaggctggt gagcttttg gaggcaaaag cagaaaactt    2820
acacagaggg gctcatcatt atacagggct tttaaaactg caagaacgag tgctcaataa   2880
tgttgtcatc catttgcttg gagatgaaga ccccagggtg cgacatgttg ccgcagcatc   2940
actaattagg cttgtcccaa agctgtttta taaatgtgac caaggacaag ctgatccagt   3000
agtggccgtg gcaagagatc aaagcagtgt ttacctgaaa cttctcatgc atgagacgca   3060
gcctccatct catttctccg tcagcacaat aaccagaata tatagaggct ataacctact   3120
accaagcata acagacgtca ctatggaaaa taacctttca agagttattg cagcagtttc   3180
tcatgaacta atcacatcaa ccaccagagc actcacattt ggatgctgtg aagctttgtg   3240
tcttctttcc actgccttcc cagtttgcat ttggagttta ggttggcact gtggagtgcc   3300
```

-continued

```
tccactgagt gcctcagatg agtctaggaa gagctgtacc gttgggatgg ccacaatgat   3360
tctgaccctg ctctcgtcag cttggttccc attggatctc tcagcccatc aagatgcttt   3420
gattttggcc ggaaacttgc ttgcagccag tgctcccaaa tctctgagaa gttcatgggc   3480
ctctgaagaa gaagccaacc cagcagccac caagcaagag gaggtctggc cagccctggg   3540
ggaccgggcc ctggtgccca tggtggagca gctcttctct cacctgctga aggtgattaa   3600
catttgtgcc cacgtcctgg atgacgtggc tcctggaccc gcaataaagg cagccttgcc   3660
ttctctaaca aacccccctt ctctaagtcc catccgacga aaggggaagg agaaagaacc   3720
aggagaacaa gcatctgtac cgttgagtcc caagaaaggc agtgaggcca gtgcagcttc   3780
tagacaatct gatacctcag gtcctgttac aacaagtaaa tcctcatcac tggggagttt   3840
ctatcatctt ccttcatacc tcaaactgca tgatgtcctg aaagctacac acgctaacta   3900
caaggtcacg ctggatcttc agaacagcac ggaaaagttt ggagggtttc tccgctcagc   3960
cttggatgtt ctttctcaga tactagagct ggccacactg caggacattg ggaagtgtgt   4020
tgaagagatc ctaggatacc tgaaatcctg ctttagtcga gaaccaatga tggcaactgt   4080
ttgtgttcaa caattgttga agactctctt tggcacaaac ttggcctccc agtttgatgg   4140
cttatcttcc aaccccagca agtcacaagg ccgagcacag cgccttggct cctccagtgt   4200
gaggccaggc ttgtaccact actgcttcat ggccccgtac acccacttca cccaggccct   4260
cgctgacgcc agcctgagga acatggtgca ggcggagcag gagaacgaca cctcgggatg   4320
gtttgatgtc ctccagaaag tgtctaccca gttgaagaca aacctcacga gtgtcacaaa   4380
gaaccgtgca gataagaatg ctattcataa tcacattcgt ttgtttgaac ctcttgttat   4440
aaaagcttta aaacagtaca cgactacaac atgtgtgcag ttacagaagc aggttttaga   4500
tttgctggcg cagctggttc agttacgggt taattactgt cttctggatt cagatcaggt   4560
gtttattggc tttgtattga aacagtttga atacattgaa gtgggccagt tcagggaatc   4620
agaggcaatc attccaaaca tctttttctt cttggtatta ctatcttatg aacgctatca   4680
ttcaaaacag atcattggaa ttcctaaaat cattcagctc tgtgatggca tcatggccag   4740
tggaaggaag gctgtgacac atgccatacc ggctctgcag cccatagtcc acgacctctt   4800
tgtattaaga ggaacaaata aagctgatgc aggaaaagag cttgaaaccc aaaaagaggt   4860
ggtggtgtca atgttactga gactcatcca gtaccatcag gtgttggaga tgttcattct   4920
tgtcctgcag cagtgccaca aggagaatga agacaagtgg aagcgactgt ctcgacagat   4980
agctgacatc atcctcccaa tgttagccaa acagcagatg cacattgact ctcatgaagc   5040
ccttggagtg ttaaatacat tatttgagat tttggcccct tcctccctcc gtccggtaga   5100
catgctttta cggagtatgt tcgtcactcc aaacacaatg gcgtccgtga gcactgttca   5160
actgtggata tcgggaattc tggccatttt gagggttctg atttcccagt caactgaaga   5220
tattgttctt tctcgtattc aggagctctc cttctctccg tatttaatct cctgtacagt   5280
aattaatagg ttaagagatg gggacagtac ttcaacgcta gaagaacaca gtgaagggaa   5340
acaaataaag aatttgccag aagaaacatt ttcaaggttt ctattacaac tggttggtat   5400
tcttttagaa gacattgtta caaaacagct gaaggtggaa atgagtgagc agcaacatac   5460
tttctattgc caggaactag gcacactgct aatgtgtctg atccacatct tcaagtctgg   5520
aatgttccgg agaatcacag cagctgccac taggctgttc cgcagtgatg gctgtggcgg   5580
cagtttctac accctggaca gcttgaactt gcgggctcgt tccatgatca ccacccaccc   5640
```

-continued

```
ggccctggtg ctgctctggt gtcagatact gctgcttgtc aaccacaccg actaccgctg   5700
gtgggcagaa gtgcagcaga ccccgaaaag acacagtctg tccagcacaa agttacttag   5760
tccccagatg tctggagaag aggaggattc tgacttggca gccaaacttg gaatgtgcaa   5820
tagagaaata gtacgaagag gggctctcat tctcttctgt gattatgtct gtcagaacct   5880
ccatgactcc gagcacttaa cgtggctcat tgtaaatcac attcaagatc tgatcagcct   5940
ttcccacgag cctccagtac aggacttcat cagtgccgtt catcggaact ctgctgccag   6000
cggcctgttc atccaggcaa ttcagtctcg ttgtgaaaac ctttcaactc caaccatgct   6060
gaagaaaact cttcagtgct tggaggggat ccatctcagc cagtcgggag ctgtgctcac   6120
gctgtatgtg gacaggcttc tgtgcacccc tttccgtgtg ctggctcgca tggtcgacat   6180
ccttgcttgt cgccgggtag aaatgcttct ggctgcaaat ttacagagca gcatggccca   6240
gttgccaatg gaagaactca acagaatcca ggaatacctt cagagcagcg ggctcgctca   6300
gagacaccaa aggctctatt ccctgctgga caggtttcgt ctctccacca tgcaagactc   6360
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc ctgctagctc catgcttaag   6600
cctagggatg agtgaaattt ctggtggcca gaagagtgcc ctttttgaag cagcccgtga   6660
ggtgactctg gcccgtgtga gcggcaccgt gcagcagctc cctgctgtcc atcatgtctt   6720
ccagcccgag ctgcctgcag agccggcggc ctactggagc aagttgaatg atctgtttgg   6780
ggatgctgca ctgtatcagt ccctgcccac tctggcccgg gccctggcac agtacctggt   6840
ggtggtctcc aaactgccca gtcatttgca ccttcctcct gagaaagaga aggacattgt   6900
gaaattcgtg gtggcaaccc ttgaggccct gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gcctgctccc tcatctactg   7080
tgtgcacttc atcctggagg ccgttgcagt gcagcctgga gagcagcttc ttagtccaga   7140
aagaaggaca aataccccaa aagccatcag cgaggaggag gaggaagtag atccaaacac   7200
acagaatcct aagtatatca ctgcagcctg tgagatggtg gcagaaatgg tggagtctct   7260
gcagtcggtg ttggccttgg gtcataaaag gaatagcggc gtgccggcgt ttctcacgcc   7320
attgctaagg aacatcatca tcagcctggc ccgcctgccc cttgtcaaca gctacacacg   7380
tgtgcccccca ctggtgtgga agcttggatg gtcacccaaa ccgggagggg attttggcac   7440
agcattccct gagatccccg tggagttcct ccaggaaaag gaagtcttta aggagttcat   7500
ctaccgcatc aacacactag gctggaccag tcgtactcag tttgaagaaa cttgggccac   7560
cctccttggt gtcctggtga cgcagcccct cgtgatggag caggaggaga gcccaccaga   7620
agaagacaca gagaggaccc agatcaacgt cctggccgtg caggccatca cctcactggt   7680
gctcagtgca atgactgtgc ctgtggccgg caacccagct gtaagctgct tggagcagca   7740
gccccggaac aagcctctga aagctctcga caccaggttt gggaggaagc tgagcattat   7800
cagagggatt gtggagcaag agattcaagc aatggtttca aagagagaga atattgccac   7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
```

-continued

```
cctgagggag gaggaatggg acgaggaaga ggaggaggag gccgacgccc ctgcaccttc   8100
gtcaccaccc acgtctccag tcaactccag gaaacaccgg gctggagttg acatccactc   8160
ctgttcgcag tttttgcttg agttgtacag ccgctggatc ctgccgtcca gctcagccag   8220
gaggaccccg gccatcctga tcagtgaggt ggtcagatcc cttctagtgg tctcagactt   8280
gttcaccgag cgcaaccagt ttgagctgat gtatgtgacg ctgacagaac tgcgaagggt   8340
gcacccttca gaagacgaga tcctcgctca gtacctggtg cctgccacct gcaaggcagc   8400
tgccgtcctt gggatggaca aggccgtggc ggagcctgtc agccgcctgc tggagagcac   8460
gctcaggagc agccacctgc ccagcagggt tggagccctg cacggcgtcc tctatgtgct   8520
ggagtgcgac ctgctggacg acactgccaa gcagctcatc ccggtcatca gcgactatct   8580
cctctccaac ctgaaaggga tcgcccactg cgtgaacatt cacagccagc agcacgtact   8640
ggtcatgtgt gccactgcgt tttacctcat tgagaactat cctctggacg tagggccgga   8700
attttcagca tcaataatac agatgtgtgg ggtgatgctg tctggaagtg aggagtccac   8760
cccctccatc atttaccact gtgccctcag aggcctggag cgcctcctgc tctctgagca   8820
gctctcccgc ctggatgcag aatcgctggt caagctgagt gtggacagag tgaacgtgca   8880
cagcccgcac cgggccatgg cggctctggg cctgatgctc acctgcatgt acacaggaaa   8940
ggagaaagtc agtccgggta gaacttcaga ccctaatcct gcagcccccg acagcgagtc   9000
agtgattgtt gctatggagc gggtatctgt tctttttgat aggatcagga aaggctttcc   9060
ttgtgaagcc agagtggtgg ccaggatcct gccccagttt ctagacgact tcttcccacc   9120
ccaggacatc atgaacaaag tcatcggaga gtttctgtcc aaccagcagc catacccccca   9180
gttcatggcc accgtggtgt ataaggtgtt tcagactctg cacagcaccg ggcagtcgtc   9240
catggtccgg gactgggtca tgctgtccct ctccaacttc acgcagaggg ccccggtcgc   9300
catggccacg tggagcctct cctgcttctt tgtcagcgcg tccaccagcc cgtgggtcgc   9360
ggcgatcctc ccacatgtca tcagcaggat gggcaagctg gagcaggtgg acgtgaacct   9420
tttctgcctg gtcgccacag acttctacag acaccagata gaggaggagc tcgaccgcag   9480
ggccttccag tctgtgcttg aggtggttgc agccccagga agcccatatc accggctgct   9540
gacttgttta cgaaatgtcc acaaggtcac cacctgctga gcgccatggt gggagagact   9600
gtgaggcggc agctggggcc ggagcctttg gaagtctgcg cccttgtgcc ctgcctccac   9660
cgagccagct tggtccctat gggcttccgc acatgccgcg ggcggccagg caacgtgcgt   9720
gtctctgcca tgtggcagaa gtgctctttg tggcagtggc caggcaggga gtgtctgcag   9780
tcctggtggg gctgagcctg aggccttcca gaaagcagga gcagctgtgc tgcaccccat   9840
gtgggtgacc aggtcctttc tcctgatagt cacctgctgg ttgttgccag gttgcagctg   9900
ctcttgcatc tgggccagaa gtcctccctc ctgcaggctg gctgttggcc cctctgctgt   9960
cctgcagtag aaggtgccgt gagcaggctt tgggaacact ggcctgggtc tccctggtgg  10020
ggtgtgcatg ccacgccccg tgtctggatg cacagatgcc atggcctgtg ctgggccagt  10080
ggctgggggt gctagacacc cggcaccatt ctcccttctc tcttttcttc tcaggattta  10140
aaatttaatt atatcagtaa agagattaat tttaacgtaa ctctttctat gcccgtgtaa  10200
agtatgtgaa tcgcaaggcc tgtgctgcat gcgacagcgt ccggggtggt ggacagggcc  10260
cccggccacg ctccctctcc tgtagccact ggcatagccc tcctgagcac ccgctgacat  10320
ttccgttgta catgttcctg tttatgcatt cacaaggtga ctgggatgta gagaggcgtt  10380
```

-continued agtgggcagg tggccacagc aggactgagg acaggccccc attatcctag ggtgcgctc 10440 acctgcagcc cctcctcctc gggcacagac gactgtcgtt ctccacccac cagtcaggga 10500
cagcagcctc cctgtcactc agctgagaag gccagccctc cctggctgtg agcagcctcc 10560
actgtgtcca gagacatggg cctcccactc ctgttccttg ctagccctgg ggtggcgtct 10620
gcctaggagc tggctggcag gtgttgggac ctgctgctcc atggatgcat gccctaagag 10680
tgtcactgag ctgtgttttg tctgagcctc tctcggtcaa cagcaaagct tggtgtcttg 10740
gcactgttag tgacagagcc cagcatccct tctgccccg ttccagctga catcttgcac 10800
ggtgacccct tttagtcagg agagtgcaga tctgtgctca tcggagactg ccccacggcc 10860
ctgtcagagc cgccactcct atccccaggc caggtccctg gaccagcctc ctgtttgcag 10920
gcccagagga gccaagtcat taaaatggaa gtggattctg gatggccggg ctgctgctga 10980
tgtaggagct ggatttggga gctctgcttg ccgactggct gtgagacgag gcaggggctc 11040
tgcttcctca gccctagagg cgagccaggc aaggttggcg actgtcatgt ggcttggttt 11100
ggtcatgccc gtcgatgttt tgggtattga atgtggtaag tggaggaaat gttggaactc 11160
tgtgcaggtg ctgccttgag acccccaagc ttccacctgt ccctctccta tgtggcagct 11220
ggggagcagc tgagatgtgg acttgtatgc tgcccacata cgtgaggggg agctgaaagg 11280
gagcccctcc tctgagcagc ctctgccagg cctgtatgag gcttttccca ccagctccca 11340
acagaggcct cccccagcca ggaccacctc gtcctcgtgg cggggcagca ggagcggtag 11400
aaaggggtcc gatgtttgag gaggccctta agggaagcta ctgaattata acacgtaaga 11460
aaatcaccat tccgtattgg ttgggggctc ctgtttctca tcctagcttt ttcctggaaa 11520
gcccgctaga aggtttggga acgaggggaa agttctcaga actgttggct gctccccacc 11580
cgcctcccgc ctcccccgca ggttatgtca gcagctctga gacagcagta tcacaggcca 11640
gatgttgttc ctggctagat gtttacattt gtaagaaata acactgtgaa tgtaaaacag 11700
agccattccc ttggaatgca tatcgctggg ctcaacatag agtttgtctt cctcttgttt 11760
acgacgtgat ctaaaccagt ccttagcaag ggctcagaa caccccgctc tggcagtagg 11820
tgtcccccac ccccaaagac ctgcctgtgt gctccggaga tgaatatgag ctcattagta 11880
aaaatgactt cacccacgca tatacataaa gtatccatgc atgtgcatat agacacatct 11940
ataattttac acacacacct ctcaagacgg agatgcatgg cctctaagag tgcccgtgtc 12000
ggttcttcct ggaagttgac tttccttaga cccgccaggt caagttagcc gcgtgacgga 12060
catccaggcg tgggacgtgg tcagggcagg gctcattcat tgcccactag gatcccactg 12120
gcgaagatgg tctccatatc agctctctgc agaagggagg aagactttat catgttccta 12180
aaaatctgtg gcaagcaccc atcgtattat ccaaattttg ttgcaaatgt gattaatttg 12240
gttgtcaagt tttgggggtg ggctgtgggg agattgcttt tgttttcctg ctggtaatat 12300
cgggaaagat tttaatgaaa ccagggtaga attgtttggc aatgcactga agcgtgtttc 12360
tttcccaaaa tgtgcctccc ttccgctgcg ggcccagctg agtctatgta ggtgatgttt 12420
ccagctgcca agtgctcttt gttactgtcc accctcattt ctgccagcgc atgtgtcctt 12480
tcaaggggaa aatgtgaagc tgaacccccct ccagacaccc agaatgtagc atctgagaag 12540
gccctgtgcc ctaaaggaca cccctcgccc ccatcttcat ggagggggtc atttcagagc 12600
cctcggagcc aatgaacagc tcctcctctt ggagctgaga tgagccccac gtggagctcg 12660
ggacggatag tagacagcaa taactcggtg tgtggccgcc tggcaggtgg aacttcctcc 12720
cgttgcgggg tggagtgagg ttagttctgt gtgtctggtg ggtggagtca ggcttctctt 12780

```
gctacctgtg agcatccttc ccagcagaca tcctcatcgg gctttgtccc tcccccgctt  12840

cctccctctg cggggaggac ccgggaccac agctgctggc cagggtagac ttggagctgt  12900

cctccagagg ggtcacgtgt aggagtgaga agaaggaaga tcttgagagc tgctgaggga  12960

ccttggagag ctcaggatgg ctcagacgag gacactcgct tgccgggcct gggcctcctg  13020

ggaaggaggg agctgctcag aatgccgcat gacaactgaa ggcaacctgg aaggttcagg  13080

ggccgctctt cccccatgtg cctgtcacgc tctggtgcag tcaaaggaac gccttcccct  13140

cagttgtttc taagagcaga gtctcccgct gcaatctggg tggtaactgc cagccttgga  13200

ggatcgtggc caacgtggac ctgcctacgg agggtgggct ctgacccaag tggggcctcc  13260

ttgtccaggt ctcactgctt tgcaccgtgg tcagagggac tgtcagctga gcttgagctc  13320

ccctggagcc agcagggctg tgatgggcga gtcccggagc cccacccaga cctgaatgct  13380

tctgagagca aagggaagga ctgacgagag atgtatattt aatttttttaa ctgctgcaaa  13440

cattgtacat ccaaattaaa ggaaaaaaat ggaaaccatc a                      13481
```

<210> SEQ ID NO 81
<211> LENGTH: 10636
<212> TYPE: DNA
<213> ORGANISM: Homo sapiens

<400> SEQUENCE: 81

```
gaggagagag cagagtatac cgcagacatc atttctacta cagtggcgga gccgtacagg     60

acctgtttca ctgcaggggg atccaaaaca agccccgtgg agcagcagcc agagcaacag    120

cagccgcaag acattgtttc tctccctctg ccccccttc cccacgcaac cccagatcca    180

tttacacttt acagttttac ctcacaaaaa ctactacaag caccaagctc cctgatggaa    240

aggagcatcg tgcatcaagt caccagggtg gtccattcaa gctgcagatt tgtttgtcat    300

ccttgtacag caatctcctc ctccactgcc actacaggga agtgcatcac atgtcagcat    360

actggagcat agtgaaagag tctattttga agcttcaaac ttagtgctgc tgcagaccag    420

gaacaagaga gaaagagtgg atttcagcct gcacggatgg tcttgaaaca caaatggttt    480

ttggtctagg cgttttacac tgagattctc cactgccacc ctttctactc aagcaaaatc    540

ttcgtgaaaa gatctgctgc aaggaactga tagcttatgg ttctccattg tgatgaaagc    600

acatggtaca gttttccaaa gaaattagac cattttcttc gtgagaaaga aatcgacgtg    660

ctgttttcat agggtatttc tcacttctct gtgaaaggaa gaaagaacac gcctgagccc    720

aagagccctc aggagccctc cagagcctgt gggaagtctc catggtgaag tataggctga    780

ggctacctgt gaacagtacg cagtgaatgt tcatccagag ctgctgttgg cggattgtac    840

ccacggggag atgattcctc atgaagagcc tggatcccct acagaaatca aatgtgactt    900

tccgtttatc agactaaaat cagagccatc cagacagtga aacagtcacc gtggaggggg    960

gacggcgaaa aatgaaatcc aaccaagagc ggagcaacga atgcctgcct cccaagaagc   1020

gcgagatccc cgccaccagc cggtcctccg aggagaaggc cccctaccctg cccagcgaca   1080

accaccgggt ggagggcaca gcatggctcc cgggcaaccc tggtggccgg ggccacgggg   1140

gcgggaggca tgggccggca gggacctcgg tggagcttgg tttacaacag ggaataggtt   1200

tacacaaagc attgtccaca gggctggact actccccgcc cagcgctccc aggtctgtcc   1260

ccgtggccac cacgctgcct gccgcgtacg ccaccccgca gccagggacc ccggtgtccc   1320

ccgtgcagta cgctcacctg ccgcacacct tccagttcat tgggtcctcc caatacagtg   1380
```

-continued gaacctatgc cagcttcatc ccatcacagc tgatccccccc aaccgccaac cccgtcacca 1440
gtgcagtggc ctcggccgca ggggccacca ctccatccca gcgctcccag ctggaggcct 1500
attccactct gctggccaac atgggcagtc tgagccagac gccgggacac aaggctgagc 1560
agcagcagca gcagcagcag cagcagcagc agcagcatca gcatcagcag cagcagcagc 1620
agcagcagca gcagcagcag cagcagcacc tcagcagggc tccggggctc atcaccccgg 1680
ggtccccccc accagcccag cagaaccagt acgtccacat ttccagttct ccgcagaaca 1740
ccggccgcac cgcctctcct ccggccatcc ccgtccacct ccacccccac cagacgatga 1800
tcccacacac gctcaccctg ggcccccct cccaggtcgt catgcaatac gccgactccg 1860
gcagccactt tgtccctcgg gaggccacca agaaagctga gagcagccgg ctgcagcagg 1920
ccatccaggc caaggaggtc ctgaacggtg agatggagaa gagccggcgg tacgggggccc 1980
cgtcctcagc cgacctgggc ctgggcaagg caggcggcaa gtcggttcct cacccgtacg 2040
agtccaggca cgtggtggtc cacccgagcc cctcagacta cagcagtcgt gatccttcgg 2100
gggtccgggc ctctgtgatg gtcctgccca acagcaacac gcccgcagct gacctggagg 2160
tgcaacaggc cactcatcgt gaagcctccc cttctaccct caacgacaaa agtggcctgc 2220
atttagggaa gcctggccac cggtcctacg cgctctcacc ccacacggtc attcagacca 2280
cacacagtgc ttcagagcca ctcccggtgg gactgccagc cacggccttc tacgcaggga 2340
ctcaaccccc tgtcatcggc tacctgagcg gccagcagca agcaatcacc tacgccggca 2400
gcctgcccca gcacctggtg atccccggca cacagcccct gctcatcccg gtcggcagca 2460
ctgacatgga agcgtcgggg gcagccccgg ccatagtcac gtcatcccccc cagtttgctg 2520
cagtgcctca cacgttcgtc accaccgccc ttcccaagag cgagaacttc aaccctgagg 2580
ccctggtcac ccaggccgcc tacccagcca tggtgcaggc ccagatccac ctgcctgtgg 2640
tgcagtccgt ggcctccccg gcggcggctc cccctacgct gcctccctac ttcatgaaag 2700
gctccatcat ccagttggcc aacggggagc taaagaaggt ggaagactta aaaacagaag 2760
atttcatcca gagtgcagag ataagcaacg acctgaagat cgactccagc accgtagaga 2820
ggattgaaga cagccatagc ccgggcgtgg ccgtgataca gttcgccgtc ggggagcacc 2880
gagcccaggt cagcgttgaa gttttggtag agtatccttt ttttgtgttt ggacagggct 2940
ggtcatcctg ctgtccggag agaaccagcc agctctttga tttgccgtgt tccaaactct 3000
cagttgggga tgtctgcatc tcgcttaccc tcaagaacct gaagaacggc tctgttaaaa 3060
agggccagcc cgtggatccc gccagcgtcc tgctgaagca ctcaaaggcc gacggcctgg 3120
cgggcagcag acacaggtat gccgagcagg aaaacggaat caaccagggg agtgcccaga 3180
tgctctctga gaatggcgaa ctgaagtttc cagagaaaat gggattgcct gcagcgccct 3240
tcctcaccaa aatagaaccc agcaagcccg cggcaacgag gaagaggagg tggtcggcgc 3300
cagagagccg caaactggag aagtcagaag acgaaccacc tttgactctt cctaagcctt 3360
ctctaattcc tcaggaggtt aagatttgca ttgaaggccg gtctaatgta ggcaagtaga 3420
ggcagcgtgg gggaaaggaa acgtggctct ccccttatcat ttgtatccag attactgtac 3480
tgtaggctaa aataacacag tatttacatg ttatcttctt aattttaggt ttctgttcta 3540
accttgtcat tagagttaca gcaggtgtgt cgcaggagac tggtgcatat gctttttcca 3600
cgagtgtctg tcagtgagcg ggcgggagga agggcacagc aggagcggtc agggctccag 3660
gcatccccgg ggaagaaagg aacggggctt cacagtgcct gccttctcta gcggcacaga 3720
agcagccggg ggcgctgact cccgctagtg tcaggagaaa agtcccgtgg gaagggtcct 3780

-continued

```
gcaggggtgc agggttgcac gcatgtgggg gtgcacaggc gctgtggcgg cgagtgaggg   3840
tctctttttc tctgcctccc tctgcctcac tctcttgcta tcggcatggg ccggggggggt   3900
tcagagcagt gtcctcctgg ggttcccacg tgcaaaatca acatcaggaa cccagcttca   3960
gggcatcgcg gagacgcgtc agatggcaga tttggaaagt taaccattta aaagaacatt   4020
tttctctcca acatatttta caataaaagc aacttttaat tgtatagata tatatttccc   4080
cctatggggc ctgactgcac tgatatatat tttttttaaa gagcaactgc cacatgcggg   4140
atttcatttc tgctttttac tagtgcagcg atgtcaccag ggtgttgtgg tggacaggga   4200
agcccctgct gtcatggccc cacatggggt aagggggggtt gggggtgggg gagagggaga   4260
gagcgaacac ccacgctggt ttctgtgcag tgttaggaaa accaatcagg ttattgcatt   4320
gacttcactc ccaagaggta gatgcaaact gcccttcagt gagagcaaca gaagctcttc   4380
acgttgagtt tgcgaaatct ttttgtcttt gaactctagt actgtttata gttcatgact   4440
atggacaact cgggtgccac tttttttttt tttcagattc cagtgtgaca tgaggaatta   4500
gattttgaag atgagcatat attactatct ttaagcattt aaaaatactg ttcacacttt   4560
attaccaagc atcttggtct ctcattcaac aagtactgta tctcacttta aactctttgg   4620
ggaaaaaaca aaaacaaaaa aaactaagtt gctttctttt tttcaacact gtaactacat   4680
ttcagctctg cagaattgct gaagagcaag atattgaaag tttcaatgtg gtttaaaggg   4740
atgaatgtga attatgaact agtatgtgac aataaatgac caccaagtac tacctgacgg   4800
gaggcacttt tcactttgat gtctgagaat cagttcaagg catatgcaga gttggcagag   4860
aaactgagag aaaagggatg gagaagagaa tactcatttt tgtccagtgt ttttcttttt   4920
aagatgaact tttaaagaac cttgcgattt gcacatattg agtttataac ttgtgtgata   4980
ttcctgcagt ttttatccaa taacattgtg ggaaaggttt gggggactga acgagcataa   5040
ataaatgtag caaaatttct ttctaacctg cctaaactct aggccatttt ataaggttat   5100
gttcctttga aaattcattt tggtcttttt accacatctg tcacaaaaag ccaggtctta   5160
gcgggctctt agaaactctg agaattttct tcagattcat tgagagagtt ttccataaag   5220
acatttatat atgtgagcaa gatttttttt aaacaattac tttattattg ttgttattaa   5280
tgttattttc agaatggctt tttttttttct attcaaaatc aaatcgagat ttaatgtttg   5340
gtacaaaccc agaaagggta tttcatagtt tttaaacctt tcattcccag agatccgaaa   5400
tatcatttgt gggttttgaa tgcatcttta aagtgcttta aaaaaaagtt ttataagtag   5460
ggagaaattt ttaaatattc ttacttggat ggctgcaact aaactgaaca aatacctgac   5520
ttttctttta ccccattgaa aatagtactt tcttcgtttc acaaattaaa aaaaaaatct   5580
ggtatcaacc cacattttgg ctgtctagta ttcatttaca tttagggttc accaggacta   5640
atgattttta taaaccgttt tctggggtgt accaaaaaca tttgaatagg tttagaatag   5700
ctagaatagt tccttgactt tcctcgaatt tcattaccct ctcagcatgc ttgcagagag   5760
ctgggtgggc tcattcttgc agtcatactg cttatttagt gctgtatttt ttaaacgttt   5820
ctgttcagag aacttgctta atcttccata tattctgctc agggcacttg caattattag   5880
gttttgtttt tctttttgtt ttttagcctt tgatggtaag aggaatacgg gctgccacat   5940
agactttgtt ctcattaata tcactattta caactcatgt ggactcagaa aaacacacac   6000
caccttttgg cttacttcga gtattgaatt gactggatcc actaaaccaa cactaagatg   6060
ggaaaacaca catggtttgg agcaatagga acatcatcat aatttttgtg gttctatttc   6120
```

-continued

```
aggtatagga attataaaat aattggttct ttctaaacac ttgtcccatt tcattctctt   6180
gcttttttag catgtgcaat actttctgtg ccaatagagt ctgaccagtg tgctatatag   6240
ttaaagctca ttccctttg gctttttcct tgtttggttg atcttcccca ttctggccag    6300
agcagggctg gagggaagga gccaggaggg agagagcctc ccacctttcc cctgctgcgg   6360
atgctgagtg ctggggcggg gagccttcag gagccccgtg cgtctgccgc cacgttgcag   6420
aaagagccag ccaaggagac ccgggggagg aaccgcagtg tcccctgtca ccacacggaa   6480
tagtgaatgt ggagtgtgga gaggaaggag gcagattcat ttctaagacg cactctggag   6540
ccatgtagcc tggagtcaac ccattttcca cggtcttttc tgcaagtggg caggcccctc   6600
ctcggggtct gtgtccttga gacttggagc cctgcctctg agcctggacg ggaagtgtgg   6660
cctgttgtgt gtgtgcgttc tgagcgtgtt ggccagtggc tgtggagggg accacctgcc   6720
acccacggtc accactccct tgtggcagct ttctcttcaa ataggaagaa cgcacagagg   6780
gcaggagcct cctgtttgca gacgttggcg ggccccgagg ctcccagagc agcctctgtc   6840
accgcttctg tgtagcaaac attaacgatg acaggggtag aaattcttcg gtgccgttca   6900
gcttacaagg atcagccatg tgcctctgta ctatgtccac tttgcaatat ttaccgacag   6960
ccgtcttttg ttctttcttt cctgttttcc atttttaaac tagtaacagc aggccttttg   7020
cgtttacaat ggaacacaat caccaagaaa ttagtcaggg cgaaaagaaa aaaataatac   7080
tattaataag aaaccaacaa acaagaacct ctctttctag ggatttctaa atatataaaa   7140
tgactgttcc ttagaatgtt taacttaaga attatttcag tttgtctggg ccacactggg   7200
gcagaggggg gagggaggga tacagagatg gatgccactt acctcagatc ttttaaagtg   7260
gaaatccaaa ttgaattttc atttggactt tcaggataat tttctatgtt ggtcaacttt   7320
tcgttttccc taactcaccc agtttagttt gggatgattt gatttctgtt gttgttgatc   7380
ccatttctaa cttggaattg tgagcctcta tgttttctgt taggtgagtg tgttgggttt   7440
tttcccccca ccaggaagtg gcagcatccc tccttctccc ctaaagggac tctgcggaac   7500
ctttcacacc tctttctcag ggacggggca ggtgtgtgtg tggtacactg acgtgtccag   7560
aagcagcact ttgactgctc tggagtaggg ttgtacaatt tcaaggaatg tttggatttc   7620
ctgcatcttg tggattactc cttagatacc gcatagattg caatataatg ctgcatgttc   7680
aagatgaaca gtagctccta gtaatcataa aatccactct ttgcacagtt tgatctttac   7740
tgaaatatgt tgccaaaatt tatttttgtt gttgtagctc tggattttgt tttgttttgt   7800
tttttaagga aacgattgac aatacccttt aacatctgtg actactaagg aaacctattt   7860
ctttcataga gagaaaaatc tccaatgctt ttgaagacac taataccgtg ctatttcaga   7920
tatgggtgag gaagcagagc tctcggtacc gaaggccggg cttcttgagc tgtgttggtt   7980
gtcatggcta ctgtttcatg aaccacaagc agctcaacag actggtctgt tgccttctga   8040
aacccttttgc acttcaattt gcaccaggtg aaaacagggc cagcagactc catggcccaa   8100
ttcggtttct tcggtggtga tgtgaaagga gagaattaca cttttttttt ttttaagtgg   8160
cgtggaggcc tttgcttcca catttgtttt taacccagaa tttctgaaat agagaattta   8220
agaacacatc aagtaataaa tatacagaga atatactttt ttataaagca catgcatctg   8280
ctattgtgtt gggttggttt cctctctttt ccacggacag tgttgtgttt ctggcatagg   8340
gaaactccaa acaacttgca cacctctact ccggagctga gatttctttt acatagatga   8400
cctcgcttca aatacgttac cttactgatg ataggatctt ttcttgtagc actatacctt   8460
gtgggaattt ttttttaaat gtacacctga tttgagaagc tgaagaaaac aaaattttga   8520
```

agcactcact ttgaggagta caggtaatgt tttaaaaaat tgcacaaaag aaaaatgaat 8580
gtcgaaatga ttcattcagt gtttgaaaga tatggctctg ttgaaacaat gagtttcata 8640
ctttgtttgt aaaaaaaaaa aagcagagaa gggttgaaag ttacatgttt ttttgtatat 8700
agaaatttgt catgtctaaa tgatcagatt tgtatggtta tggcctggaa gaattactac 8760
gtaaaaggct cttaaactat acctatgctt attgttattt ttgttacata tagccctcgt 8820
ctgagggagg ggaactcggt attctgcgat ttgagaatac tgttcattcc tatgctgaaa 8880
gtacttctct gagctccctt cttagtctaa actcttaagc cattgcaact tctttttctt 8940
cagagatgat gtttgacatt ttcagcactt cctgttccta taaacccaaa gaatataatc 9000
ttgaacacga agtgtttgta acaagggatc caggctacca atcaaacagg actcattatg 9060
gggacaaaaa aaaaaattat ttcaccttct ttccccccac acctcattta aatgggggga 9120
gtaaaaacat gatttcaatg taaatgcctc attttatttt agttttattt tgatttttat 9180
ttaatataaa gaggccagaa taaatacgga gcatcttctc agaatagtat tcctgtccaa 9240
aaatcaagcc ggacagtgga aactggacag ctgtggggat attaagcacc cccacttaca 9300
attcttaaat tcagaatctc gtcccctccc ttctcgttga aggcaactgt tctggtagct 9360
aactttctcc tgtgtaatgg cgggagggaa caccggcttc agtttttcat gtccccatga 9420
cttgcataca aatggttcaa ctgtattaaa attaagtgca tttggccaat aggtagtatc 9480
tatacaataa caacaatctc taagaatttc cataactttt cttatctgaa aggactcaag 9540
tcttccactg cagatacatt ggaggcttca cccacgtttt ctttcccttt agtttgtttg 9600
ctgtctggat ggccaatgag cctgtctcct tttctgtggc caatctgaag gccttcgttg 9660
gaagtgttgt ttacagtaat ccttaccaag ataacatact gtcctccaga ataccaagta 9720
ttaggtgaca ctagctcaag ctgttgtctt cagagcagtt accaagaagc tcggtgcaca 9780
ggttttctct ggttcttaca ggaaccacct actctttcag ttttctggcc caggagtggg 9840
gtaaatcctt tagttagtgc atttgaactt gatacctgtg cattcagttc tgtgaatact 9900 gcccttttttg gcggggtttc ctcatctccc cagcctgaac tgctcaactc taaacccaaa 9960
ttagtgtcag ccgaaaggag gtttcaagat agtcctgtca gtatttgtgg tgaccttcag 10020
attagacagt cttcatttcc agccagtgga gtcctggctc cagagccatc tctgagactc 10080
gtactactgg atgttttaat atcagatcat tacccaccat atgcctccca caggccaagg 10140
gaaaacagac accagaactt gggttgaggg cactaccaga ctgacatggc cagtacagag 10200
gagaactagg gaaggaatga tgttttgcac cttattgaaa agaaaatttt aagtgcatac 10260
ataatagtta agagctttta ttgtgacagg agaacttttt tccatatgcg tgcatactct 10320
ctgtaattcc agtgtaaaat attgtacttg cactagcttt tttaaacaaa tattaaaaaa 10380
tggaagaatt catattctat tttctaatcg tggtgtgtct atttgtagga tacactcgag 10440
tctgtttatt gaattttatg gtccctttct ttgatggtgc ttgcaggttt tctaggtaga 10500
aattatttca ttattataat aaaacaatgt ttgattcaaa atttgaacaa aattgtttta 10560
aataaattgt ctgtatacca gtacaagttt attgtttcag tatactcgta ctaataaaat 10620
aacagtgcca attgca 10636

<210> SEQ ID NO 82
<211> LENGTH: 4712
<212> TYPE: DNA
<213> ORGANISM: Homo sapiens

<400> SEQUENCE: 82

```
acccccgaga aagcaaccca gcgcgccgcc cgctcctcac gtgtccctcc cggccccggg      60
gccacctcac gttctgcttc cgtctgaccc ctccgacttc cggtaaagag tccctatccg     120
cacctccgct cccacccggc gcctcggcgc gcccgccctc cgatgcgctc agcggccgca     180
gctcctcgga gtcccgcggt ggccaccgag tctcgccgct tcgccgcagc caggtggccc     240
gggtggcgct cgctccagcg gccggcgcgg cggagcgggc ggggcggcgg tggcgcggcc     300
ccgggaccgt atccctccgc cgcccctccc ccgcccggcc ccggcccccc tccctcccgg     360
cagagctcgc ctccctccgc ctcagactgt tttggtagca acggcaacgg cggcggcgcg     420
tttcggcccg gctcccggcg gctccttggt ctcggcgggc ctccccgccc cttcgtcgtc     480
ctccttctcc ccctcgccag cccgggcgcc cctccggccg cgccaacccg cgcctccccg     540
ctcggcgccc gcgcgtcccc gccgcgttcc ggcgtctcct tggcgcgccc ggctcccggc     600
tgtccccgcc cggcgtgcga gccggtgtat gggcccctca ccatgtcgct gaagccccag     660
cagcagcagc agcagcagca gcagcagcag cagcagcaac agcagcagca gcagcagcag     720
cagcagccgc cgcccgcggc tgccaatgtc cgcaagcccg gcggcagcgg ccttctagcg     780
tcgcccgccg ccgcgccttc gccgtcctcg tcctcggtct cctcgtcctc ggccacggct     840
ccctcctcgg tggtcgcggc gacctccggc ggcgggaggc ccggcctggg cagaggtcga     900
aacagtaaca aaggactgcc tcagtctacg atttcttttg atggaatcta tgcaaatatg     960
aggatggttc atatacttac atcagttgtt ggctccaaat gtgaagtaca agtgaaaaat    1020
ggaggtatat atgaaggagt ttttaaaact tacagtccga agtgtgattt ggtacttgat    1080
gccgcacatg agaaaagtac agaatccagt tcggggccga aacgtgaaga aataatggag    1140
agtattttgt tcaaatgttc agactttgtt gtggtacagt ttaaagatat ggactccagt    1200
tatgcaaaaa gagatgcttt tactgactct gctatcagtg ctaaagtgaa tggcgaacac    1260
aaagagaagg acctggagcc ctgggatgca ggtgaactca cagccaatga ggaacttgag    1320
gctttggaaa atgacgtatc taatggatgg gatcccaatg atatgtttcg atataatgaa    1380
gaaaattatg gtgtagtgtc tacgtatgat agcagtttat cttcgtatac agtgccctta    1440
gaaagagata actcagaaga atttttaaaa cgggaagcaa gggcaaacca gttagcagaa    1500
gaaattgagt caagtgccca gtacaaagct cgagtggccc tggaaaatga tgataggagt    1560
gaggaagaaa aatacacagc agttcagaga aattccagtg aacgtgaggg gcacagcata    1620
aacactaggg aaaataaata tattcctcct ggacaaagaa atagagaagt catatcctgg    1680
ggaagtggga gacagaattc accgcgtatg ggccagcctg gatcgggctc catgccatca    1740
agatccactt ctcacacttc agatttcaac ccgaattctg gttcagacca aagagtagtt    1800
aatggaggtg ttccctggcc atcgccttgc ccatctcctt cctctcgccc accttctcgc    1860
taccagtcag gtcccaactc tcttccacct cgggcagcca cccctacacg gccgccctcc    1920
aggccccccct cgcggccatc cagacccccg tctcacccct ctgctcatgg ttctccagct    1980
cctgtctcta ctatgcctaa acgcatgtct tcagaagggc ctccaaggat gtccccaaag    2040
gcccagcgac atcctcgaaa tcacagagtt tctgctggga ggggttccat atccagtggc    2100
ctagaatttg tatcccacaa cccacccagt gaagcagcta ctcctccagt agcaaggacc    2160
agtccctcgg ggggaacgtg gtcatcagtg gtcagtgggg ttccaagatt atcccctaaa    2220
actcatagac ccaggtctcc cagacagaac agtattggaa atacccccag tgggccagtt    2280
cttgcttctc cccaagctgg tattattcca actgaagctg ttgccatgcc tattccagct    2340
```

gcatctccta cgcctgctag tcctgcatcg aacagagctg ttaccccttc tagtgaggct 2400
aaagattcca ggcttcaaga tcagaggcag aactctcctg cagggaataa agaaaatatt 2460
aaacccaatg aaacatcacc tagcttctca aaagctgaaa acaaaggtat atcaccagtt 2520
gtttctgaac atagaaaaca gattgatgat ttaaagaaat ttaagaatga ttttaggtta 2580
cagccaagtt ctacttctga atctatggat caactactaa acaaaaatag agagggagaa 2640
aaatcaagag atttgatcaa agacaaaatt gaaccaagtg ctaaggattc tttcattgaa 2700
aatagcagca gcaactgtac cagtggcagc agcaagccga atagccccag catttcccct 2760
tcaatactta gtaacacgga gcacaagagg ggacctgagg tcacttccca aggggttcag 2820
acttccagcc cagcatgtaa acaagagaaa gacgataagg aagagaagaa agacgcagct 2880
gagcaagtta ggaaatcaac attgaatccc aatgcaaagg agttcaaccc acgttccttc 2940
tctcagccaa agccttctac taccccaact tcacctcggc ctcaagcaca acctagccca 3000
tctatggtgg gtcatcaaca gccaactcca gtttatactc agcctgtttg ttttgcacca 3060
aatatgatgt atccagtccc agtgagccca ggcgtgcaac ctttataccc aatacctatg 3120
acgcccatgc cagtgaatca agccaagaca tatagagcag taccaaatat gccccaacag 3180
cggcaagacc agcatcatca gagtgccatg atgcacccag cgtcagcagc gggcccaccg 3240
attgcagcca ccccaccagc ttactccacg caatatgttg cctacagtcc tcagcagttc 3300
ccaaatcagc cccttgttca gcatgtgcca cattatcagt ctcagcatcc tcatgtctat 3360
agtcctgtaa tacagggtaa tgctagaatg atggcaccac caacacacgc ccagcctggt 3420
ttagtatctt cttcagcaac tcagtacggg gctcatgagc agacgcatgc gatgtatgca 3480
tgtcccaaat taccatacaa caaggagaca agcccttctt tctactttgc catttccacg 3540
ggctcccttg ctcagcagta tgcgcaccct aacgctaccc tgcacccaca tactccacac 3600
cctcagcctt cagctacccc cactggacag cagcaaagcc aacatggtgg aagtcatcct 3660
gcacccagtc ctgttcagca ccatcagcac caggccgccc aggctctcca tctggccagt 3720
ccacagcagc agtcagccat ttaccacgcg gggcttgcgc caactccacc ctccatgaca 3780
cctgcctcca acacgcagtc gccacagaat agtttcccag cagcacaaca gactgtcttt 3840
acgatccatc cttctcacgt tcagccggcg tataccaacc caccccacat ggcccacgta 3900
cctcaggctc atgtacagtc aggaatggtt ccttctcatc caactgccca tgcgccaatg 3960
atgctaatga cgacacagcc acccggcggt ccccaggccg ccctcgctca aagtgcacta 4020
cagcccattc cagtctcgac aacagcgcat ttccccctata tgacgcaccc ttcagtacaa 4080
gcccaccacc aacagcagtt gtaaggctgc cctggaggaa ccgaaaggcc aaattccctc 4140
ctcccttcta ctgcttctac caactggaag cacagaaaac tagaatttca tttattttgt 4200
ttttaaaata tatatgttga tttcttgtaa catccaatag gaatgctaac agttcacttg 4260
cagtggaaga tacttggacc gagtagaggc atttaggaac ttgggggcta ttccataatt 4320
ccatatgctg tttcagagtc ccgcaggtac cccagctctg cttgccgaaa ctggaagtta 4380
tttatttttt aataaccctt gaaagtcatg aacacatcag ctagcaaaag aagtaacaag 4440
agtgattctt gctgctatta ctgctaaaaa aaaaaaaaaa aaaaaatcaa gacttggaac 4500
gcccttttac taaacttgac aaagtttcag taaattctta ccgtcaaact gacggattat 4560
tatttataaa tcaagtttga tgaggtgatc actgtctaca gtggttcaac ttttaagtta 4620
agggaaaaac ttttactttg tagataatat aaaataaaaa cttaaaaaaa atttaaaaaa 4680

-continued

```
taaaaaaagt tttaaaaact gaaaaaaaaa aa                                    4712


<210> SEQ ID NO 83
<211> LENGTH: 6923
<212> TYPE: DNA
<213> ORGANISM: Homo sapiens

<400> SEQUENCE: 83

gagaggggca gggggcggag ctggaggggg tggttcggcg tgggggccgt tggctccaga      60

caaataaaca tggagtccat cttccacgag aaacaagaag gctcactttg tgctcaacat     120

tgcctgaata acttattgca aggagaatat tttagccctg tggaattatc ctcaattgca     180

catcagctgg atgaggagga gaggatgaga atggcagaag gaggagttac tagtgaagat     240

tatcgcacgt ttttacagca gccttctgga aatatggatg acagtggttt tttctctatt     300

caggttataa gcaatgcctt gaaagtttgg ggtttagaac taatcctgtt caacagtcca     360

gagtatcaga ggctcaggat cgatcctata aatgaaagat catttatatg caattataag     420

gaacactggt ttacagttag aaaattagga aaacagtggt ttaacttgaa ttctctcttg     480

acgggtccag aattaatatc agatacatat cttgcacttt tcttggctca attacaacag     540

gaaggttatt ctatatttgt cgttaagggt gatctgccag attgcgaagc tgaccaactc     600

ctgcagatga ttagggtcca acagatgcat cgaccaaaac ttattggaga agaattagca     660

caactaaaag agcaaagagt ccataaaaca gacctggaac gagtgttaga agcaaatgat     720

ggctcaggaa tgttagacga agatgaggag gatttgcaga gggctctggc actaagtcgc     780

caagaaattg acatggaaga tgaggaagca gatctccgca gggctattca gctaagtatg     840

caaggtagtt ccagaaacat atctcaagat atgacacaga catcaggtac aaatcttact     900

tcagaagagc ttcggaagag acgagaagcc tactttgaaa aacagcagca aaagcagcaa     960

cagcagcagc agcagcagca gcagggggac ctatcaggac agagttcaca tccatgtgaa    1020

aggccagcca ccagttcagg agcacttggg agtgatctag gtgatgctat gagtgaagaa    1080

gacatgcttc aggcagctgt gaccatgtct ttagaaactg tcagaaatga tttgaaaaca    1140

gaaggaaaaa aataatacct ttaaaaaata atttagatat tcatactttc caacattatc    1200

ctgtgtgatt acagcatagg gtccactttg gtaatgtgtc aaagagatga ggaaataaga    1260

cttttagcgg tttgcaaaca aaatgatggg aaagtggaac aatgcgtcgg ttgtaggact    1320

aaataatgat cttccaaata ttagccaaag aggcattcag caattaaaga catttaaaat    1380

agttttctaa atgtttcttt ttcttttttg agtgtgcaat atgtaacatg tctaaagtta    1440

gggcattttt cttggatctt tttgcagact agctaattag ctctcgcctc aggctttttc    1500

catatagttt gttttctttt tctgtcttgt aggtaagttg gctcacatca tgtaatagtg    1560

gctttcattt cttattaacc aaattaacct ttcaggaaag tatctctact ttcctgatgt    1620

tgataatagt aatggttcta gaaggatgaa cagttctccc ttcaactgta taccgtgtgc    1680

tccagtgttt tcttgtgttg ttttctctga tcacaacttt tctgctacct ggttttcatt    1740

attttcccac aattcttttg aaagatggta atcttttctg aggtttagcg ttttaagccc    1800

tacgatggga tcattatttc atgactggtg cgttcctaaa ctctgaaatc agccttgcac    1860

aagtacttga gaataaatga gcattttttta aaatgtgtga gcatgtgctt tcccagatgc    1920

tttatgaatg tcttttcact tatatcaaaa ccttacagct ttgttgcaac cccttcttcc    1980

tgcgccttat tttttccttt cttctccaat tgagaaaact aggagaagca tagtatgcag    2040

gcaagtctcc ttctgttaga agactaaaca tacgtaccca ccatgaatgt atgatacatg    2100
```

-continued

```
aaatttggcc ttcaatttta atagcagttt tattttattt tttctcctat gactggagct   2160
ttgtgttctc tttacagttg agtcatggaa tgtaggtgtc tgcttcacat cttttagtag   2220
gtatagcttg tcaaagatgg tgatctggaa catgaaaata atttactaat gaaaatatgt   2280
ttaaatttat actgtgattt gacacttgca tcatgtttag atagcttaag aacaatggaa   2340
gtcacagtac ttagtggatc tataaataag aaagtccata gttttgataa atattctctt   2400
taattgagat gtacagagag tttcttgctg ggtcaatagg atagtatcat tttggtgaaa   2460
accatgtctc tgaaattgat gttttagttt cagtgttccc tatccctcat tctccatctc   2520
cttttgaagc tcttttgaat gttgaattgt tcataagcta aaatccaaga aatttcagct   2580
gacaacttcg aaaattataa tatggtatat tgccctcctg gtgtgtggct gcacacattt   2640
tatcagggaa agtttttttga tctaggattt attgctaact aactgaaaag agaagaaaaa   2700
atatctttta tttatgatta taaaatagct ttttcttcga tataacagat tttttaagtc   2760
attattttgt gccaatcagt tttctgaagt ttcccttaca caaaaggata gctttatttt   2820
aaaatctaaa gtttctttta atagttaaaa atgtttcaga agaattataa aactttaaaa   2880
ctgcaaggga tgttggagtt tagtactact ccctcaagat ttaaaaagct aaatatttta   2940
agactgaaca tttatgttaa ttattaccag tgtgtttgtc atattttcca tggatatttg   3000
ttcattacct ttttccattg aaaagttaca ttaaactttt catacacttg aattgatgag   3060
ctacctaata taaaaatgag aaaaccaata tgcattttaa agttttaact ttagagttta   3120
taaagttcat atataccctta gttaaagcac ttaagaaaat atggcatgtt tgacttttag   3180
ttcctagaga gtttttgttt ttgtttttgt ttttttttga gacggagtct tgctatgtct   3240
cccaggctgg agggcagtgg catgatctcg gctcactaca acttccacct cccgggttca   3300
agcaattctc ctgcctcagc ctccagagta gctgggatta caggcgccca ccaccacacc   3360
cggcagattt ttgtattttt ggtagagacg cggtttcatc atgtttggcc aggctggtct   3420
cgaactcctg acctcaggtg atccgcctgc cttggcctcc caaagtgttg ggattacagg   3480
catgagccac tgcgcctggc cagctagaga gtttttaaag cagagctgag cacacactgg   3540
atgcgtttga atgtgtttgt gtagtttgtt gtgaaattgt tacatttagc aggcagatcc   3600
agaagcacta gtgaactgtc atcttggtgg ggttggctta aatttaattg actgtttaga   3660
ttccatttct taattgattg gccagtatga aaagatgcca gtgcaagtaa ccatagtatc   3720
aaaaaagtta aaaattattc aaagctatag tttatacatc aggtactgcc atttactgta   3780
aaccacctgc aagaaagtca ggaacaacta aattcacaag aactgtcctg ctaagaagtg   3840
tattaaagat ttccattttg ttttactaat tgggaacatc ttaatgttta atatttaaac   3900
tattggtatc atttttctaa tgtataattt gtattactgg gatcaagtat gtacagtggt   3960
gatgctagta gaagtttaag ccttggaaat accactttca tattttcaga tgtcatggat   4020
ttaatgagta atttatgttt ttaaaattca gaatagttaa tctctgatct aaaaccatca   4080
atctatgttt tttacggtaa tcatgtaaat atttcagtaa tataaactgt ttgaaaaggc   4140
tgctgcaggt aaactctata ctaggatctt ggccaaataa tttacaattc acagaatatt   4200
ttatttaagg tggtgctttt ttttttgtc cttaaaactt gatttttctt aactttattc   4260
atgatgccaa agtaaatgag gaaaaaaact caaaaccagt tgagtatcat tgcagacaaa   4320
actaccagta gtccatattg tttaatatta agttgaataa aataaatttt atttcagtca   4380
gagcctaaat cacattttga ttgtctgaat ttttgatact atttttaaaa tcatgctagt   4440
```

ggcggctggg cgtggtagct cacgcctgta atcccagcat tttgggaggc cgaagtgggt 4500
ggatcacgag gtcgggagtt cgagaccagc ttggccaaaa tggtgaaacc ccatctgtac 4560
taaaaactac aaaaattagc tgggcgcggt ggcaggtgcc tgtaatccca gctacctggg 4620
agtctgaggc aggagaattg cttgaaccct ggcgacagag gatgcagtga gccaagatgg 4680
tgccactgta ctccagactg ggcgacagag tgagactctg tctcaaaaaa aaaaaaaaaa 4740
tcatgctagt gccaagagct actaaattct taaaaccggc ccattggacc tgtacagata 4800
aaaaatagat tcagtgcata atcaaaatat gataatttta aaatcttaag tagaaaaata 4860
aatcttgatg ttttaaattc ttacgaggat tcaatagtta atattgatga tctcccggct 4920
gggtgcagtg gctcacgcct gtaatcccag cagttctgga ggctgaggtg ggcgaatcac 4980
ttcaggccag gagttcaaga ccagtctggg caacatggtg aaacctcgtt tctactaaaa 5040
atacaaaaat tagccgggcg tggttgcaca cacttgtaat cccagctact caggaggcta 5100
agaatcgcat gagcctagga ggcagaggtt gcagagtgcc aagggctcac cactgcattc 5160
cagcctgccc aacagagtga gacactgttt ctgaaaaaaa aaaatatata tatatatata 5220
tatatgtgtg tatatatata tgtatatata tatgacttcc tattaaaaac tttatcccag 5280
tcgggggcag tggctcacgc ctgtaatccc aacactttgg gaggctgagg caggtggatc 5340
acctgaagtc cggagtttga gaccagcctg gccaacatgg tgaaacccca tctctactaa 5400
aaatacaaaa cttaagccag gtatggtggc gggcacctgt aatcccagtt acttgggagg 5460
ctgaggcagg agaatcgttt aaacccagga ggtggaggtt gcagtgagct gagatcgtgc 5520
cattgcactc tagcctgggc aacaagagta aaactccatc ttaaaggttt gtttgttttt 5580
ttttaatccg gaaacgaaga ggcgttgggc cgctattttc tttttctttc tttctttctt 5640
tctttttttt tttttctgag acggagtcta gctctgctgc ccaggctgga gtacaatgac 5700
acgatgttgg ctcactgcaa cctccacctc ctgggttcaa gcgattctcc tgcctcagcc 5760
tcccaagtac ctgggattac aggcacctgc cactacacct ggcgaatatt tgtttttttt 5820
agtagagacg ggcttttacc atgttaggct ggtctcaaac tcctgacctc aggtgatctg 5880
cctgccttgg cctcccaaag tgctgggatt acaggtgcag gccaccacac ccggccttgg 5940
gccactgttt tcaaagtgaa ttgtttgttg tatcgagtcc ttaagtatgg atatatatgt 6000
gaccctaatt aagaactacc agattggatc aactaatcat gtcagcaatg taaataactt 6060
tatttttcat attcaaaata aaaactttct tttatttctg gcccctttat aaccagcatc 6120
tttttgcttt aaaaaatgac ctggctttgt atttttttag tcttaaacat aataaaaata 6180
tttttgttct aatttgcttt catgagtgaa gattattgac atcgttggta aattctagaa 6240
ttttgatttt gtttttttaat ttgaagaaaa tctttgctat tattattttt tccaagtggt 6300
ctggcatttt aagaattagt gctaataacg taacttctaa atttgtcgta attggcatgt 6360
ttaatagcat atcaaaaaac attttaagcc tgtggattca tagacaaagc aatgagaaac 6420
attagtaaaa tataaatgga tattcctgat gcatttagga agctctcaat tgtctcttgc 6480
atagttcaag gaatgttttc tgaatttttt taatgctttt tttttttttg aaagaggaaa 6540
acatacattt ttaaatgtga ttatctaatt tttacaacac tgggctatta ggaataactt 6600
tttaaaaatt actgttctgt ataaatattt gaaattcaag tacagaaaat atctgaaaca 6660
aaaagcattg ttgtttggcc atgatacaag tgcactgtgg cagtgccgct tgctcaggac 6720
ccagccctgc agcccttctg tgtgtgctcc ctcgttaagt tcatttgctg ttattacaca 6780
cacaggcctt cctgtctggt cgttagaaaa gccgggcttc caaagcactg ttgaacacag 6840
gattctgttg ttagtgtgga tgttcaatga gttgtatttt aaatatcaaa gattattaaa 6900
taaagataat gtttgctttt cta 6923

<210> SEQ ID NO 84
<211> LENGTH: 8646
<212> TYPE: DNA
<213> ORGANISM: Homo sapiens

<400> SEQUENCE: 84
gatgtcccga gctgctatcc ccggctcggc ccgggcagcc gccttctgag cccccgaccc 60
gaggcgccga gccgccgccg cccgatgggc tgggccgtgg agcgtctccg cagtcgtagc 120
tccagccgcc gcgctcccag ccccggcagc ctcagcatca gcggcggcgg cggcggcggc 180
ggcgtcttcc gcatcgttcg ccgcagcgta acccggagcc ctttgctctt tgcagaatgg 240
cccgcttcgg agacgagatg ccggcccgct acgggggagg aggctccggg gcagccgccg 300
gggtggtcgt gggcagcgga ggcgggcgag gagccggggg cagccggcag ggcgggcagc 360
ccggggcgca aaggatgtac aagcagtcaa tggcgcagag agcgcggacc atggcactct 420
acaaccccat ccccgtccga cagaactgcc tcacggttaa ccggtctctc ttcctcttca 480
gcgaagacaa cgtggtgaga aaatacgcca aaaagatcac cgaatggcct ccctttgaat 540
atatgatttt agccaccatc atagcgaatt gcatcgtcct cgcactggag cagcatctgc 600
ctgatgatga caagaccccg atgtctgaac ggctggatga cacagaacca tacttcattg 660 gaatttttttg tttcgaggct ggaattaaaa tcattgccct tgggtttgcc ttccacaaag 720
gctcctactt gaggaatggc tggaatgtca tggactttgt ggtggtgcta acgggcatct 780
tggcgacagt tgggacggag tttgacctac ggacgctgag ggcagttcga gtgctgcggc 840
cgctcaagct ggtgtctgga atcccaagtt tacaagtcgt cctgaagtcg atcatgaagg 900
cgatgatccc tttgctgcag atcggcctcc tcctattttt tgcaatcctt atttttgcaa 960
tcatagggtt agaattttat atgggaaaat ttcataccac ctgctttgaa gaggggacag 1020
atgacattca gggtgagtct ccggctccat gtgggacaga agagcccgcc cgcacctgcc 1080
ccaatgggac caaatgtcag ccctactggg aagggcccaa caacgggatc actcagttcg 1140
acaacatcct gtttgcagtg ctgactgttt tccagtgcat aaccatggaa gggtggactg 1200
atctcctcta caatagcaac gatgcctcag ggaacacttg gaactggttg tacttcatcc 1260
ccctcatcat catcggctcc ttttttatgc tgaaccttgt gctgggtgtg ctgtcagggg 1320
agtttgccaa agaaagggaa cgggtggaga accggcgggc ttttctgaag ctgaggcggc 1380
aacaacagat tgaacgtgag ctcaatgggt acatggagtg gatctcaaaa gcagaagagg 1440
tgatcctcgc cgaggatgaa actgacgggg agcagaggca tccctttgat ggagctctgc 1500
ggagaaccac cataaagaaa agcaagacag atttgctcaa ccccgaagag gctgaggatc 1560
agctggctga tatagcctct gtgggttctc ccttcgcccg agccagcatt aaaagtgcca 1620
agctggagaa ctcgaccttt tttcacaaaa aggagaggag gatgcgtttc tacatccgcc 1680
gcatggtcaa aactcaggcc ttctactgga ctgtactcag tttggtagct ctcaacacgc 1740
tgtgtgttgc tattgttcac tacaaccagc ccgagtggct ctccgacttc ctttactatg 1800
cagaattcat tttcttagga ctctttatgt ccgaaatgtt tataaaaatg tacgggcttg 1860
ggacgcggcc ttacttccac tcttccttca actgctttga ctgtggggtt atcattggga 1920
gcatcttcga ggtcatctgg gctgtcataa aacctggcac atcctttgga atcagcgtgt 1980
tacgagccct caggttattg cgtattttca aagtcacaaa gtactgggca tctctcagaa 2040
acctggtcgt ctctctcctc aactccatga agtccatcat cagcctgttg tttctccttt 2100
tcctgttcat tgtcgtcttc gcccttttgg gaatgcaact cttcggcggc cagtttaatt 2160
tcgatgaagg gactcctccc accaacttcg atacttttcc agcagcaata atgacggtgt 2220
ttcagatcct gacgggcgaa gactggaacg aggtcatgta cgacgggatc aagtctcagg 2280
ggggcgtgca gggcggcatg gtgttctcca tctatttcat tgtactgacg ctctttggga 2340
actacaccct cctgaatgtg ttcttggcca tcgctgtgga caatctggcc aacgcccagg 2400
agctcaccaa ggtggaggcg gacgagcaag aggaagaaga agcagcgaac cagaaacttg 2460
ccctacagaa agccaaggag gtggcagaag tgagtcctct gtccgcggcc aacatgtcta 2520
tagctgtgaa agagcaacag aagaatcaaa agccagccaa gtccgtgtgg gagcagcgga 2580
ccagtgagat gcgaaagcag aacttgctgg ccagccggga ggccctgtat aacgaaatgg 2640
acccggacga gcgctggaag gctgcctaca cgcggcacct gcggccagac atgaagacgc 2700
acttggaccg gccgctggtg gtggacccgc aggagaaccg caacaacaac accaacaaga 2760
gccgggcggc cgagcccacc gtggaccagc gcctcggcca gcagcgcgcc gaggacttcc 2820
tcaggaaaca ggcccgctac cacgatcggg cccgggaccc cagcggctcg gcgggcctgg 2880
acgcacggag gccctgggcg ggaagccagg aggccgagct gagccgggag ggaccctacg 2940
gccgcgagtc ggaccaccac gcccgggagg gcagcctgga gcaacccggg ttctgggagg 3000
gcgaggccga gcgaggcaag gccggggacc cccaccggag gcacgtgcac cggcaggggg 3060
gcagcaggga gagccgcagc gggtccccgc gcacgggcgc ggacggggag catcgacgtc 3120
atcgcgcgca ccgcaggccc ggggaggagg gtccggagga caaggcggag cggagggcgc 3180
ggcaccgcga gggcagccgg ccggcccggg gcggcgaggg cgagggcgag ggccccgacg 3240
ggggcgagcg caggagaagg caccggcatg gcgctccagc cacgtacgag ggggacgcgc 3300
ggagggagga caaggagcgg aggcatcgga ggaggaaaga gaaccagggc tccggggtcc 3360
ctgtgtcggg ccccaacctg tcaaccaccc ggccaatcca gcaggacctg ggccgccaag 3420
acccacccct ggcagaggat attgacaaca tgaagaacaa caagctggcc accgcggagt 3480
cggccgctcc ccacggcagc cttggccacg ccggcctgcc ccagagccca gccaagatgg 3540
gaaacagcac cgaccccggc cccatgctgg ccatccctgc catggccacc aacccccaga 3600
acgccgccag ccgccggacg cccaacaacc cggggaaccc atccaatccc ggccccccca 3660
agacccccga gaatagcctt atcgtcacca accccagcgg cacccagacc aattcagcta 3720
agactgccag gaaacccgac cacaccacag tggacatccc cccagcctgc ccaccccccc 3780
tcaaccacac cgtcgtacaa gtgaacaaaa acgccaaccc agacccactg ccaaaaaaag 3840
aggaagagaa gaaggaggag gaggaagacg accgtgggga agacggccct aagccaatgc 3900
ctccctatag ctccatgttc atcctgtcca cgaccaaccc ccttcgccgc ctgtgccatt 3960
acatcctgaa cctgcgctac tttgagatgt gcatcctcat ggtcattgcc atgagcagca 4020
tcgccctggc cgccgaggac cctgtgcagc ccaacgcacc tcggaacaac gtgctgcgat 4080
actttgacta cgtttttaca ggcgtcttta cctttgagat ggtgatcaag atgattgacc 4140
tggggctcgt cctgcatcag ggtgcctact tccgtgacct ctggaatatt ctcgacttca 4200
tagtggtcag tggggccctg gtagcctttg ccttcactgg caatagcaaa ggaaaagaca 4260
tcaacacgat taaatccctc cgagtcctcc gggtgctacg acctcttaaa accatcaagc 4320
ggctgccaaa gctcaaggct gtgtttgact gtgtggtgaa ctcacttaaa aacgtcttca 4380

```
acatcctcat cgtctacatg ctattcatgt tcatcttcgc cgtggtggct gtgcagctct   4440
tcaaggggaa attcttccac tgcactgacg agtccaaaga gtttgagaaa gattgtcgag   4500
gcaaatacct cctctacgag aagaatgagg tgaaggcgcg agaccgggag tggaagaagt   4560
atgaattcca ttacgacaat gtgctgtggg ctctgctgac cctcttcacc gtgtccacgg   4620
gagaaggctg gccacaggtc ctcaagcatt cggtggacgc cacctttgag aaccagggcc   4680
ccagccccgg gtaccgcatg gagatgtcca ttttctacgt cgtctacttt gtggtgttcc   4740
ccttcttctt tgtcaatatc tttgtggcct tgatcatcat caccttccag gagcaagggg   4800
acaagatgat ggaggaatac agcctggaga aaaatgagag ggcctgcatt gatttcgcca   4860
tcagcgccaa gccgctgacc cgacacatgc cgcagaacaa gcagagcttc cagtaccgca   4920
tgtggcagtt cgtggtgtct ccgcctttcg agtacacgat catggccatg atcgccctca   4980
acaccatcgt gcttatgatg aagttctatg gggcttctgt tgcttatgaa aatgccctgc   5040
gggtgttcaa catcgtcttc acctccctct tctctctgga atgtgtgctg aaagtcatgg   5100
cttttgggat tctgaattat ttccgcgatg cctggaacat cttcgacttt gtgactgttc   5160
tgggcagcat caccgatatc ctcgtgactg agtttgggaa tccgaataac ttcatcaacc   5220
tgagctttct ccgcctcttc cgagctgccc ggctcatcaa acttctccgt cagggttaca   5280
ccatccgcat tcttctctgg acctttgtgc agtccttcaa ggccctgcct tatgtctgtc   5340
tgctgatcgc catgctcttc ttcatctatg ccatcattgg gatgcaggtg tttggtaaca   5400
ttggcatcga cgtggaggac gaggacagtg atgaagatga gttccaaatc actgagcaca   5460
ataacttccg gaccttcttc caggccctca tgcttctctt ccggagtgcc accggggaag   5520
cttggcacaa catcatgctt tcctgcctca gcgggaaacc gtgtgataag aactctggca   5580
tcctgactcg agagtgtggc aatgaatttg cttattttta ctttgtttcc ttcatcttcc   5640
tctgctcgtt tctgatgctg aatctctttg tcgccgtcat catggacaac tttgagtacc   5700
tcacccgaga ctcctccatc ctgggccccc accacctgga tgagtacgtg cgtgtctggg   5760
ccgagtatga ccccgcagct tggggccgca tgccttacct ggacatgtat cagatgctga   5820
gacacatgtc tccgcccctg ggtctgggga agaagtgtcc ggccagagtg gcttacaagc   5880
ggcttctgcg gatggacctg cccgtcgcag atgacaacac cgtccacttc aattccaccc   5940
tcatggctct gatccgcaca gccctggaca tcaagattgc caagggagga gccgacaaac   6000
agcagatgga cgctgagctg cggaaggaga tgatggcgat ttggcccaat ctgtcccaga   6060
agacgctaga cctgctggtc acacctcaca agtccacgga cctcaccgtg ggaagatct    6120
acgcagccat gatgatcatg gagtactacc ggcagagcaa ggccaagaag ctgcaggcca   6180
tgcgcgagga gcaggaccgg acacccctca tgttccagcg catggagccc ccgtccccaa   6240
cgcaggaagg gggacctggc cagaacgccc tcccctccac ccagctggac ccaggaggag   6300
ccctgatggc tcacgaaagc ggcctcaagg agagcccgtc ctgggtgacc cagcgtgccc   6360
aggagatgtt ccagaagacg ggcacatgga gtccggaaca aggcccccct accgacatgc   6420
ccaacagcca gcctaactct cagtccgtgg agatgcgaga gatgggcaga gatggctact   6480
ccgacagcga gcactacctc cccatggaag gccagggccg ggctgcctcc atgccccgcc   6540
tccctgcaga gaaccagagg agaaggggcc ggccacgtgg gaataacctc agtaccatct   6600
cagacaccag ccccatgaag cgttcagcct ccgtgctggg ccccaaggcc cgacgcctgg   6660
acgattactc gctggagcgg gtcccgcccg aggagaacca gcggcaccac cagcggcgcc   6720
```

gcgaccgcag ccaccgcgcc tctgagcgct ccctgggccg ctacaccgat gtggacacag 6780
gcttggggac agacctgagc atgaccaccc aatccgggga cctgccgtcg aaggagcggg 6840
accaggagcg gggccggccc aaggatcgga agcatcgaca gcaccaccac caccaccacc 6900
accaccacca tcccccgccc cccgacaagg accgctatgc ccaggaacgg ccggaccacg 6960
gccgggcacg ggctcgggac cagcgctggt cccgctcgcc cagcgagggc cgagagcaca 7020
tggcgcaccg gcagggcagt agttccgtaa gtggaagccc agccccctca acatctggta 7080
ccagcactcc gcggcggggc cgccgccagc tcccccagac cccctccacc ccccggccac 7140
acgtgtccta ttcccctgtg atccgtaagg ccggcggctc ggggcccccg cagcagcagc 7200
agcagcagca gcagcagcag cagcagcagg cggtggccag gccgggccgg gcggccacca 7260
gcggccctcg gaggtaccca ggccccacgg ccgagcctct ggccggagat cggccgccca 7320 cgggggggcca cagcagcggc cgctcgccca ggatggagag gcgggtccca ggcccggccc 7380
ggagcgagtc ccccagggcc tgtcgacacg gcggggcccg gtggccggca tctggcccgc 7440
acgtgtccga ggggcccccg ggtccccggc accatggcta ctaccggggc tccgactacg 7500
acgaggccga tggcccgggc agcgggggcg gcgaggaggc catggccggg gcctacgacg 7560 cgccacccccc cgtacgacac gcgtcctcgg gcgccaccgg gcgctcgccc aggactcccc 7620
gggcctcggg cccggcctgc gcctcgcctt ctcggcacgg ccggcgactc cccaacggct 7680
actacccggc gcacggactg gccaggcccc gcgggccggg ctccaggaag ggcctgcacg 7740
aaccctacag cgagagtgac gatgattggt gctaagcccg ggcgaggtgg cgcccgcccg 7800
gccccccacg caccccacgc acacacccca cccgaggagc cgcgcagagg ccgcgggggc 7860
ccagcacaga gggcccggga gagggccagc cgggagaccc cagactctgg agaggccagg 7920
gctgggccac aagggtgtcc cgcagagacc ctcggccaaa agagaccctc ctgggcagcc 7980
acggcgcccc ccaaccagcc ccgatccccc cacccacgac aggggctctc gggtgggagg 8040
cagggagcag acaaaccaca cagccaaggg atttgaatta actcagccat ttttggagaa 8100
ctttggggaa catgaaaaaa aaaaaaaaaa aaaaaaaaaa aaacattttt aaaagaaaaa 8160
acggggagaa aaaaatagct tctattgatg agttttatca tctcaattga atctttcctt 8220
tccctgatga agacagctgg tggccgagtg cggcaaagaa gccagaagga accagaatcc 8280
cagtgcccta cacccaccac cagacacact cacacccaca cacgttctca gacacacaca 8340
agagtgcttg ccggttatac caaaccctac tattactgcc tgcagaaatc aatttaaaaa 8400
aataataata acaataaaca attttaaaaa ggacaaaaaa attaatgatt gagaaaagag 8460
gcattttttt ctgacatttg gtcctgcttg aaacaacaaa agaagaagaa aaacccacca 8520
tcaccaccga ttcctttgct tcttttttcc ttttttccta ccttgtttga aaaccgtggg 8580
cttgggactg tgaattattg catgacattc aaaaagaaaa aaaaaataaa aaaaagttga 8640
atcaaa 8646

<210> SEQ ID NO 85
<211> LENGTH: 7242
<212> TYPE: DNA
<213> ORGANISM: Homo sapiens

<400> SEQUENCE: 85
gaaaaagggt gaaagagaaa cttggcgacc tcccggagga gttcgcgaag cgaccaggag 60
cgtgttgcca tcgtcctcac ccggcaccca attccaccac agagtcggga tttcgtcggt 120
gatcgtgatg gggtgctttt atttttctct ttgattttca aaaaatgtct atgtgactgt 180

```
ccctatctta aggggaagtt gaaagtgggg gcgggggtgc tcaatgagaa acgttgcctt    240
gtgtgtagtt gtttggagca cactgcaaat tatattggca tctctttcca aaagtcactt    300
tgattcaact tcgatagctt tctcgtaaat ggcacgttta ggtggtgaga ggtggatgag    360
gaaacaggca ccagtgcagc tgatttgacc tccagtggga tagatacgat tagcaccagg    420
atcgtgtctc attttgaacc cagatctgaa cagaattaag acgaacgagc tttcacaatt    480
gcagcagatg aagatccatt ggtaaattga tcaggatttt tggcctaccc tccaaagaaa    540
aggagcggaa agaatgtcgg agcgggccgc ggatgacgtc agggggggagc cgcgccgcgc    600
ggcggcggcg gcgggcggag cagcggccgc ggccgcccgg cagcagcagc agcagcagca    660
gcagcagcag ccgccgcctc cgcagcccca gcggcagcag cacccgccac cgccgccacg    720
gcgcacacgg ccggaggacg gcgggcccgg cgccgcctcc acctcggccg ccgcaatggc    780
gacggtcggg gagcgcaggc ctctgcccag tcctgaagtg atgctgggac agtcgtggaa    840
tctgtgggtt gaggcttcca aacttcctgg gaaggacggg acagaattgg acgaaagttt    900
caaggagttt gggaaaaacc gcgaagtcat ggggctctgt cgggaagaca tgccaatatt    960
tggtttctgt ccagcccatg atgatttcta cttggtggtg tgtaacgact gtaatcaggt   1020
tgtcaaaccg caggcatttc aatcacatta tgaaagaaga catagctcat ccagcaagcc   1080
gcctttggcc gttcctccca cttcagtatt ttccttcttc ccttctctgt ccaaaagcaa   1140
aggaggcagt gcaagtggaa gcaaccgttc ttccagtgga ggtgttctta gcgcatcctc   1200
atcaagttcc aagttgttga aatcacccaa agagaaactg cagctcaggg ggaacaccag   1260
gccaatgcat cccattcagc aaagtagagt tccccatggt agaatcatga caccctctgt   1320
gaaagtggaa aagattcatc cgaaaatgga tggcacacta ctgaaatctg cggtggggcc   1380
aacctgtcct gctactgtga gttccttagt caagcctggc cttaactgcc cctcaatacc   1440
aaagccaacc ttgccttcac ctggacagat tctgaatggc aaagggcttc ctgcaccgcc   1500
cactctggaa aagaaacctg aagacaattc caataatagg aaatttttaa ataagagatt   1560
atcagaaaga gagtttgatc ctgacatcca ctgtggggtt attgatctcg acaccaagaa   1620
gccctgcacc cggtctttga catgcaagac acattcctta acccagcgca gggctgtcca   1680
gggtagaaga aaacgatttg atgtgttatt agccgagcac aaaaacaaaa ccagggaaaa   1740
ggaattgatt cgccatccgg actctcagca accaccgcag cctctcaggg acccgcatcc   1800
cgcccctcct agaacgtcac aggagccgca ccaaaaccct cacggagtga ttccttccga   1860
atcaaagcct tttgtagcta gtaaacctaa acctcacacc cccagtcttc caaggcctcc   1920
aggctgccct gctcagcaag gtgggagtgc ccccattgac cctcctccag tccatgaatc   1980
tccacaccct cccctgcctg ccactgagcc agcttctcgg ttatccagtg aggagggcga   2040
aggcgatgac aaagaagagt ctgttgaaaa actggactgt cattattcag gtcatcatcc   2100
tcagccagca tctttttgca catttgggag ccggcagata ggaagaggct attacgtgtt   2160
tgactccagg tggaatcgac ttcgctgcgc cctcaacctc atggtggaga agcatctgaa   2220
tgcacagcta tggaagaaaa tcccaccagt gcccagtacc acctcaccca tctccacacg   2280
tattcctcac cggacaaact ctgtgccgac atcacaatgt ggagtcagct atctggcagc   2340
agccaccgtc tctacatccc cagtcctgct ctcatctacc tgcatctccc caaatagcaa   2400
atcggtacca gctcatggaa ccacactaaa tgcacagcct gctgcttcag gggcgatgga   2460
tcctgtgtgc agtatgcaat ccagacaagt gtcctcttca tcctcatccc cttccacgcc   2520
```

-continued

```
ctctggcctt tcctcggttc cttcctcccc catgtccagg aaacctcaga aattgaaatc   2580
cagcaaatct ttgaggccca aggagtcttc tggtaacagc actaactgtc aaaatgccag   2640
tagcagtacc agtggcggct caggaaagaa acgcaaaaac agttccccac tgttggttca   2700
ctcttcctcc tcctcttcct cctcctcctc ttcttctcat tccatggagt cttttaggaa   2760
aaactgtgtg gctcactctg ggcctcccta cccctcaacg gtaacatctt cccatagcat   2820
cggcctcaac tgtgtgacga ataaagcaaa tgcggtgaac gtccggcatg accagtcagg   2880
gaggggcccc cccaccggga gccctgctga atccatcaag aggatgagtg tgatggtgaa   2940
cagcagtgat tctactcttt ctcttgggcc attcattcac cagtccaatg aactgcctgt   3000
caactcccac ggcagttttt cccactcaca cactcctcta gacaaactca taggaaagaa   3060
aagaaagtgc tcacccagct cgagcagcat caacaacagc agcagcaaac ccacaaaggt   3120
tgccaaagtg ccagccgtga acaatgtcca catgaaacac acaggcacca tcccaggggc   3180
acaaggactg atgaacagtt ccctccttca tcagccaaag gcacgtccct gacagctgaa   3240
aatagcacgg ggaggaataa tgcggacact tttgaggaca agttacacct ccactcagca   3300
ctctggactc cacgatgcct ttgagtctgt tttcccaacc tcctgtgggc ctcaagggta   3360
gaaacctgcc gggctgttgt tttaacgagg atttccctga agctatgtct ctagcagtga   3420
gtactcataa aggacactgg atcaagttca gccaccgaat tgcttttatc agtgttaaag   3480
tggtctgaac tgcttgctac caatctgtga gaagtttttg tttttgtttt gtttttttaac   3540
ttgcagtata tcacagagcc actcttcaag tagattggct gggcaaaaga atgttttggc   3600
aagagcgtta ctgtagacct ttctccctcc ttccttttac taccattttt ttttaacact   3660
gtcatctgta ggtcactctc cagcagttag gcaccttaac tggagaccag aaaccttcca   3720
gagaacacag ggctgcatcc cgagcaaccc tctgaagaag ggaattaggc tttagatttt   3780
gatagcaatg ttccaggaat gaaatataga tgttagccca agacaccatg acaaaatagc   3840
ccagcctttt gagagtaatt tgggaaaaga agctgtcaga agtttctaac ttacaaactg   3900
gtttgaaatt tttgatgccc agacagcaag tataaatcat tttggaggct tacttttcat   3960
gatacaaaag caattctgtg tgattttttt ttttaagaag aaagaaaatg caagctagtt   4020
ttgagaaagg aaggccaaat tgggtcgggg gagggtggga gtgaggaagt taaaatcact   4080
atagggagaa aaaacttttt tcaagatttc caaagagatg aaatttttctt aatcctttta   4140
agttttcata gtaaacagta tggcagattg ggttggttgt cctacctggt ctatttttaa   4200
aagtcacctt ttaaagtgac attattagat acacttaaat gtttccaagg cactctctac   4260
attacccttg tttttctctt tggatactgt cctgggacta agtgtagatt tctgcttcaa   4320
gcacttctgg cattgtgtgt ttttgtatgc actccccttc atgccacttc agatgtttat   4380
ttggatgtgg ttggggacga gagcagacac caaggaaagg gagttggaga gaatgtaagt   4440
cctgacctga aggtcttttg tgatgcatgt ataggattgc cctgacacac accctccttt   4500
cttgggatta taccagccat cttcctgaga gttttggagc cctctaggat atttttttcta   4560
gtaccccacc ccccacccct aaagaaagac cttaatatgt taaaacagca ttgcttggag   4620
aaggtgtcat tgaattccgg gacgagccgg agcctttaaa tgggtgcttc caccactaca   4680
ggctcctgac acgagtaaca ggcactgttg cttagaagaa cacacgaagt tgccgaacac   4740
agggtaaaat ttccaaggcg ctgatcgttg ccctggccag ggcctgatga gagccagtca   4800
gtacattctt tttttcctac agttcttggg tttcaaactt cagtttcagg gaatttcaag   4860
tcaacaacag gtagaatgaa taaacttggt taccagccta ataatgtgaa ttgctacaga   4920
```

```
attattctta ttatgtaaga aaacaaaaac tttatgcaga tactttagct ataaattgat   4980
gtaaaatact gattttttta aaggaaggag agaacagtat cttgttcaat tattatgcaa   5040
tcaatcagta aatgttttta aaatgatact acaggagagc ttagtaagga gagggcatgg   5100
atgggccagt ttggcatagt tgggagaaat cagtctggtt tccatcccag tcggggaaga   5160
gagaggtgag agggaatcag aacgtaccta gttgattcct tggtgacaag tgcaatgggg   5220
tatgggtaga atttatttc agagccaaga ggacttgatg gttataaata aagttgcctt   5280
tagcaatgga atttacagat cgatcatgtt gttccgaaag atgtgaatag gatccacaat   5340
aacaagttga ttcagactaa tgtagatatt tagattagca agtattgaac atttgatttc   5400
ttagactgag gttttaaatg aatttcatta tttctcccgg taatacacag agcatcggga   5460
ttaggaaatt agccattttg gattctgtct gccacaaaca gacctattct aaacagtgct   5520
attaaatttt agactgttgt tcaaatattt tattttctcc taaactactt tttatggtga   5580
tgaataatta agaccattta aaacacggga gtacaagtat tttttgaat taaattaact   5640
tgcaaaaacc aaatttgcag tggttgggtt gtttctagac agactttggt atcaatttaa   5700
aaccaagata atttttatat tctttccaat agaatttcat gacaactcct gcagttttct   5760
taacctacaa aaaaaaaaaa aaagtgctgc aatgatgaac aaagaattat acaaaaccta   5820
cttttgtatc tttattttgg aatttcttgt tctattataa atatggaagt atccctattt   5880
cagaagacat attttgttaa aaatgaattg tacatattta aatatgtatt tttgcacagg   5940
tcttttttc tgatatcctg ttttggtaca attgagatca tctagtattt atttattaat   6000
taataaaagt aaatacettt ttataatttg aagtggttca ctgccaagcc aatagttcta   6060
gaacctgcct cctttacagt tttaagggat gcctctgttc tgtgaaaagt ctttgtccct   6120
tttagtgtct cgggagtgga ttcatacaga tgaagtgggc attgcttctt cctggttgcc   6180
tggtttcccg atagactaca tgtaactaag tgacacactg cttttctttt gttagtattt   6240
tatgtgtggg agtatgtgac tgcgtgtgtg tgtgcctgtg cgtgtgtgtg tatactcagc   6300
acatgtatgt tactatgtga tgtggtttaa aactaatgga aaaaactgaa agtgcctgaa   6360
actagtttta agcttagaca gaatctcttt aaaaagactt gaatgttcag ttgaactttt   6420
ggagtttgct ttttccacct aaatattgtt tctaaaattt taggggcgga gttgaaaacc   6480
accaatgctg gtaattttat aaggtatttt aaaattaaga cctcttggtt catagtaatt   6540
caattggtga tggattgcct ggtggcacca agggttacag atctttttgt cagccagcaa   6600
cttacacgat gtgtccgttt tgttattcac tcatgaaata caatttaaaa tatttaaaat   6660
attttgtatt ccaaaaatat aatacaaaga agtacctctg agaacattga aaaaaatgta   6720
taatttgaaa aatgtaactt ataagggcag ctgtcttcct gcaagagttc tgttgccaag   6780
gaatttctta atgtcgctca ttctgtccag gggtttggg gcgattgggc tttgaaaaaa   6840
tattcttaaa agtttgttta gcagaaaata atcactttta cattttgtgc aaaacatttt   6900
acattttcag ataatttaaa tgagcactac atactgtcag tgtgaatgta gggccttgaa   6960
agcattttgc tttttttttt tttttttttt ttttgagctt ggttataaaa gcaatctcct   7020
gtgttaaaaa cgtgtgaata gtttgataat ttgtacacat aatcaagagc atctcagctg   7080
gactttgtgt tggctgctgt atagaacatg aacaaatgtc aagggataga aaattacttt   7140
ggatatttaa aagagaagaa atatatagtc tatttgtttt gtaacaagtt tctgtaaata   7200
aaataattta tactatttat aagaaaaaaa aaaaaaaaaa aa                      7242
```

<210> SEQ ID NO 86
<211> LENGTH: 2300
<212> TYPE: DNA
<213> ORGANISM: Homo sapiens

<400> SEQUENCE: 86
ggccaggcaa gcctgaatcc tgtccctgcc atctcgccac tgcagctcgg gtccagaaag 60
gcaccatttt gtcgcggctg cccgctctcc caggggggagg agggatcttt tttgcatttt 120
ggagcggctg ccaaggaggg gaacctgttg ggcatctccc cagacccgct tgtgagcgcc 180
tccggggcgg gcgggcggga ccagacccct cggggcacgg cgtatcttgg cacccggagg 240
cagcggaggc aggcgcagca tcctcgctgg gaactggagc tggagtgagc gcaccgcgcg 300
ggaggagccg ccgcagcctc gcagaacccg agtggaggag gtgacagctc cattgccggg 360
tttttatttt ttttctctcc gcctccccgt ctcctcctca ggctcggacc atggtgcagt 420
cccactggct cccctgcccc cctctcctgt gagactggct gcggggaggg atcatggata 480
cttgtctgcc ggcttctggt tcccacgcaa gtaagcctgc tgtcaatgga ggaggacatt 540
gatacccgca aaatcaacaa cagtttcctg cgcgaccaca gctatgcgac cgaagctgac 600
attatctcta cggtagaatt caaccacacg ggagaattac tagcgacagg ggacaagggg 660
ggtcgggttg taatatttca acgagagcag gagagtaaaa atcaggttca tcgtaggggt 720
gaatacaatg tttacagcac attccagagc catgaacccg agttcgatta cctgaagagt 780
ttagaaatag aagaaaaaat caataaaata agatggctcc cccagcagaa tgcagcttac 840
tttcttctgt ctactaatga taaaactgtg aagctgtgga aagtcagcga gcgtgataag 900
aggccagaag gctacaatct gaaagatgag gagggccggc tccgggatcc tgccaccatc 960
acaaccctgc gggtgcctgt cctgagaccc atggacctga tggtggaggc caccccacga 1020
agagtatttg ccaacgcaca cacatatcac atcaactcca tatctgtcaa cagcgactat 1080
gaaacctaca tgtccgctga tgacctgagg attaacctat ggaactttga aataaccaat 1140
caaagtttta atattgtgga cattaagcca gccaacatgg aggagctcac ggaggtgatc 1200
acagcagccg agttccaccc ccatcattgc aacaccttcg tgtacagcag cagcaaaggg 1260
acaatccggc tgtgtgacat gcgggcatct gccctgtgtg acaggcacac caaatttttt 1320
gaagagccgg aagatccaag caacagatca tttttctctg aaattatctc ttcgatttcg 1380
gatgtgaagt tcagccacag tgggaggtat atcatgacca gggactactt gaccgtcaaa 1440
gtctgggatc tcaacatgga aaaccgcccc atcgagactt accaggttca tgactacctc 1500
cgcagcaagc tgtgttccct ctatgaaaat gactgcattt ttgataaatt tgagtgtgtg 1560
tggaatgggt cagacagtgt catcatgaca ggctcctaca acaacttctt caggatgttc 1620
gacagaaaca ccaagcgtga tgtgaccctt gaggcttcga gggaaaacag caagccccgg 1680
gctatcctca aaccccgaaa agtgtgtgtg gggggcaagc ggagaaaaga cgagatcagt 1740
gtcgacagtc tggactttag caaaaagatc ttgcatacag cttggcatcc ttcagaaaat 1800
attatagcag tggcggctac aaataaccta tatatattcc aggacaaggt taactaggtg 1860
gacaagttat tacttaataa tctcacatac tgaatactag tcaaacaagt ttttaaatgt 1920
ttctttgggt cttcatttga tgcattgact ttaatttccc tatacaggaa atgattggaa 1980
tagaattaaa aggagtccaa cattcccagc tccccagttc taagaaactt ttgtcaaacc 2040
caataggttt gggacacttc tgtttagaat tgaaagctgc cagctaacag taattcttcc 2100
atagttgact tgaacttctg atgcttttat tgcccagttt tctctggtgg gtccagtgtt 2160
ttgttcctag gtgtctgctg cgataaaatg aggttgtctg tagtatttaa ggagaaaaga 2220
gataagtttt ttttaattaa gcaattccat ttgattgaaa aaaatcaaca aaaaataaac 2280
accgtttact cttagacaaa 2300

<210> SEQ ID NO 87
<211> LENGTH: 1921
<212> TYPE: DNA
<213> ORGANISM: Homo sapiens

<400> SEQUENCE: 87
ggcggaagtg acattatcaa cgcgcgccag gggttcagtg aggtcgggca ggttcgctgt 60
ggcgggcgcc tgggccgccg gctgtttaac ttcgcttccg ctggcccata gtgatctttg 120
cagtgaccca gcatcactgt ttcttggcgt gtgaagataa cccaaggaat tgaggaagtt 180
gctgagaaga gtgtgctgga gatgctctag gaaaaaattg aatagtgaga cgagttccag 240
cgcaagggtt tctggtttgc caagaagaaa gtgaacatca tggatcagaa caacagcctg 300
ccaccttacg ctcagggctt ggcctcccct cagggtgcca tgactcccgg aatccctatc 360
tttagtccaa tgatgcctta tggcactgga ctgaccccac agcctattca gaacaccaat 420
agtctgtcta ttttggaaga gcaacaaagg cagcagcagc aacaacaaca gcagcagcag 480
cagcagcagc agcaacagca acagcagcag cagcagcagc agcagcagca gcagcagcag 540
cagcagcagc agcagcagca acaggcagtg gcagctgcag ccgttcagca gtcaacgtcc 600
cagcaggcaa cacagggaac ctcaggccag gcaccacagc tcttccactc acagactctc 660
acaactgcac ccttgccggg caccactcca ctgtatccct cccccatgac tcccatgacc 720
cccatcactc ctgccacgcc agcttcggag agttctggga ttgtaccgca gctgcaaaat 780
attgtatcca cagtgaatct tggttgtaaa cttgacctaa agaccattgc acttcgtgcc 840
cgaaacgccg aatataatcc caagcggttt gctgcggtaa tcatgaggat aagagagcca 900
cgaaccacgg cactgatttt cagttctggg aaaatggtgt gcacaggagc caagagtgaa 960
gaacagtcca gactggcagc aagaaaatat gctagagttg tacagaagtt gggttttcca 1020
gctaagttct tggacttcaa gattcagaat atggtgggga gctgtgatgt gaagtttcct 1080
ataaggttag aaggccttgt gctcacccac caacaattta gtagttatga gccagagtta 1140
tttcctggtt taatctacag aatgatcaaa cccagaattg ttctccttat ttttgtttct 1200
ggaaaagttg tattaacagg tgctaaagtc agagcagaaa tttatgaagc atttgaaaac 1260
atctacccta ttctaaaggg attcaggaag acgacgtaat ggctctcatg taccettgcc 1320 tcccccaccc ccttcttttt tttttttaa acaaatcagt ttgttttggt acctttaaat 1380
ggtggtgttg tgagaagatg gatgttgagt tgcagggtgt ggcaccaggt gatgcccttc 1440
tgtaagtgcc caccgcggga tgccgggaag ggcattattt tgtgcactga gaacaccgcg 1500
cagcgtgact gtgagttgct cataccgtgc tgctatctgg gcagcgctgc ccatttattt 1560
atatgtagat tttaaacact gctgttgaca agttggtttg agggagaaaa ctttaagtgt 1620
taaagccacc tctataattg attggacttt ttaattttaa tgtttttccc catgaaccac 1680
agtttttata tttctaccag aaaagtaaaa atcttttta aaagtgttgt ttttctaatt 1740
tataactcct aggggttatt tctgtgccag acacattcca cctctccagt attgcaggac 1800
agaatatatg tgttaatgaa aatgaatggc tgtacatatt tttttcttc ttcagagtac 1860 tctgtacaat aaatgcagtt tataaaagtg ttagattgtt gttaaaaaaa aaaaaaaaaa 1920

-continued a 1921

<210> SEQ ID NO 88
<211> LENGTH: 10661
<212> TYPE: DNA
<213> ORGANISM: Homo sapiens

<400> SEQUENCE: 88
cgagatcccg gggagccagc ttgctgggag agcgggacgg tccggagcaa gcccagaggc 60
agaggaggcg acagagggaa aaagggccga gctagccgct ccagtgctgt acaggagccg 120
aagggacgca ccacgccagc cccagcccgg ctccagcgac agccaacgcc tcttgcagcg 180
cggcggcttc gaagccgccg cccggagctg cccttccctc ttcggtgaag tttttaaaag 240
ctgctaaaga ctcggaggaa gcaaggaaag tgcctggtag gactgacggc tgcctttgtc 300
ctcctcctct ccaccccgcc tccccccacc ctgccttccc cccctccccc gtcttctctc 360
ccgcagctgc ctcagtcggc tactctcagc caaccccctt caccaccctt ctccccaccc 420
gcccccccgc ccccgtcggc ccagcgctgc cagcccgagt ttgcagagag gtaactccct 480
ttggctgcga gcgggcgagc tagctgcaca ttgcaaagaa ggctcttagg agccaggcga 540
ctggggagcg gcttcagcac tgcagccacg acccgcctgg ttaggctgca cgcggagaga 600
accctctgtt ttcccccact ctctctccac ctcctcctgc cttccccacc ccgagtgcgg 660
agccagagat caaaagatga aaaggcagtc aggtcttcag tagccaaaaa acaaaacaaa 720
caaaaacaaa aaagccgaaa taaaagaaaa agataataac tcagttctta tttgcaccta 780
cttcagtgga cactgaattt ggaaggtgga ggattttgtt tttttctttt aagatctggg 840
catcttttga atctaccctt caagtattaa gagacagact gtgagcctag cagggcagat 900
cttgtccacc gtgtgtcttc ttctgcacga gactttgagg ctgtcagagc gctttttgcg 960
tggttgctcc cgcaagtttc cttctctgga gcttcccgca ggtgggcagc tagctgcagc 1020
gactaccgca tcatcacagc ctgttgaact cttctgagca agagaagggg aggcggggta 1080
agggaagtag gtggaagatt cagccaagct caaggatgga agtgcagtta gggctgggaa 1140
gggtctaccc tcggccgccg tccaagacct accgaggagc tttccagaat ctgttccaga 1200
gcgtgcgcga agtgatccag aacccgggcc ccaggcaccc agaggccgcg agcgcagcac 1260
ctcccggcgc cagtttgctg ctgctgcagc agcagcagca gcagcagcag cagcagcagc 1320
agcagcagca gcagcagcag cagcagcagc agcaagagac tagccccagg cagcagcagc 1380
agcagcaggg tgaggatggt tctccccaag cccatcgtag aggccccaca ggctacctgg 1440
tcctggatga ggaacagcaa ccttcacagc cgcagtcggc cctggagtgc caccccgaga 1500
gaggttgcgt cccagagcct ggagccgccg tggccgccag caaggggctg ccgcagcagc 1560
tgccagcacc tccggacgag gatgactcag ctgccccatc cacgttgtcc ctgctgggcc 1620
ccactttccc cggcttaagc agctgctccg ctgaccttaa agacatcctg agcgaggcca 1680
gcaccatgca actccttcag caacagcagc aggaagcagt atccgaaggc agcagcagcg 1740
ggagagcgag ggaggcctcg ggggctccca cttcctccaa ggacaattac ttagggggca 1800
cttcgaccat ttctgacaac gccaaggagt tgtgtaaggc agtgtcggtg tccatgggcc 1860
tgggtgtgga ggcgttggag catctgagtc caggggaaca gcttcggggg gattgcatgt 1920
acgccccact tttgggagtt ccacccgctg tgcgtcccac tccttgtgcc ccattggccg 1980
aatgcaaagg ttctctgcta gacgacagcg caggcaagag cactgaagat actgctgagt 2040
attccccttt caagggaggt tacaccaaag ggctagaagg cgagagccta ggctgctctg 2100

-continued

```
gcagcgctgc agcagggagc tccgggacac ttgaactgcc gtctaccctg tctctctaca   2160
agtccggagc actggacgag gcagctgcgt accagagtcg cgactactac aactttccac   2220
tggctctggc cggaccgccg ccccctccgc cgcctcccca tccccacgct cgcatcaagc   2280
tggagaaccc gctggactac ggcagcgcct gggcggctgc ggcggcgcag tgccgctatg   2340
gggacctggc gagcctgcat ggcgcgggtg cagcgggacc cggttctggg tcaccctcag   2400
ccgccgcttc ctcatcctgg cacactctct tcacagccga agaaggccag ttgtatggac   2460
cgtgtggtgg tggtgggggt ggtggcggcg gcggcggcgg cggcggcggc ggcggcggcg   2520
gcggcggcgg cggcgaggcg ggagctgtag ccccctacgg ctacactcgg ccccctcagg   2580
ggctggcggg ccaggaaagc gacttcaccg cacctgatgt gtggtaccct ggcggcatgg   2640
tgagcagagt gccctatccc agtcccactt gtgtcaaaag cgaaatgggc ccctggatgg   2700
atagctactc cggaccttac ggggacatgc gtttggagac tgccagggac catgttttgc   2760
ccattgacta ttactttcca ccccagaaga cctgcctgat ctgtggagat gaagcttctg   2820
ggtgtcacta tggagctctc acatgtggaa gctgcaaggt cttcttcaaa agagccgctg   2880
aagggaaaca gaagtacctg tgcgccagca gaaatgattg cactattgat aaattccgaa   2940
ggaaaaattg tccatcttgt cgtcttcgga aatgttatga agcagggatg actctgggag   3000
cccggaagct gaagaaactt ggtaatctga aactacagga ggaaggagag gcttccagca   3060
ccaccagccc cactgaggag acaacccaga agctgacagt gtcacacatt gaaggctatg   3120
aatgtcagcc catctttctg aatgtcctgg aagccattga gccaggtgta gtgtgtgctg   3180
gacacgacaa caaccagccc gactcctttg cagccttgct ctctagcctc aatgaactgg   3240
gagagagaca gcttgtacac gtggtcaagt gggccaaggc cttgcctggc ttccgcaact   3300
tacacgtgga cgaccagatg gctgtcattc agtactcctg gatggggctc atggtgtttg   3360
ccatgggctg gcgatccttc accaatgtca actccaggat gctctacttc gcccctgatc   3420
tggttttcaa tgagtaccgc atgcacaagt cccggatgta cagccagtgt gtccgaatga   3480
ggcacctctc tcaagagttt ggatggctcc aaatcacccc ccaggaattc ctgtgcatga   3540
aagcactgct actcttcagc attattccag tggatgggct gaaaaatcaa aaattctttg   3600
atgaacttcg aatgaactac atcaaggaac tcgatcgtat cattgcatgc aaaagaaaaa   3660
atcccacatc ctgctcaaga cgcttctacc agctcaccaa gctcctggac tccgtgcagc   3720
ctattgcgag agagctgcat cagttcactt ttgacctgct aatcaagtca cacatggtga   3780
gcgtggactt tccggaaatg atggcagaga tcatctctgt gcaagtgccc aagatccttt   3840
ctgggaaagt caagcccatc tatttccaca cccagtgaag cattggaaac cctatttccc   3900
caccccagct catgccccct ttcagatgtc ttctgcctgt tataactctg cactactcct   3960
ctgcagtgcc ttggggaatt tcctctattg atgtacagtc tgtcatgaac atgttcctga   4020
attctatttg ctgggctttt tttttctctt tctctccttt ctttttcttc ttccctccct   4080
atctaaccct cccatggcac cttcagactt tgcttcccat tgtggctcct atctgtgttt   4140
tgaatggtgt tgtatgcctt taaatctgtg atgatcctca tatggcccag tgtcaagttg   4200
tgcttgttta cagcactact ctgtgccagc cacacaaacg tttacttatc ttatgccacg   4260
ggaagtttag agagctaaga ttatctgggg aaatcaaaac aaaaacaagc aaacaaaaaa   4320
aaaaagcaaa aacaaaacaa aaaataagcc aaaaaacctt gctagtgttt tttcctcaaa   4380
aataaataaa taaataaata aatacgtaca tacatacaca catacataca aacatataga   4440
```

-continued

```
aatccccaaa gaggccaata gtgacgagaa ggtgaaaatt gcaggcccat ggggagttac   4500
tgattttttc atctcctccc tccacgggag actttatttt ctgccaatgg ctattgccat   4560
tagagggcag agtgacccca gagctgagtt gggcaggggg gtggacagag aggagaggac   4620
aaggagggca atggagcatc agtacctgcc cacagccttg gtccctgggg gctagactgc   4680
tcaactgtgg agcaattcat tatactgaaa atgtgcttgt tgttgaaaat ttgtctgcat   4740
gttaatgcct cacccccaaa cccttttctc tctcactctc tgcctccaac ttcagattga   4800
ctttcaatag tttttctaag acctttgaac tgaatgttct cttcagccaa aacttggcga   4860
cttccacaga aaagtctgac cactgagaag aaggagagca gagatttaac cctttgtaag   4920
gccccatttg gatccaggtc tgctttctca tgtgtgagtc agggaggagc tggagccaga   4980
ggagaagaaa atgatagctt ggctgttctc ctgcttagga cactgactga atagttaaac   5040
tctcactgcc actacctttt ccccaccttt aaaagacctg aatgaagttt tctgccaaac   5100
tccgtgaagc cacaagcacc ttatgtcctc ccttcagtgt tttgtgggcc tgaatttcat   5160
cacactgcat ttcagccatg gtcatcaagc ctgtttgctt cttttgggca tgttcacaga   5220
ttctctgtta agagccccca ccaccaagaa ggttagcagg ccaacagctc tgacatctat   5280
ctgtagatgc cagtagtcac aaagatttct taccaactct cagatcgctg gagcccttag   5340
acaaactgga aagaaggcat caaagggatc aggcaagctg ggcgtcttgc ccttgtcccc   5400
cagagatgat accctcccag caagtggaga agttctcact tccttcttta gagcagctaa   5460
aggggctacc cagatcaggg ttgaagagaa aactcaatta ccagggtggg aagaatgaag   5520
gcactagaac cagaaaccct gcaaatgctc ttcttgtcac ccagcatatc cacctgcaga   5580
agtcatgaga agagagaagg aacaaagagg agactctgac tactgaatta aaatcttcag   5640
cggcaaagcc taaagccaga tggacaccat ctggtgagtt tactcatcat cctcctctgc   5700
tgctgattct gggctctgac attgcccata ctcactcaga ttccccacct ttgttgctgc   5760
ctcttagtca gagggaggcc aaaccattga gactttctac agaaccatgg cttctttcgg   5820
aaaggtctgg ttggtgtggc tccaatactt tgccacccat gaactcaggg tgtgccctgg   5880
gacactggtt ttatatagtc ttttggcaca cctgtgttct gttgacttcg ttcttcaagc   5940
ccaagtgcaa gggaaaatgt ccacctactt tctcatcttg gcctctgcct ccttacttag   6000
ctcttaatct catctgttga actcaagaaa tcaagggcca gtcatcaagc tgcccatttt   6060
aattgattca ctctgtttgt tgagaggata gtttctgagt gacatgatat gatccacaag   6120
ggtttccttc cctgatttct gcattgatat taatagccaa acgaacttca aaacagcttt   6180
aaataacaag ggagagggga acctaagatg agtaatatgc caatccaaga ctgctggaga   6240
aaactaaagc tgacaggttc ccttttttggg gtgggataga catgttctgg ttttctttat   6300
tattacacaa tctggctcat gtacaggatc acttttagct gttttaaaca gaaaaaaata   6360
tccaccactc ttttcagtta cactaggtta cattttaata ggtcctttac atctgttttg   6420
gaatgatttt catcttttgt gatacacaga ttgaattata tcattttcat atctctcctt   6480
gtaaatacta gaagctctcc tttacatttc tctatcaaat ttttcatctt tatgggtttc   6540
ccaattgtga ctcttgtctt catgaatata tgtttttcat ttgcaaaagc caaaaatcag   6600
tgaaacagca gtgtaattaa aagcaacaac tggattactc caaatttcca aatgacaaaa   6660
ctagggaaaa atagcctaca caagccttta ggcctactct ttctgtgctt gggtttgagt   6720
gaacaaagga gattttagct tggctctgtt ctcccatgga tgaaaggagg aggatttttt   6780
ttttcttttg gccattgatg ttctagccaa tgtaattgac agaagtctca ttttgcatgc   6840
```

gctctgctct acaaacagag ttggtatggt tggtatactg tactcacctg tgagggactg 6900
gccactcaga cccacttagc tggtgagcta gaagatgagg atcactcact ggaaaagtca 6960
caaggaccat ctccaaacaa gttggcagtg ctcgatgtgg acgaagagtg aggaagagaa 7020
aaagaaggag caccagggag aaggctccgt ctgtgctggg cagcagacag ctgccaggat 7080
cacgaactct gtagtcaaag aaaagagtcg tgtggcagtt tcagctctcg ttcattgggc 7140
agctcgccta ggcccagcct ctgagctgac atgggagttg ttggattctt tgtttcatag 7200
ctttttctat gccataggca atattgttgt tcttggaaag tttattattt ttttaactcc 7260
cttactctga gaaagggata ttttgaagga ctgtcatata tctttgaaaa aagaaaatct 7320
gtaatacata tatttttatg tatgttcact ggcactaaaa aatatagaga gcttcattct 7380
gtcctttggg tagttgctga ggtaattgtc caggttgaaa aataatgtgc tgatgctaga 7440
gtccctctct gtccatactc tacttctaaa tacatatagg catacatagc aagttttatt 7500
tgacttgtac tttaagagaa aatatgtcca ccatccacat gatgcacaaa tgagctaaca 7560
ttgagcttca agtagcttct aagtgtttgt ttcattaggc acagcacaga tgtggccttt 7620
ccccccttct ctcccttgat atctggcagg gcataaaggc ccaggccact tcctctgccc 7680
cttcccagcc ctgcaccaaa gctgcatttc aggagactct ctccagacag cccagtaact 7740
acccgagcat ggcccctgca tagccctgga aaaataagag gctgactgtc tacgaattat 7800
cttgtgccag ttgcccaggt gagagggcac tgggccaagg gagtggtttt catgtttgac 7860
ccactacaag gggtcatggg aatcaggaat gccaaagcac cagatcaaat ccaaaactta 7920
aagtcaaaat aagccattca gcatgttcag tttcttggaa aaggaagttt ctacccctga 7980
tgcctttgta ggcagatctg ttctcaccat taatcttttt gaaaatcttt taaagcagtt 8040
tttaaaaaga gagatgaaag catcacatta tataaccaaa gattacattg tacctgctaa 8100
gataccaaaa ttcataaggg caggggggga gcaagcatta gtgcctcttt gataagctgt 8160
ccaaagacag actaaaggac tctgctggtg actgacttat aagagctttg tgggtttttt 8220
tttccctaat aatatacatg tttagaagaa ttgaaaataa tttcgggaaa atgggattat 8280
gggtccttca ctaagtgatt ttataagcag aactggcttt ccttttctct agtagttgct 8340
gagcaaattg ttgaagctcc atcattgcat ggttggaaat ggagctgttc ttagccactg 8400
tgtttgctag tgcccatgtt agcttatctg aagatgtgaa acccttgctg ataagggagc 8460
atttaaagta ctagattttg cactagaggg acagcaggca gaaatcctta tttctgccca 8520
ctttggatgg cacaaaaagt tatctgcagt tgaaggcaga aagttgaaat acattgtaaa 8580
tgaatatttg tatccatgtt tcaaaattga aatatatata tatatatata tatatatata 8640
tatatatata tagtgtgtgt gtgtgttctg atagctttaa ctttctctgc atctttatat 8700
ttggttccag atcacacctg atgccatgta cttgtgagag aggatgcagt tttgttttgg 8760
aagctctctc agaacaaaca agacacctgg attgatcagt taactaaaag ttttctcccc 8820
tattgggttt gacccacagg tcctgtgaag gagcagaggg ataaaaagag tagaggacat 8880
gatacattgt actttactag ttcaagacag atgaatgtgg aaagcataaa aactcaatgg 8940
aactgactga gatttaccac agggaaggcc caaacttggg gccaaaagcc tacccaagtg 9000
attgaccagt ggccccctaa tgggacctga gctgttggaa gaagagaact gttccttggt 9060
cttcaccatc cttgtgagag aagggcagtt tcctgcattg gaacctggag caagcgctct 9120
atctttcaca caaattccct cacctgagat tgaggtgctc ttgttactgg gtgtctgtgt 9180

-continued

```
gctgtaattc tggttttgga tatgttctgt aaagattttg acaaatgaaa atgtgttttt   9240
ctctgttaaa acttgtcaga gtactagaag ttgtatctct gtaggtgcag gtccatttct   9300
gcccacaggt agggtgtttt tctttgatta agagattgac acttctgttg cctaggacct   9360
cccaactcaa ccatttctag gtgaaggcag aaaaatccac attagttact cctcttcaga   9420
catttcagct gagataacaa atcttttgga attttttcac ccatagaaag agtggtagat   9480
atttgaattt agcaggtgga gtttcatagt aaaaacagct tttgactcag ctttgattta   9540
tcctcatttg atttggccag aaagtaggta atatgcattg attggcttct gattccaatt   9600
cagtatagca aggtgctagg tttttccctt tccccacctg tctcttagcc tggggaatta   9660
aatgagaagc cttagaatgg gtggcccttg tgacctgaaa cacttcccac ataagctact   9720
taacaagatt gtcatggagc tgcagattcc attgcccacc aaagactaga acacacacat   9780
atccatacac caaaggaaag acaattctga aatgctgttt ctctggtggt tccctctctg   9840
gctgctgcct cacagtatgg gaacctgtac tctgcagagg tgacaggcca gatttgcatt   9900
atctcacaac cttagccctt ggtgctaact gtcctacagt gaagtgcctg gggggttgtc   9960
ctatcccata agccacttgg atgctgacag cagccaccat cagaatgacc cacgcaaaaa  10020
aaagaaaaaa aaaattaaaa agtcccctca caacccagtg acacctttct gctttcctct  10080
agactggaac attgattagg gagtgcctca gacatgacat tcttgtgctg tccttggaat  10140
taatctggca gcaggaggga gcagactatg taaacagaga taaaaattaa ttttcaatat  10200
tgaaggaaaa aagaaataag aagagagaga gaaagaaagc atcacacaaa gatttcttta  10260
aaagaaacaa ttttgcttga aatctcttta gatggggctc atttctcacg gtggcacttg  10320
gcctccactg ggcagcagga ccagctccaa gcgctagtgt tctgttctct ttttgtaatc  10380
ttggaatctt ttgttgctct aaatacaatt aaaaatggca gaaacttgtt tgttggacta  10440
catgtgtgac tttgggtctg tctctgcctc tgctttcaga aatgtcatcc attgtgtaaa  10500
atattggctt actggtctgc cagctaaaac ttggccacat cccctgttat ggctgcagga  10560
tcgagttatt gttaacaaag agacccaaga aaagctgcta atgtcctctt atcattgttg  10620
ttaatttgtt aaaacataaa gaaatctaaa atttcaaaaa a                      10661
```

<210> SEQ ID NO 89
<211> LENGTH: 4367
<212> TYPE: DNA
<213> ORGANISM: Homo sapiens

<400> SEQUENCE: 89

```
gacgccatac tggacgccaa gtgggaggaa cttcaaggct gtcccctgcg ggcctcccgc     60
tctgcttctg cgaaggtttc attgaaaaca gatcctgcaa aagttccagg tgcccacact    120
ggaaacttgg agatcctgct tcccagacca cagctgtggg gaacttgggg tggagcagag    180
aagtttctgt attcagctgc ccaggcagag gagaatgggg tctccacagc ctgaagaatg    240
aagacacgac agaataaaga ctcgatgtca atgaggagtg gacggaagaa agaggcccct    300
gggccccggg aagaactgag atcgaggggc cgggcctccc ctggaggggt cagcacgtcc    360
agcagtgatg gcaaagctga gaagtccagg cagacagcca agaaggcccg agtagaggaa    420
gcctccaccc caaaggtcaa caagcagggt cggagtgagg agatctcaga gagtgaaagt    480
gaggagacca atgcaccaaa aaagaccaaa actgagcagg aactccctcg gccacagtct    540
ccctccgatc tggatagctt ggacgggcgg agccttaatg atgatggcag cagcgaccct    600
agggatatcg accaggacaa ccgaagcacg tcccccagta tctacagccc tggaagtgtg    660
```

-continued

```
gagaatgact ctgactcatc ttctggcctg tcccagggcc cagcccgccc ctaccaccca    720
cctccactct ttcctccttc ccctcaaccg ccagacagca cccctcgaca gccagaggct    780
agctttgaac cccatccttc tgtgacaccc actggatatc atgctcccat ggagcccccc    840
acatctcgaa tgttccaggc tcctcctggg gcccctcccc ctcacccaca gctctatcct    900
gggggcactg gtggagtttt gtctggaccc ccaatgggtc ccaagggggg aggggctgcc    960
tcatcagtgg ggggccctaa tgggggtaag cagcaccccc cacccactac tcccatttca   1020
gtatcaagct ctggggctag tggtgctccc ccaacaaagc cgcctaccac tccagtgggt   1080
ggtgggaacc taccttctgc tccaccacca gccaacttcc cccatgtgac accgaacctg   1140
cctcccccac ctgccctgag acccctcaac aatgcatcag cctctccccc tggcctgggg   1200
gcccaaccac tacctggtca tctgccctct ccccacgcca tgggacaggg tatgggtgga   1260
cttcctcctg gcccagagaa gggcccaact ctggctcctt caccccactc tctgcctcct   1320
gcttcctctt ctgctccagc gccccccatg aggtttcctt attcatcctc tagtagtagc   1380
tctgcagcag cctcctcttc cagttcttcc tcctcttcct ctgcctcccc cttcccagct   1440
tcccaggcat tgcccagcta cccccactct ttccctcccc caacaagcct ctctgtctcc   1500
aatcagcccc ccaagtatac tcagccttct ctcccatccc aggctgtgtg gagccagggt   1560
cccccaccac ctcctcccta tggccgcctc ttagccaaca gcaatgccca tccaggcccc   1620
ttccctccct ctactggggc ccagtccacc gcccacccac cagtctcaac acatcaccat   1680
caccaccagc aacagcaaca gcagcagcag cagcagcagc agcagcagca gcagcagcag   1740
cagcatcacg gaaactctgg gccccctcct cctggagcat ttccccaccc actggagggc   1800
ggtagctccc accacgcaca cccttacgcc atgtctccct ccctggggtc tctgaggccc   1860
tacccaccag ggccagcaca cctgccccca cctcacagcc aggtgtccta cagccaagca   1920
ggccccaatg gccctccagt ctcttcctct tccaactctt cctcttccac ttctcaaggg   1980
tcctacccat gttcacaccc ctccccttcc cagggccctc aaggggcgcc ctaccctttc   2040
ccaccggtgc ctacggtcac cacctcttcg gctacccttt ccacggtcat tgccaccgtg   2100
gcttcctcgc cagcaggcta caaaacggcc tccccacctg ggcccccacc gtacggaaag   2160
agagccccgt ccccgggggc ctacaagaca gccaccccac ccggatacaa acccgggtcg   2220
cctccctcct tccgaacggg gaccccaccg ggctatcgag gaacctcgcc acctgcaggc   2280
ccagggacct tcaagccggg ctcgcccacc gtgggacctg ggcccctgcc acctgcgggg   2340
ccctcaggcc tgccatcgct gccaccacca cctgcggccc ctgcctcagg gccgcccctg   2400
agcgccacgc agatcaaaca ggagccggct gaggagtatg agacccccga gagcccggtg   2460
cccccagccc gcagcccctc gcccccctcc aaggtggtag atgtacccag ccatgccagt   2520
cagtctgcca ggttcaacaa acacctggat cgcggcttca actcgtgcgc gcgcagcgac   2580
ctgtacttcg tgccactgga gggctccaag ctggccaaga agcgggccga cctggtggag   2640
aaggtgcggc gcgaggccga gcagcgcgcg cgcgaagaaa aggagcgcga gcgcgagcgg   2700
gaacgcgaga aagagcgcga gcgcgagaag gagcgcgagc ttgaacgcag cgtgaagttg   2760
gctcaggagg gccgtgctcc ggtggaatgc ccatctctgg gcccagtgcc ccatcgccct   2820
ccatttgaac cgggcagtgc ggtggctaca gtgccccccct acctgggtcc tgacactcca   2880
gccttgcgca ctctcagtga atatgcccgg cctcatgtca tgtctcctgg caatcgcaac   2940
catccattct acgtgcccct gggggcagtg gacccggggc tcctgggtta caatgtcccg   3000
```

```
gccctgtaca gcagtgatcc agctgcccgg gagagggaac gggaagcccg tgaacgagac   3060

ctccgtgacc gcctcaagcc tggctttgag gtgaagccta gtgagctgga acccctacat   3120

ggggtccctg ggccgggctt ggatcccttt ccccgacatg gggcctggc tctgcagcct    3180

ggcccacctg gcctgcaccc tttccccttt catccgagcc tggggcccct ggagcgagaa   3240

cgtctagcgc tggcagctgg gccagccctg cggcctgaca tgtcctatgc tgagcggctg   3300

gcagctgaga ggcagcacgc agaaagggtg gcggccctgg gcaatgaccc actggcccgg   3360

ctgcagatgc tcaatgtgac tccccatcac caccagcact cccacatcca ctcgcacctg   3420

cacctgcacc agcaagatgc tatccatgca gcctctgcct cggtgcaccc tctcattgac   3480

cccctggcct cagggtctca ccttacccgg atcccctacc cagctggaac tctccctaac   3540

cccctgcttc ctcaccctct gcacgagaac gaagttcttc gtcaccagct ctttgctgcc   3600

ccttaccggg acctgccggc ctccctttct gccccgatgt cagcagctca tcagctgcag   3660

gccatgcacg cacagtcagc tgagctgcag cgcttggcgc tggaacagca gcagtggctg   3720

catgcccatc acccgctgca cagtgtgccg ctgcctgccc aggaggacta ctacagtcac   3780

ctgaagaagg aaagcgacaa gccactgtag aacctgcgat caagagagca ccatggctcc   3840

tacattggac cttggagcac cccaccctc ccccaccgt gcccttggcc tgccacccag    3900

agccaagagg gtgctgctca gttgcagggc ctccgcagct ggacagagag tgggggaggg   3960

agggacagac agaaggccaa ggcccgatgt ggtgtgcaga ggtggggagg tggcgaggat   4020

ggggacagaa agcgcacaga atcttggacc aggtctctct tccttgtccc ccctgctttt   4080

ctcctccccc atgcccaacc cctgtggccg ccgcccctcc cctgccccgt tggtgtgatt   4140

atttcatctg ttagatgtgg ctgttttgcg tagcatcgtg tgccacccct gcccctcccc   4200

gatccctgtg tgcgcgcccc ctctgcaatg tatgcccctt gccccttccc cacactaata   4260

atttatatat ataaatatct atatgacgct cttaaaaaaa catcccaacc aaaaccaacc   4320

aaacaaaaac atcctcacaa ctccccagga aaaaaaaaaa aaaaaaa                 4367
```

```
<210> SEQ ID NO 90
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
```

<222> LOCATION: (19)..(19)
<223> OTHER INFORMATION: n is 5-methylcytosine

<400> SEQUENCE: 90
nugnugnugn ugnugnugnu g 21

<210> SEQ ID NO 91
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine

<400> SEQUENCE: 91
nugcugcugc ugcugcugcu g 21

<210> SEQ ID NO 92
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine

<400> SEQUENCE: 92
cugnugcugn ugcugnugcu g 21

<210> SEQ ID NO 93
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 93
nugcugnugc ugnugcugnu g 21

<210> SEQ ID NO 94
<211> LENGTH: 21
<212> TYPE: RNA

<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine

<400> SEQUENCE: 94
cugcugnugn ugnugcugcu g 21

<210> SEQ ID NO 95
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (10)..(10)
<223> OTHER INFORMATION: n is 5-methylcytosine

<400> SEQUENCE: 95
cugcugcugn ugcugcugcu g 21

<210> SEQ ID NO 96
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 96
nugcugcugc ugcugcugnu g 21

<210> SEQ ID NO 97
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 97
cngcngcngc ngcngcngcn g 21

<210> SEQ ID NO 98
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil

<400> SEQUENCE: 98
cngcugcugc ugcugcugcu g 21

<210> SEQ ID NO 99
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil

<400> SEQUENCE: 99
cugcngcugc ngcugcngcu g 21

<210> SEQ ID NO 100
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (20)..(20)

<223> OTHER INFORMATION: n is 5-methyluracil

<400> SEQUENCE: 100
cngcugcngc ugcngcugcn g 21

<210> SEQ ID NO 101
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil

<400> SEQUENCE: 101
cugcugcngc ngcngcugcu g 21

<210> SEQ ID NO 102
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 102
cngcugcugc ugcugcugcn g 21

<210> SEQ ID NO 103
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil

<400> SEQUENCE: 103
cugcugcngc ugcngcugcu g 21

<210> SEQ ID NO 104
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methyluracil

<400> SEQUENCE: 104
nngnngnngn ngnngnngnn g 21

<210> SEQ ID NO 105
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methylcytosine
<220> FEATURE:

<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methyluracil

<400> SEQUENCE: 105
cugcugnngn ngnngcugcu g 21

<210> SEQ ID NO 106
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine

<400> SEQUENCE: 106
nngcugcugc ugcugcugnn g 21

<210> SEQ ID NO 107
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 107
nugnugnugn ugnugnugnu g 21

<210> SEQ ID NO 108
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 108
nugcugnugc ugnugcugnu g 21

<210> SEQ ID NO 109
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine

<400> SEQUENCE: 109
nugnugnugn ugnugnugnu gnug 24

<210> SEQ ID NO 110

<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil

<400> SEQUENCE: 110
cngcngcngc ngcngcngcn gcng 24

<210> SEQ ID NO 111
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 111
nugnugnugn ugnugnugnu gnugnug 27

<210> SEQ ID NO 112
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil

<400> SEQUENCE: 112
cngcngcngc ngcngcngcn gcngcng 27

<210> SEQ ID NO 113
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:

<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine

<400> SEQUENCE: 113
nugnugnugn ugnugnugnu gnugnugnug 30

<210> SEQ ID NO 114
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil

<400> SEQUENCE: 114
cngcngcngc ngcngcngcn gcngcngcng 30

<210> SEQ ID NO 115
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine
<220> FEATURE:
<221> NAME/KEY: misc_feature
<222> LOCATION: (31)..(31)
<223> OTHER INFORMATION: n is 5-methylcytosine

<400> SEQUENCE: 115
nugnugnugn ugnugnugnu gnugnugnug nug 33

<210> SEQ ID NO 116
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)

<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil
<220> FEATURE:
<221> NAME/KEY: misc_feature
<222> LOCATION: (32)..(32)
<223> OTHER INFORMATION: n is 5-methyluracil

<400> SEQUENCE: 116
cngcngcngc ngcngcngcn gcngcngcng cng 33

<210> SEQ ID NO 117
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine
<220> FEATURE:
<221> NAME/KEY: misc_feature
<222> LOCATION: (31)..(31)
<223> OTHER INFORMATION: n is 5-methylcytosine
<220> FEATURE:
<221> NAME/KEY: misc_feature
<222> LOCATION: (34)..(34)
<223> OTHER INFORMATION: n is 5-methylcytosine

<400> SEQUENCE: 117
nugnugnugn ugnugnugnu gnugnugnug nugnug 36

<210> SEQ ID NO 118
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil
<220> FEATURE:
<221> NAME/KEY: misc_feature
<222> LOCATION: (32)..(32)
<223> OTHER INFORMATION: n is 5-methyluracil
<220> FEATURE:
<221> NAME/KEY: misc_feature
<222> LOCATION: (35)..(35)
<223> OTHER INFORMATION: n is 5-methyluracil

<400> SEQUENCE: 118
cngcngcngc ngcngcngcn gcngcngcng cngcng 36

<210> SEQ ID NO 119
<211> LENGTH: 12
<212> TYPE: RNA
<213> ORGANISM: Artificial
<220> FEATURE:
<223> OTHER INFORMATION: Oligonculeotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine

<400> SEQUENCE: 119
ngnngnngnn gn 12

<210> SEQ ID NO 120
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine

<400> SEQUENCE: 120
ngcngcngcn gc 12

<210> SEQ ID NO 121
<211> LENGTH: 15
<212> TYPE: RNA
<213> ORGANISM: Artificial
<220> FEATURE:
<223> OTHER INFORMATION: Oligoncleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine

<400> SEQUENCE: 121
ngnngnngnn gnngn 15

<210> SEQ ID NO 122
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine

<400> SEQUENCE: 122
ngcngcngcn gcngc 15

<210> SEQ ID NO 123

<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine

<400> SEQUENCE: 123
ngnngnngnn gnngnngn 18

<210> SEQ ID NO 124
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine

<400> SEQUENCE: 124
ngcngcngcn gcngcngc 18

<210> SEQ ID NO 125
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 125
ngnngnngnn gnngnngnng n 21

<210> SEQ ID NO 126
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 126
ngcngcngcn gcngcngcng c 21

<210> SEQ ID NO 127
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 127
ngnngnngnn gnngnngnng nngn 24

<210> SEQ ID NO 128
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)

<223> OTHER INFORMATION: n is 5-methylcytosine

<400> SEQUENCE: 128
ngcngcngcn gcngcngcng cngc 24

<210> SEQ ID NO 129
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature -continued
<222> LOCATION: (25)..(25)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine

<400> SEQUENCE: 129
ngnngnngnn gnngnngnng nngnngn 27

<210> SEQ ID NO 130
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 130
ngcngcngcn gcngcngcng cngcngc 27

<210> SEQ ID NO 131
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:

<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine

<400> SEQUENCE: 131
ngnngnngnn gnngnngnng nngnngnngn 30

<210> SEQ ID NO 132
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine

<400> SEQUENCE: 132
ngcngcngcn gcngcngcng cngcngcngc 30

<210> SEQ ID NO 133
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)

<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine

<400> SEQUENCE: 133
nngnngnngn ng 12

<210> SEQ ID NO 134
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine

<400> SEQUENCE: 134
cngcngcngc ng 12

<210> SEQ ID NO 135
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine

<400> SEQUENCE: 135
nngnngnngn ngnng 15

<210> SEQ ID NO 136
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine

<400> SEQUENCE: 136
cngcngcngc ngcng 15

<210> SEQ ID NO 137
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:

<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine

<400> SEQUENCE: 137
nngnngnngn ngnngnng 18

<210> SEQ ID NO 138
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine

<400> SEQUENCE: 138
cngcngcngc ngcngcng 18

<210> SEQ ID NO 139
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine

<400> SEQUENCE: 139
nngnngnngn ngnngnngnn g 21

<210> SEQ ID NO 140
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (17)..(17)

<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine

<400> SEQUENCE: 140
cngcngcngc ngcngcngcn g 21

<210> SEQ ID NO 141
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine

<400> SEQUENCE: 141
nngnngnngn ngnngnngnn gnng 24

<210> SEQ ID NO 142
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine

<400> SEQUENCE: 142
cngcngcngc ngcngcngcn gcng 24

<210> SEQ ID NO 143
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:

<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (26)..(26)
<223> OTHER INFORMATION: n is 5-methylcytosine

<400> SEQUENCE: 143
nngnngnngn ngnngnngnn gnngnng 27

<210> SEQ ID NO 144
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (20)..(20)
<223> OTHER INFORMATION: n is a, c, g, or u
<220> FEATURE:
<221> NAME/KEY: misc_feature
<222> LOCATION: (23)..(23)
<223> OTHER INFORMATION: n is 5-methylcytosine
<220> FEATURE:
<221> NAME/KEY: misc_feature
<222> LOCATION: (26)..(26)
<223> OTHER INFORMATION: n is 5-methylcytosine

<400> SEQUENCE: 144
cngcngcngc ngcngcngcn gcngcng 27

<210> SEQ ID NO 145
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)

<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (26)..(26)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine
<220> FEATURE:
<221> NAME/KEY: misc_feature
<222> LOCATION: (29)..(29)
<223> OTHER INFORMATION: n is 5-methylcytosine

<400> SEQUENCE: 145
nngnngnngn ngnngnngnn gnngnngnng 30

<210> SEQ ID NO 146
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine
<220> FEATURE:
<221> NAME/KEY: misc_feature
<222> LOCATION: (26)..(26)
<223> OTHER INFORMATION: n is 5-methylcytosine
<220> FEATURE:
<221> NAME/KEY: misc_feature
<222> LOCATION: (29)..(29)
<223> OTHER INFORMATION: n is 5-methylcytosine

<400> SEQUENCE: 146
cngcngcngc ngcngcngcn gcngcngcng 30

<210> SEQ ID NO 147
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine

<400> SEQUENCE: 147
uunuunuunu un 12

<210> SEQ ID NO 148
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil

<400> SEQUENCE: 148
nncnncnncn nc 12

<210> SEQ ID NO 149
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine

<400> SEQUENCE: 149
uunuunuunu unuun 15

<210> SEQ ID NO 150
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil

<400> SEQUENCE: 150
nncnncnncn ncnnc 15

<210> SEQ ID NO 151
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine

<400> SEQUENCE: 151
uunuunuunu unuunuun 18

<210> SEQ ID NO 152
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)

<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil

<400> SEQUENCE: 152
nncnncnncn ncnncnnc 18

<210> SEQ ID NO 153
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 153
uunuunuunu unuunuunuu n 21

<210> SEQ ID NO 154
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 154
nncnncnncn ncnncnncnn c 21

<210> SEQ ID NO 155
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methyluracil
<220> FEATURE:

<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methylcytosine

<400> SEQUENCE: 155
nnnnnnnnnn nnnnnnnnnn n 21

<210> SEQ ID NO 156
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methylcytosine

<400> SEQUENCE: 156
nnnuucuucu ucuucuucnn n 21

<210> SEQ ID NO 157
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)

<223> OTHER INFORMATION: n is 5-methyluracil
<220> FEATURE:
<221> NAME/KEY: misc_feature
<222> LOCATION: (21)..(21)
<223> OTHER INFORMATION: n is 5-methylcytosine

<400> SEQUENCE: 157
nnnuucnnnu ucnnnuucnn n 21

<210> SEQ ID NO 158
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 158
uunuunuunu unuunuunuu nuun 24

<210> SEQ ID NO 159
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil

<400> SEQUENCE: 159
nncnncnncn ncnncnncnn cnnc 24

<210> SEQ ID NO 160
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:

<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine

<400> SEQUENCE: 160
uunuunuunu unuunuunuu nuunuun 27

<210> SEQ ID NO 161
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil

<400> SEQUENCE: 161
nncnncnncn ncnncnncnn cnncnnc 27

<210> SEQ ID NO 162
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine

<400> SEQUENCE: 162
uunuunuunu unuunuunuu nuunuunuun 30

<210> SEQ ID NO 163

<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (28)..(28)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil

<400> SEQUENCE: 163
nncnncnncn ncnncnncnn cnncnncnnc 30

<210> SEQ ID NO 164
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine
<220> FEATURE:
<221> NAME/KEY: misc_feature
<222> LOCATION: (33)..(33)
<223> OTHER INFORMATION: n is 5-methylcytosine

<400> SEQUENCE: 164
uunuunuunu unuunuunuu nuunuunuun uun 33

<210> SEQ ID NO 165
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:

<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (28)..(28)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil
<220> FEATURE:
<221> NAME/KEY: misc_feature
<222> LOCATION: (31)..(31)
<223> OTHER INFORMATION: n is 5-methyluracil

```
<220> FEATURE:
<221> NAME/KEY: misc_feature
<222> LOCATION: (32)..(32)
<223> OTHER INFORMATION: n is 5-methyluracil

<400> SEQUENCE: 165

nncnncnncn ncnncnncnn cnncnncnnc nnc                                    33


<210> SEQ ID NO 166
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine
<220> FEATURE:
<221> NAME/KEY: misc_feature
<222> LOCATION: (33)..(33)
<223> OTHER INFORMATION: n is 5-methylcytosine
<220> FEATURE:
<221> NAME/KEY: misc_feature
<222> LOCATION: (36)..(36)
<223> OTHER INFORMATION: n is 5-methylcytosine

<400> SEQUENCE: 166

uunuunuunu unuunuunuu nuunuunuun uunuun                                 36


<210> SEQ ID NO 167
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
```

<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (28)..(28)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil
<220> FEATURE:
<221> NAME/KEY: misc_feature
<222> LOCATION: (31)..(31)
<223> OTHER INFORMATION: n is 5-methyluracil
<220> FEATURE:
<221> NAME/KEY: misc_feature
<222> LOCATION: (32)..(32)
<223> OTHER INFORMATION: n is 5-methyluracil
<220> FEATURE:
<221> NAME/KEY: misc_feature
<222> LOCATION: (34)..(34)
<223> OTHER INFORMATION: n is 5-methyluracil
<220> FEATURE:
<221> NAME/KEY: misc_feature
<222> LOCATION: (35)..(35)
<223> OTHER INFORMATION: n is 5-methyluracil

<400> SEQUENCE: 167
nncnncnncn ncnncnncnn cnncnncnnc nncnnc 36

<210> SEQ ID NO 168
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine

<400> SEQUENCE: 168
ggnggnggng gn 12

<210> SEQ ID NO 169
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine

<400> SEQUENCE: 169
ggnggnggng gnggn 15

-continued

<210> SEQ ID NO 170
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine

<400> SEQUENCE: 170
ggnggnggng gnggnggn 18

<210> SEQ ID NO 171
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 171
ggnggnggng gnggnggngg n 21

<210> SEQ ID NO 172
<211> LENGTH: 21

<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 172
ggnggcggcg gcggcggcgg n 21

<210> SEQ ID NO 173
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 173
ggnggcggng gcggnggcgg n 21

<210> SEQ ID NO 174
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine

<400> SEQUENCE: 174
ggcggcggng gnggnggcgg c 21

<210> SEQ ID NO 175
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)

<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 175
ggnggnggng gnggnggngg nggn 24

<210> SEQ ID NO 176
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine

<400> SEQUENCE: 176
ggnggnggng gnggnggngg nggnggn 27

<210> SEQ ID NO 177
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine

<400> SEQUENCE: 177
ggnggnggng gnggnggngg nggnggnggn 30

<210> SEQ ID NO 178
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine

<400> SEQUENCE: 178
nggnggnggn gg 12

<210> SEQ ID NO 179
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine

<400> SEQUENCE: 179
nggnggnggn ggngg 15

<210> SEQ ID NO 180
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine

<400> SEQUENCE: 180
nggnggnggn ggnggngg 18

<210> SEQ ID NO 181
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 181
nggnggnggn ggnggnggng g 21

<210> SEQ ID NO 182
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine

<400> SEQUENCE: 182
nggnggnggn ggnggnggng gngg 24

<210> SEQ ID NO 183

<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 183
nggnggnggn ggnggnggng gnggngg 27

<210> SEQ ID NO 184
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine

<400> SEQUENCE: 184
nggnggnggn ggnggnggng gnggnggngg 30

<210> SEQ ID NO 185
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine

<400> SEQUENCE: 185
ngnnungnnu ngnnu 15

<210> SEQ ID NO 186
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:

<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine

<400> SEQUENCE: 186
ngnnungnnu ngnnungnnu 20

<210> SEQ ID NO 187
<211> LENGTH: 20
<212> TYPE: RNA
<213> ORGANISM: Artificial
<220> FEATURE:
<223> OTHER INFORMATION: Oligonucelotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine

<400> SEQUENCE: 187
ngnnuagaau agaaungnnu 20

<210> SEQ ID NO 188
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine

<400> SEQUENCE: 188
ngnnuagaau ngnnuagaau 20

<210> SEQ ID NO 189
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine

<400> SEQUENCE: 189
ngaauagnnu ngaauagnnu 20

<210> SEQ ID NO 190

<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine
<220> FEATURE:
<221> NAME/KEY: misc_feature
<222> LOCATION: (21)..(21)
<223> OTHER INFORMATION: n is 2,6-diaminopurine
<220> FEATURE:
<221> NAME/KEY: misc_feature
<222> LOCATION: (23)..(23)
<223> OTHER INFORMATION: n is 2,6-diaminopurine
<220> FEATURE:
<221> NAME/KEY: misc_feature
<222> LOCATION: (24)..(24)
<223> OTHER INFORMATION: n is 2,6-diaminopurine

<400> SEQUENCE: 190
ngnnungnnu ngnnungnnu ngnnu 25

<210> SEQ ID NO 191
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine
<220> FEATURE:
<221> NAME/KEY: misc_feature
<222> LOCATION: (21)..(21)
<223> OTHER INFORMATION: n is 2,6-diaminopurine
<220> FEATURE:
<221> NAME/KEY: misc_feature
<222> LOCATION: (23)..(23)
<223> OTHER INFORMATION: n is 2,6-diaminopurine
<220> FEATURE:
<221> NAME/KEY: misc_feature
<222> LOCATION: (24)..(24)
<223> OTHER INFORMATION: n is 2,6-diaminopurine
<220> FEATURE:
<221> NAME/KEY: misc_feature
<222> LOCATION: (26)..(26)
<223> OTHER INFORMATION: n is 2,6-diaminopurine
<220> FEATURE:
<221> NAME/KEY: misc_feature
<222> LOCATION: (28)..(28)
<223> OTHER INFORMATION: n is 2,6-diaminopurine
<220> FEATURE:
<221> NAME/KEY: misc_feature
<222> LOCATION: (29)..(29)
<223> OTHER INFORMATION: n is 2,6-diaminopurine

<400> SEQUENCE: 191
ngnnungnnu ngnnungnnu ngnnungnnu 30

<210> SEQ ID NO 192
<211> LENGTH: 35
<212> TYPE: RNA

<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine
<220> FEATURE:
<221> NAME/KEY: misc_feature
<222> LOCATION: (21)..(21)
<223> OTHER INFORMATION: n is 2,6-diaminopurine
<220> FEATURE:
<221> NAME/KEY: misc_feature
<222> LOCATION: (23)..(23)
<223> OTHER INFORMATION: n is 2,6-diaminopurine
<220> FEATURE:
<221> NAME/KEY: misc_feature
<222> LOCATION: (24)..(24)
<223> OTHER INFORMATION: n is 2,6-diaminopurine
<220> FEATURE:
<221> NAME/KEY: misc_feature
<222> LOCATION: (26)..(26)
<223> OTHER INFORMATION: n is 2,6-diaminopurine
<220> FEATURE:
<221> NAME/KEY: misc_feature
<222> LOCATION: (28)..(28)
<223> OTHER INFORMATION: n is 2,6-diaminopurine
<220> FEATURE:
<221> NAME/KEY: misc_feature
<222> LOCATION: (29)..(29)
<223> OTHER INFORMATION: n is 2,6-diaminopurine
<220> FEATURE:
<221> NAME/KEY: misc_feature
<222> LOCATION: (31)..(31)
<223> OTHER INFORMATION: n is 2,6-diaminopurine
<220> FEATURE:
<221> NAME/KEY: misc_feature
<222> LOCATION: (33)..(33)
<223> OTHER INFORMATION: n is 2,6-diaminopurine
<220> FEATURE:
<221> NAME/KEY: misc_feature
<222> LOCATION: (34)..(34)
<223> OTHER INFORMATION: n is 2,6-diaminopurine

<400> SEQUENCE: 192
ngnnungnnu ngnnungnnu ngnnungnnu ngnnu 35

<210> SEQ ID NO 193
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine

<400> SEQUENCE: 193
naggnaggna gg 12

<210> SEQ ID NO 194
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine

<400> SEQUENCE: 194
cnggcnggcn gg 12

<210> SEQ ID NO 195
<211> LENGTH: 16
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)

<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine

<400> SEQUENCE: 195
cnggcnggcn ggcngg 16

<210> SEQ ID NO 196
<211> LENGTH: 16
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine

<400> SEQUENCE: 196
naggnaggna ggnagg 16

<210> SEQ ID NO 197
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine

<400> SEQUENCE: 197
naggnaggna ggnaggnagg 20

<210> SEQ ID NO 198
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine

<400> SEQUENCE: 198
cnggcnggcn ggcnggcngg 20

<210> SEQ ID NO 199
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine

<400> SEQUENCE: 199
naggcaggna ggcaggnagg 20

<210> SEQ ID NO 200
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine

<400> SEQUENCE: 200
cnggcaggcn ggcaggcngg 20

<210> SEQ ID NO 201
<211> LENGTH: 24
<212> TYPE: RNA
<213> ORGANISM: Artificial
<220> FEATURE:
<223> OTHER INFORMATION: Oligonucleotide
<220> FEATURE:

<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 201
naggnaggna ggnaggnagg nagg 24

<210> SEQ ID NO 202
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (22)..(22)
<223> OTHER INFORMATION: n is 2,6-diaminopurine

<400> SEQUENCE: 202
cnggcnggcn ggcnggcngg cngg 24

<210> SEQ ID NO 203
<211> LENGTH: 28
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 203
naggnaggna ggnaggnagg naggnagg 28

<210> SEQ ID NO 204
<211> LENGTH: 28
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (22)..(22)
<223> OTHER INFORMATION: n is 2,6-diaminopurine
<220> FEATURE:
<221> NAME/KEY: misc_feature
<222> LOCATION: (26)..(26)
<223> OTHER INFORMATION: n is 2,6-diaminopurine

<400> SEQUENCE: 204
cnggcnggcn ggcnggcngg cnggcngg 28

<210> SEQ ID NO 205
<211> LENGTH: 32
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)

<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (29)..(29)
<223> OTHER INFORMATION: n is 5-methylcytosine

<400> SEQUENCE: 205
naggnaggna ggnaggnagg naggnaggna gg 32

<210> SEQ ID NO 206
<211> LENGTH: 32
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (22)..(22)
<223> OTHER INFORMATION: n is 2,6-diaminopurine
<220> FEATURE:
<221> NAME/KEY: misc_feature
<222> LOCATION: (26)..(26)
<223> OTHER INFORMATION: n is 2,6-diaminopurine
<220> FEATURE:
<221> NAME/KEY: misc_feature
<222> LOCATION: (30)..(30)
<223> OTHER INFORMATION: n is 2,6-diaminopurine

<400> SEQUENCE: 206
cnggcnggcn ggcnggcngg cnggcnggcn gg 32

<210> SEQ ID NO 207
<211> LENGTH: 36
<212> TYPE: RNA
<213> ORGANISM: Artificial

<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (29)..(29)
<223> OTHER INFORMATION: n is 5-methylcytosine
<220> FEATURE:
<221> NAME/KEY: misc_feature
<222> LOCATION: (33)..(33)
<223> OTHER INFORMATION: n is 5-methylcytosine

<400> SEQUENCE: 207
naggnaggna ggnaggnagg naggnaggna ggnagg 36

<210> SEQ ID NO 208
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (22)..(22)
<223> OTHER INFORMATION: n is 2,6-diaminopurine
<220> FEATURE:
<221> NAME/KEY: misc_feature
<222> LOCATION: (26)..(26)
<223> OTHER INFORMATION: n is 2,6-diaminopurine
<220> FEATURE:

<221> NAME/KEY: misc_feature
<222> LOCATION: (30)..(30)
<223> OTHER INFORMATION: n is 2,6-diaminopurine
<220> FEATURE:
<221> NAME/KEY: misc_feature
<222> LOCATION: (34)..(34)
<223> OTHER INFORMATION: n is 2,6-diaminopurine

<400> SEQUENCE: 208
cnggcnggcn ggcnggcngg cnggcnggcn ggcngg 36

<210> SEQ ID NO 209
<211> LENGTH: 17
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine

<400> SEQUENCE: 209
ggcucnggcu cnggcuc 17

<210> SEQ ID NO 210
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is an abasic monomer
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (10)..(10)
<223> OTHER INFORMATION: n is an abasic monomer
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (16)..(16)
<223> OTHER INFORMATION: n is an abasic monomer
<220> FEATURE:
<221> NAME/KEY: misc_feature
<222> LOCATION: (18)..(18)
<223> OTHER INFORMATION: n is 5-methylcytosine

<400> SEQUENCE: 210
ggcncnggcn cnggcncn 18

<210> SEQ ID NO 211
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine

<400> SEQUENCE: 211
ggcucnggcu cnggcucn 18

<210> SEQ ID NO 212
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 212
ggcucnggcu cnggcucngg cucn 24

<210> SEQ ID NO 213
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is an abasic monomer
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (10)..(10)
<223> OTHER INFORMATION: n is an abasic monomer
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (16)..(16)
<223> OTHER INFORMATION: n is an abasic monomer
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (22)..(22)
<223> OTHER INFORMATION: n is an abasic monomer
<220> FEATURE:
<221> NAME/KEY: misc_feature
<222> LOCATION: (24)..(24)

<223> OTHER INFORMATION: n is 5-methylcytosine

<400> SEQUENCE: 213
ggcncnggcn cnggcncngg cncn 24

<210> SEQ ID NO 214
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (16)..(16)
<223> OTHER INFORMATION: n is inosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (22)..(22)
<223> OTHER INFORMATION: n is inosine
<220> FEATURE:
<221> NAME/KEY: misc_feature
<222> LOCATION: (24)..(24)
<223> OTHER INFORMATION: n is 5-methylcytosine

<400> SEQUENCE: 214
ggcncnggcn cnggcncngg cncn 24

<210> SEQ ID NO 215
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 215
ggccunggcc unggccungg ccun 24

<210> SEQ ID NO 216
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine

<400> SEQUENCE: 216
ggnunnggnu nnggnunn 18

<210> SEQ ID NO 217
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:

<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 217
ggnunnggnu nnggnunngg nunn 24

<210> SEQ ID NO 218
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is inosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is inosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 218
ggnnnnggnn nnggnnnngg nnnn 24

<210> SEQ ID NO 219
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is an abasic monomer
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is an abasic monomer
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is an abasic monomer
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)

<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is an abasic monomer
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 219
ggnnnnggnn nnggnnnngg nnnn 24

<210> SEQ ID NO 220
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is an abasic monomer
<220> FEATURE:
<221> NAME/KEY: misc_feature
<222> LOCATION: (23)..(23)
<223> OTHER INFORMATION: n is an abasic monomer
<220> FEATURE:
<221> NAME/KEY: misc_feature
<222> LOCATION: (24)..(24)
<223> OTHER INFORMATION: n is an abasic monomer
<220> FEATURE:
<221> NAME/KEY: misc_feature
<222> LOCATION: (25)..(25)
<223> OTHER INFORMATION: n is an abasic monomer

<400> SEQUENCE: 220
nugnugnugn ugnugnugnu gnnnn 25

-continued

```
<210> SEQ ID NO 221
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is an abasic monomer
<220> FEATURE:
<221> NAME/KEY: misc_feature
<222> LOCATION: (23)..(23)
<223> OTHER INFORMATION: n is an abasic monomer
<220> FEATURE:
<221> NAME/KEY: misc_feature
<222> LOCATION: (24)..(24)
<223> OTHER INFORMATION: n is an abasic monomer
<220> FEATURE:
<221> NAME/KEY: misc_feature
<222> LOCATION: (25)..(25)
<223> OTHER INFORMATION: n is an abasic monomer

<400> SEQUENCE: 221

nugcugnugc ugnugcugnu gnnnn                                          25
```

RNA MODULATING OLIGONUCLEOTIDES WITH IMPROVED CHARACTERISTICS FOR THE TREATMENT OF NEUROMUSCULAR DISORDERS

CROSS REFERENCE

This application is a continuation application of International Application No. PCT/NL2013/050306 filed Apr. 23, 2013, which claims priority to U.S. Provisional Application No. 61/636,914 filed Apr. 23, 2012 and EP Patent Application No. 12165139.2 filed Apr. 23, 2012, all of the contents of which are hereby incorporated by reference in their entirety.

SEQUENCE LISTING

The attached Sequence Listing is hereby incorporated by reference.

FIELD

The invention relates to the field of human genetics, more specifically neuromuscular disorders. The invention in particular relates to the use of antisense oligonucleotides (AONs) with improved characteristics enhancing clinical applicability as further defined herein.

BACKGROUND OF THE INVENTION

Neuromuscular diseases are characterized by impaired functioning of the muscles due to either muscle or nerve pathology (myopathies and neuropathies). The neuropathies are characterized by neurodegeneration and impaired nerve control leading to problems with movement, spasticity or paralysis. Examples include Huntington's disease (HD), several types of spinocerebellar ataxia (SCA), Friedreich's ataxia (FA), Amyotrophic Lateral Sclerosis (ALS) and Frontotemporal dementia (FTD). A subset of neuropathies is caused by a cis-element repeat instability. For instance, HD is caused by a triplet (CAG)n repeat expansion in exon 1 of the HTT gene. Expansion of these repeats results in expansion of a glutamine stretch at the N-terminal end of the 348 kDa cytoplasmic huntingtin protein. Huntingtin has a characteristic sequence of 6 to 29 glutamine amino acid residues in the normal form; the mutated huntingtin causing the disease has more than 38 residues. The continuous expression of mutant huntingtin molecules in neuronal cells results in the formation of large protein deposits which eventually give rise to cell death, especially in the frontal lobes and the basal ganglia (mainly in the caudate nucleus). The severity of the disease is generally proportional to the number of extra residues. AONs specifically targeting the expanded CAG repeats (such as PS57 $(CUG)_7$ as a 2'-O-methyl phosphorothioate RNA; SEQ ID NO:1 Evers et al.) can be applied to effectively reduce mutant huntingtin transcript and (toxic) protein levels in HD patient-derived cells. For treatment of neuropathies, systemically administered AONs need to pass the blood brain barrier. Thus, there is a need for optimization of oligochemistry allowing and/or exhibiting improved brain delivery.

The myopathies include genetic muscular dystrophies that are characterized by progressive weakness and degeneration of skeletal, heart and/or smooth muscle. Examples of myopathies are Duchenne muscular dystrophy (DMD), myotonic dystrophy type 1 (DM1), and myotonic dystrophy type 2 (DM2). DM1 and DM2 are both also caused by cis-element repeat instability; DM1 by a trinucleotide $(CTG)_n$ repeat expansion in the 3' untranslated region of exon 15 in the DMPK gene, and DM2 by a tetranucleotide $(CCTG)_n$ repeat expansion in the DM2/ZNF9 gene. Also here, AONs specifically targeting the expanded repeats, such as PS58, $(CAG)_7$, a 2'-O-methyl phosphorothioate RNA for DM1 (Mulders et al.), have been shown to efficiently induce the specific degradation of the (toxic) expanded repeat transcripts. In contrast to DMD where the gene defect is associated with increased permeability of the muscle fiber membranes for small compounds as AONs, for most other myopathies an enhanced AON distribution to and uptake by muscle tissue is essential to obtain a therapeutic effect. Thus, also here there is a need for optimization of oligochemistry allowing and/or exhibiting improved muscle delivery.

The particular characteristics of a chosen chemistry at least in part affect the delivery of an AON to the target transcript: administration route, biostability, biodistribution, intra-tissue distribution, and cellular uptake and trafficking. In addition, further optimization of oligonucleotide chemistry is conceived to enhance binding affinity and stability, enhance activity, improve safety, and/or to reduce cost of goods by reducing length or improving synthesis and/or purification procedures. Multiple chemical modifications have become generally and/or commercially available to the research community (such as 2'-O-methyl RNA and 5-substituted pyrimidines and 2,6-diaminopurines), whereas most others still present significant synthetic effort to obtain. Especially preliminary encouraging results have been obtained using 2'-O-methyl phosphorothioate RNA containing modifications on the pyrimidine and purine bases as identified herein.

In conclusion, to enhance the therapeutic applicability of AONs for treating human cis-element repeat instability associated genetic disorders as exemplified herein, there is a need for AONs with further improved characteristics.

DESCRIPTION OF THE INVENTION

Oligonucleotide

In a first aspect, the invention provides an oligonucleotide comprising 2'-O-methyl RNA nucleotide residues, having a backbone wherein at least one phosphate moiety is replaced by a phosphorothioate moiety, and comprising one or more 5-methylpyrimidine and/or one or more 2,6-diaminopurine bases; or an oligonucleotide consisting of 2'-O-methyl RNA nucleotide residues and having a backbone wherein all phosphate moieties are replaced by phosphorothioate moieties, and comprising one or more 5-methylpyrimidine and/or one or more 2,6-diaminopurine bases, for use as a medicament for treating human cis-element repeat instability associated genetic disorders.

In the context of the invention, "backbone" is used to identify the chain of alternating ribose rings and internucleoside linkages, to which the nucleobases are attached. The term "linkage" is used for the connection between two ribose units (i.e. "internucleoside linkage"), which is generally a phosphate moiety. Thus, an oligonucleotide having 10 nucleotides may contain 9 linkages, linking the 10 ribose units together. Additionally, there may be one or more last linkage(s) present at one or both sides of the oligonucleotide, which is only connected to one nucleotide. The terms "linkage" and "internucleoside linkage" are also meant to indicate such a pendant linkage. At least one of the linkages in the backbone of the oligonucleotide according to the invention consists of a phosphorothioate moiety, linking two ribose units. Thus, at least one of the naturally occurring 3' to 5' phosphodiester moieties present in RNA is replaced by a phosphorothioate moiety.

Within the context of the invention, "a" in each of the following expressions means "at least one": a 2'-O-methyl RNA nucleotide residue, a 2'-O-methyl RNA residue, a phosphorothioate moiety, a 2'-O-methyl phosphorothioate RNA residue, a 5-methylpyrimidine base, a 5-methylcytosine base, a 5-methyluracil base, a thymine base, a 2,6-diaminopurine base.

Preferably, the oligonucleotide according to the invention is an oligonucleotide with less than 37 nucleotides. Said oligonucleotide may have 12, 13, 14, 15, 16, 17, 18, 19, 20, 21, 22, 23, 24, 25, 26, 27, 28, 29, 30, 31, 32, 33, 34, 35, or 36 nucleotides. Such oligonucleotide may also be identified as an oligonucleotide having from 12 to 36 nucleotides.

Accordingly, an oligonucleotide of the invention, comprising a 2'-O-methyl RNA nucleotide residue having a backbone wherein at least one phosphate moiety is replaced by a phosphorothioate moiety, comprises less than 37 nucleotides (i.e. it comprises 12, 13, 14, 15, 16, 17, 18, 19, 20, 21, 22, 23, 24, 25, 26, 27, 28, 29, 30, 31, 32, 33, 34, 35 or 36 nucleotides) and a 5-methylpyrimidine and/or a 2,6-diaminopurine base.

Accordingly, an oligonucleotide of the invention, consisting of 2'-O-methyl RNA nucleotide residues and having a backbone wherein all phosphate moieties are replaced by phosphorothioate, and comprises less than 34 nucleotides (i.e. it comprises 12, 13, 14, 15, 16, 17, 18, 19, 20, 21, 22, 23, 24, 25, 26, 27, 28, 29, 30, 31, 32, 33, 34, 35 or 36 nucleotides) and a 5-methylpyrimidine and/or a 2,6-diaminopurine base.

In a preferred embodiment, the oligonucleotide of the invention comprises a 2'-O-methyl phosphorothioate RNA nucleotide residue, or consists of 2'-O-methyl phosphorothioate RNA nucleotide residues. Such oligonucleotide comprises a 2'-O-methyl RNA residue, which is connected through a phosphorothioate linkage to the next nucleotide in the sequence. This next nucleotide may be, but not necessarily, another 2'-O-methyl phosphorothioate RNA nucleotide residue. Alternatively, such oligonucleotide consists of 2'-O-methyl phosphorothioate RNA nucleotide residues, wherein all nucleotides comprise a 2'-O-methyl moiety and a phosphorothioate moiety. Preferably, such oligonucleotide consists of 2'-O-methyl phosphorothioate RNA nucleotide residues. Such chemistry is known to the skilled person. Throughout the application, an oligonucleotide comprising a 2'-O-methyl RNA residue and a phosphorothioate linkage may be replaced by an oligonucleotide comprising a 2'-O-methyl phosphorothioate RNA nucleotide residue or an oligonucleotide comprising a 2'-O-methyl phosphorothioate RNA residue. Throughout the application, an oligonucleotide consisting of 2'-O-methyl RNA residues linked by or connected through phosphorothioate linkages or an oligonucleotide consisting of 2'-O-methyl phosphorothioate RNA nucleotide residues may be replaced by an oligonucleotide consisting of 2'-O-methyl phosphorothioate RNA.

In addition, an oligonucleotide of the invention comprises at least one base modification that increases binding affinity to target strands, increases melting temperature of the resulting duplex of said oligonucleotide with its target, and/or decreases immunostimulatory effects, and/or increases biostability, and/or improves biodistribution and/or intra-tissue distribution, and/or cellular uptake and trafficking. In an embodiment, an oligonucleotide of the invention comprises a 5-methylpyrimidine and/or a 2,6-diaminopurine base. A 5-methylpyrimidine base is selected from a 5-methylcytosine and/or a 5-methyluracil and/or a thymine, in which thymine is identical to 5-methyluracil. Where an oligonucleotide of the invention has two or more such base modifications, said base modifications may be identical, for example all such modified bases in the oligonucleotide are 5-methylcytosine, or said base modifications may be combinations of different base modifications, for example the oligonucleotide may have one or more 5-methylcytosines and one or more 5-methyluracils.

In a preferred embodiment, an oligonucleotide of the invention (i.e. an oligonucleotide comprising 2'-O-methyl RNA nucleotide residues, having a backbone wherein at least one phosphate moiety is replaced by a phosphorothioate moiety, and comprising one or more 5-methylpyrimidine and/or one or more 2,6-diaminopurine bases; or an oligonucleotide consisting of 2'-O-methyl RNA nucleotide residues and having a backbone wherein all phosphate moieties are replaced by phosphorothioate moieties, and comprising one or more 5-methylpyrimidine and/or one or more 2,6-diaminopurine bases) is such that it does not comprise a 2'-deoxy 2'-fluoro nucleotide (i.e. 2'-deoxy 2'-fluoro-adenosine, -guanosine, -uridine and/or -cytidine). Such oligonucleotide comprising a 2'-fluoro (2'-F) nucleotide has been shown to be able to recruit the interleukin enhancer-binding factor 2 and 3 (ILF2/3) and is thereby able to induce exon skipping in the targeted pre-mRNA (Rigo F, et al, WO2011/097614). In the current invention, the oligonucleotide used preferably does not recruit such factors and/or the oligonucleotide of the invention does not form heteroduplexes with RNA that are specifically recognized by the ILF2/3. The mechanism of action of the oligonucleotide of the current invention is assumed to be distinct from the one of an oligonucleotide with a 2'-F nucleotide: the oligonucleotide of the invention is expected to primarily induce the specific degradation of the (toxic) expanded repeat transcripts.

'Thymine' and '5-methyluracil' may be interchanged throughout the document. In analogy, 2,6-diaminopurine is identical to 2-aminoadenine and these terms may be interchanged throughout the document.

The term "base modification" or "modified base" as identified herein refers to the modification of a naturally occurring base in RNA (i.e. pyrimidine or purine base) or to the de novo synthesis of a base. This de novo synthesized base could be qualified as "modified" by comparison to an existing base.

An oligonucleotide of the invention comprising a 5-methylcytosine and/or a 5-methyluracil and/or a 2,6-diaminopurine base means that at least one of the cytosine nucleobases of said oligonucleotide has been modified by substitution of the proton at the 5-position of the pyrimidine ring with a methyl group (i.e. a 5-methylcytosine), and/or that at least one of the uracil nucleobases of said oligonucleotide has been modified by substitution of the proton at the 5-position of the pyrimidine ring with a methyl group (i.e. a 5-methyluracil), and/or that at least one of the adenine nucleobases of said oligonucleotide has been modified by substitution of the proton at the 2-position with an amino group (i.e. a 2,6-diaminopurine), respectively. Within the context of the invention, the expression "the substitution of a proton with a methyl group in position 5 of the pyrimidine ring" may be replaced by the expression "the substitution of a pyrimidine with a 5-methylpyrimidine," with pyrimidine referring to only uracil, only cytosine or both. Likewise, within the context of the invention, the expression "the substitution of a proton with an amino group in position 2 of adenine" may be replaced by the expression "the substitution of an adenine with a 2,6-diaminopurine." If said oligonucleotide comprises 1, 2, 3, 4, 5, 6, 7, 8, 9 or more cytosines, uracils, and/or adenines, at least 1, 2, 3, 4, 5, 6, 7, 8, 9 or more cytosines, uracils and/or adenines respectively have been modified this way. Preferably all cytosines, uracils and/or adenines have been modified this way or replaced by 5-methylcytosine, 5-methyluracil and/or 2,6-diaminopurine, respectively. No need to say that the invention could only be applied to oligonucleotides comprising at least one cytosine, uracil, or adenine, respectively, in their sequence.

We discovered that the presence of a 5-methylcytosine, 5-methyluracil and/or a 2,6-diaminopurine in an oligonucleotide of the invention has a positive effect on at least one of the parameters or an improvement of at least one parameters of said oligonucleotides. In this context, parameters may include: binding affinity and/or kinetics, silencing activity, biostability, (intra-tissue) distribution, cellular uptake and/or trafficking, and/or immunogenicity of said oligonucleotide, as explained below.

Binding affinity and kinetics depend on the AON's thermodynamic properties. These are at least in part determined by the melting temperature of said oligonucleotide (Tm; calculated with e.g. the oligonucleotide properties calculator (http://www.unc.edu/~cail/biotool/oligo/index.html or http://eu.idtdna.com/analyzer/Applications/OligoAnalyzer/) for single stranded RNA using the basic Tm and the nearest neighbor model), and/or the free energy of the oligonucleotide-target exon complex (using RNA structure version 4.5 or RNA mfold version 3.5). If a Tm is increased, the exon skipping activity typically increases, but when a Tm is too high, the AON is expected to become less sequence-specific. An acceptable Tm and free energy depend on the sequence of the oligonucleotide. Therefore, it is difficult to give preferred ranges for each of these parameters.

An activity of an oligonucleotide of the invention is to inhibit the formation of a mutant protein and/or silence or reduce or decrease the quantity of a disease-associated or disease-causing or mutant transcript containing an extended or unstable number of repeats in a cell of a patient, in a tissue of a patient and/or in a patient as explained later herein. An oligonucleotide of the invention comprising or consisting of a 2'-O-methyl phosphorothioate RNA and a 5-methylcytosine and/or a 5-methyluracil and/or a 2,6-diaminopurine base is expected to be able to silence or reduce or decrease the quantity of said transcript more efficiently than what an oligonucleotide comprising or consisting of a 2'-O-methyl phosphorothioate RNA but without any 5-methylcytosine, without any 5-methyluracil and without any 2,6-diaminopurine base will do. This difference in terms of efficiency may be of at least 1%, 5%, 10%, 15%, 20%, 25%, 30%, 35%, 40%, 45%, 50%, 55%, 60%, 65%, 70%, 75%, 80%, 85%, 90%, 95%, 100%. The reduction or decrease may be assessed by Northern Blotting or (semi-) quantitative RT-PCR for transcript levels (preferably as carried out in the experimental part) or by Western blotting for protein levels. An oligonucleotide of the invention may first be tested in the cellular system like patient-derived fibroblasts as described in Example 1.

Biodistribution and biostability are preferably at least in part determined by a validated hybridization ligation assay adapted from Yu et al., 2002. In an embodiment, plasma or homogenized tissue samples are incubated with a specific capture oligonucleotide probe. After separation, a DIG-labeled oligonucleotide is ligated to the complex and detection followed using an anti-DIG antibody-linked peroxidase. Non-compartmental pharmacokinetic analysis is performed using WINNONLIN software package (model 200, version 5.2, Pharsight, Mountainview, Calif.). Levels of AON (ug) per mL plasma or mg tissue are monitored over time to assess area under the curve (AUC), peak concentration ($C_{max}$), time to peak concentration ($T_{max}$), terminal half life and absorption lag time ($t_{lag}$). Such a preferred assay has been disclosed in the experimental part.

AONs may stimulate an innate immune response by activating the Toll-like receptors (TLR), including TLR9 and TLR7 (Krieg et al., 1995). The activation of TLR9 typically occurs due to the presence of non-methylated CG sequences present in oligodeoxynucleotides (ODNs), by mimicking bacterial DNA which activates the innate immune system through TLR9-mediated cytokine release. The 2'-O-methyl modification is however suggested to markedly reduce such possible effect. TLR7 has been described to recognize uracil repeats in RNA (Diebold et al., 2006).

Activation of TLR9 and TLR7 result in a set of coordinated immune responses that include innate immunity (macrophages, dendritic cells (DC), and NK cells)(Krieg et al., 1995; Krieg, 2000). Several chemo- and cytokines, such as IP-10, TNFα, IL-6, MCP-1 and IFNα (Wagner, 1999; Popovic et al., 2006) have been implicated in this process. The inflammatory cytokines attract additional defensive cells from the blood, such as T and B cells. The levels of these cytokines can be investigated by in vitro testing. In short, human whole blood is incubated with increasing concentrations of AONs after which the levels of the cytokines are determined by standard commercially available ELISA kits. A decrease in immunogenicity preferably corresponds to a detectable decrease of concentration of at least one of the cytokines mentioned above by comparison to the concentration of corresponding cytokine in an assay in a cell treated with an oligonucleotide comprising at least one 5-methylcytosine and/or 5-methyluracil, and/or 2,6-diaminopurine compared to a cell treated with a corresponding oligonucleotide having no 5-methylcytosines, 5-methyluracils, or 2,6-diaminopurines.

Accordingly, a preferred oligonucleotide of the invention has an improved parameter, such as an acceptable or a decreased immunogenicity and/or a better biodistribution and/or acceptable or improved RNA binding kinetics and/or thermodynamic properties by comparison to a corresponding oligonucleotide consisting of a 2'-O-methyl phosphorothioate RNA without a 5-methylcytosine, without a 5-methyluracil and without a 2,6-diaminopurine. Each of these parameters could be assessed using assays known to the skilled person or preferably as disclosed herein.

Below other chemistries and modifications of the oligonucleotide of the invention are defined. These additional chemistries and modifications may be present in combination with the chemistry already defined for said oligonucleotide, i.e. the presence of a 5-methylcytosine, a 5-methyluracil and/or a 2,6-diaminopurine, and the oligonucleotide comprising or consisting of 2'-O-methyl phosphorothioate RNA.

A preferred oligonucleotide of the invention comprises or consists of an RNA molecule or a modified RNA molecule. In a preferred embodiment, an oligonucleotide is single stranded. The skilled person will understand that it is however possible that a single stranded oligonucleotide may form an internal double stranded structure. However, this oligonucleotide is still named a single stranded oligonucleotide in the context of this invention. A single stranded oligonucleotide has several advantages compared to a double stranded siRNA oligonucleotide: (i) its synthesis is expected to be easier than two complementary siRNA strands; (ii) there is a wider range of chemical modifications possible to enhance uptake in cells, a better (physiological) stability and to decrease potential generic adverse effects; (iii) siRNAs have a higher potential for non-specific effects (including off-target genes) and exaggerated pharmacology (e.g. less control possible of effectiveness and selectivity by treatment schedule or dose) and (iv) siRNAs are less likely to act in the nucleus and cannot be directed against introns.

In addition to the modifications described above, the oligonucleotide of the invention may comprise further modifications such as different types of nucleic acid nucleotide residues or nucleotides as described below. Different types of nucleic acid nucleotide residues may be used to generate an oligonucleotide of the invention. Said oligonucleotide may have at least one backbone modification (internucleoside linkage and/or sugar modification) and/or at least one base modification compared to an RNA-based oligonucleotide.

A base modification includes a modified version of the natural purine and pyrimidine bases (e.g. adenine, uracil, guanine, cytosine, and thymine), such as hypoxanthine (e.g. inosine), orotic acid, agmatidine, lysidine, pseudouracil, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; $N^2$-cyclopentylguanine (cPent-G), $N^2$-cyclopentyl-2-aminopurine (cPent-AP), and $N^2$-propyl-2-aminopurine (Pr-AP), or derivatives thereof; and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G and Super T can be found in U.S. Pat. No. 6,683,173 (Epoch Biosciences), which is incorporated here entirely by reference. cPent-G, cPent-AP and Pr-AP were shown to reduce immunostimulatory effects when incorporated in siRNA (Peacock H. et al.).

In an embodiment, an oligonucleotide of the invention comprises an abasic site or an abasic monomer. Within the context of the invention, such monomer may be called an abasic site or an abasic monomer. An abasic monomer or abasic site is a nucleotide residue or building block that lacks a nucleobase by comparison to a corresponding nucleotide residue comprising a nucleobase. Within the invention, an abasic monomer is thus a building block part of an oligonucleotide but lacking a nucleobase. Such abasic monomer may be present or linked or attached or conjugated to a free terminus of an oligonucleotide.

In a more preferred embodiment, an oligonucleotide of the invention comprises 1-10 or more abasic monomers. Therefore, 1, 2, 3, 4, 5, 6, 7, 8, 9, 10 or more abasic monomers may be present in an oligonucleotide of the invention.

An abasic monomer may be of any type known and conceivable by the skilled person, non-limiting examples of which are depicted below:

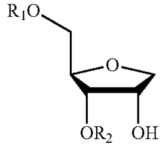
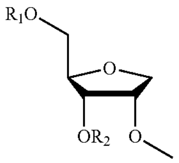
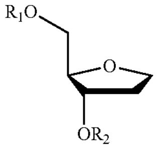
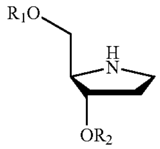
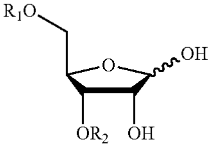
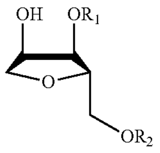
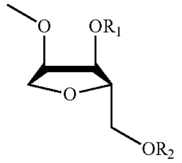
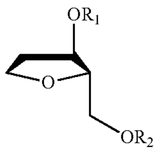
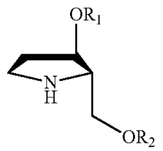
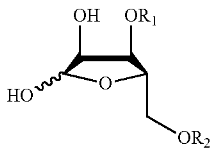
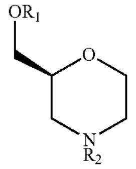
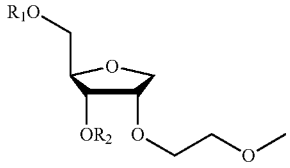
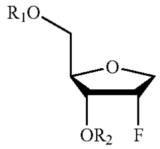
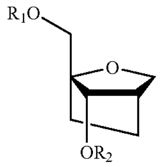
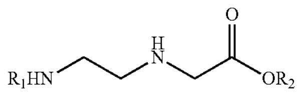
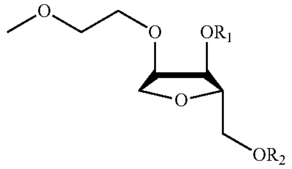
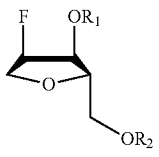
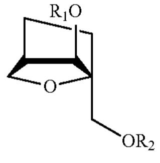

Herein, $R_1$ and $R_2$ are independently H, an oligonucleotide or other abasic site(s), provided that not both $R_1$ and $R_2$ are H and $R_1$ and $R_2$ are not both an oligonucleotide. An abasic monomer(s) can be attached to either or both termini of the oligonucleotide as specified before. It should be noted that an oligonucleotide attached to one or two an abasic site(s) or abasic monomer(s) may comprise less than 12 nucleotides. In this respect, the oligonucleotide according to the invention may comprise at least 12 nucleotides, optionally including one or more abasic sites or abasic monomers at one or both termini.

In the sequence listing, an oligonucleotide of the invention comprising an abasic monomer may be represented by its nucleotide or base sequence; the abasic monomer not being represented since it may be considered as linked or attached or conjugated to a free terminus of an oligonucleotide. This is the case for base sequences SEQ ID NO: 107 and 108. In table 2, the full sequence of preferred oligonucleotides comprising SEQ ID NO:107 or 108 is provided: such oligonucleotide comprises SEQ ID NO: 107 or 108 and 4 abasic monomers at the 3' terminus of the corresponding SEQ ID NO: 107 or 108. SEQ ID NO: 220 and 221 correspond to SEQ ID NO: 107 and 108 further comprising 4 additional abasic monomers at the 3' terminus of the oligonucleotide.

When an abasic monomer is present within a base sequence of an oligonucleotide, said abasic monomer is identified in the sequence listing as part of the sequence of said oligonucleotide as in SEQ ID NO:210 and 213.

In tables 1 and 2, an abasic monomer is identified using the letter Q.

Depending on its length an oligonucleotide of the invention may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 base modifications. It is also encompassed by the invention to introduce more than one distinct base modification in said oligonucleotide.

A "sugar modification" indicates the presence of a modified version of the ribosyl moiety as naturally occurring in RNA (i.e. the furanosyl moiety), such as bicyclic sugars, tetrahydropyrans, morpholinos, 2'-modified sugars, 4'-modified sugars, 5'-modified sugars, and 4'-substituted sugars. Examples of suitable sugar modifications include, but are not limited to, 2'-O-modified RNA nucleotide residues, such as 2'-O-alkyl or 2'-O-(substituted)alkyl e.g. 2'-O-methyl, 2'-O-(2-cyanoethyl), 2'-O-(2-methoxyl)ethyl (2'-MOE), 2'-O-(2-thiomethyl)ethyl, 2'-O-butyryl, 2'-O-propargyl, 2'-O-allyl, 2'-O-(2-amino)propyl, 2'-O-(2-(dimethylamino) propyl), 2'-O-(2-amino)ethyl, 2'-O-(2-(dimethylamino) ethyl); 2'-deoxy (DNA); 2'-O-(haloalkoxy)methyl (Arai K. et al.) e.g. 2'-O-(2-chloroethoxyl)methyl (MCEM), 2'-O-(2, 2-dichloroethoxy)methyl (DCEM); 2'-O-alkoxycarbonyl e.g. 2'-O-[2-(methoxycarbonyl)ethyl] (MOCE), 2'-O-[2-(N-methylcarbamoyl)ethyl] (MCE), 2'-O-[2-(N,N-dimethylcarbamoyl)ethyl] (DCME); 2'-halo e.g. 2'-F, FANA (2'-F arabinosyl nucleic acid); carbasugar and azasugar modifications; 3'-O-alkyl e.g. 3'-O-methyl, 3'-O-butyryl, 3'-O-propargyl, 5'-alkyl e.g. 5'-methyl; and their derivatives. Another sugar modification includes "bridged" or "bicylic" nucleic acid (BNA), e.g. locked nucleic acid (LNA), xcylo-LNA, α-L-LNA, β-D-LNA, cEt (2'-O,4'-C constrained ethyl) LNA, cMOEt (2'-O,4'-C constrained methoxyethyl) LNA, ethylene-bridged nucleic acid (ENA), $BNA^{NC}$[N-Me] (as described in Chem. Commun 2007, 3765, which is incorporated in its entirety by reference); tricyclo DNA (tcDNA); unlocked nucleic acid (UNA); 5'-methyl substituted BNAs (as described in U.S. patent application Ser. No. 13/530,218, which is incorporated in its entirety by reference); cyclohexenyl nucleic acid (CeNA), altriol nucleic acid (ANA), hexitol nucleic acid (HNA), fluorinated HNA (F-HNA), pyranosyl-RNA (p-RNA), 3'-deoxypyranosyl-DNA (p-DNA); morpholino (as e.g. in PMO, PMOPlus, PMO-X) and their derivatives, preferably locked nucleic acid (LNA), xylo-LNA, α-L-LNA, β-D-LNA, cEt (2'-O, 4'-C constrained ethyl) LNA, cMOEt (2'-O,4'-C constrained methoxyethyl) LNA, ethylene-bridged nucleic acid (ENA), tricyclo DNA (tcDNA); cyclohexenyl nucleic acid (CeNA), altriol nucleic acid (ANA), hexitol nucleic acid (HNA), fluorinated HNA (F-HNA), pyranosyl-RNA (p-RNA), 3'-deoxypyranosyl-DNA (p-DNA); morpholino (as e.g. in PMO, PMOPlus, PMO-X) and their derivatives. A preferred tcDNA is tc-PS-DNA (tricyclo DNA comprising phosphorothioate internucleoside linkage). Depending on its length, an oligonucleotide of the invention may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 sugar modifications. It is also encompassed by the invention to introduce more than one distinct sugar modification in said oligonucleotide. In an embodiment, an oligonucleotide as defined herein comprises or consists of an LNA or a derivative thereof. BNA derivatives are for example described in WO 2011/097641, which is incorporated in its entirety by reference. In a more preferred embodiment, an oligonucleotide of the invention is fully 2'-O-methyl modified. Examples of PMO-X are described in WO2011150408, which is incorporated here in its entirety by reference.

In a preferred embodiment, the oligonucleotide according to the invention comprises, apart from the mandatory 2'-O-methyl sugar modification, at least one other sugar modification selected from 2'-O-methyl, 2'-O-(2-methoxyl)ethyl, morpholino, a bridged nucleotide or BNA, or the oligonucleotide comprises both bridged nucleotides and 2'-deoxy modified nucleotides (BNA/DNA mixmers). More preferably, the oligonucleotide according to the invention is modified over its full length with a sugar modification selected from 2'-O-methyl, 2'-O-(2-methoxyl)ethyl, morpholino, bridged nucleic acid (BNA) or BNA/DNA mixmer.

In a more preferred embodiment, the oligonucleotide according to the invention comprises is fully 2'-O-methyl modified, preferably fully 2'-O-methyl phosphorothioate modified.

A "backbone modification" indicates the presence of a modified version of the ribosyl moiety ("sugar modification"), as indicated above, and/or the presence of a modified version of the phosphodiester as naturally occurring in RNA ("internucleoside linkage modification"). Examples of internucleoside linkage modifications, which are compatible with the present invention, are phosphorothioate (PS), chirally pure phosphorothioate, phosphorodithioate (PS2), phosphonoacetate (PACE), phosphonoacetamide (PACA), thiophosphonoacetate, thiophosphonoacetamide, phosphorothioate prodrug, H-phosphonate, methyl phosphonate, methyl phosphonothioate, methyl phosphate, methyl phosphorothioate, ethyl phosphate, ethyl phosphorothioate, boranophosphate, boranophosphorothioate, methyl boranophosphate, methyl boranophosphorothioate, methyl boranophosphonate, methyl boranophosphonothioate, and their derivatives. Another modification includes phosphoramidite, phosphoramidate, N3'→P5' phosphoramidate, phosphordiamidate, phosphorothiodiamidate, sulfamate, dimethylenesulfoxide, sulfonate, triazole, oxalyl, carbamate, methyleneimino (MMI), and thioacetamido nucleic acid (TANA); and their derivatives. Depending on its length, an oligonucleotide of the invention may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 backbone modifications. It is also encompassed by the invention to introduce more than one distinct backbone modification in said oligonucleotide.

An oligonucleotide of the invention comprises at least one phosphorothioate modification. In a more preferred embodiment, an oligonucleotide of the invention is fully phosphorothioate modified.

Other chemical modifications of an oligonucleotide of the invention include peptide-base nucleic acid (PNA), boron-cluster modified PNA, pyrrolidine-based oxy-peptide nucleic acid (POPNA), glycol- or glycerol-based nucleic acid (GNA), threose-based nucleic acid (TNA), acyclic threoninol-based nucleic acid (aTNA), morpholino-based oligonucleotide (PMO, PPMO, PMO-X), cationic morpholino-based oligomers (PMOPlus), oligonucleotides with integrated bases and backbones (ONIBs), pyrrolidine-amide oligonucleotides (POMs); and their derivatives.

In another embodiment, an oligonucleotide comprises a peptide nucleic acid and/or a morpholino phosphorodiamidate or a derivative thereof.

Thus, the preferred oligonucleotide according to one aspect of the invention comprises:

(a) at least one base modification selected from 5-methylpyrimidine and 2,6-diaminopurine; and/or
(b) at least one sugar modification, which is 2'-O-methyl, and/or
(c) at least one backbone modification, which is phosphorothioate.

Thus, a preferred oligonucleotide according to this aspect of the invention comprises a base modification (a) and no sugar modification (b) and no backbone modification (c). Another preferred oligonucleotide according to this aspect of the invention comprises a sugar modification (b) and no base modification (a) and no backbone modification (c). Another preferred oligonucleotide according to this aspect of the invention comprises a backbone modification (c) and no base modification (a) and no sugar modification (b). Also oligonucleotides having none of the above-mentioned modifications are understood to be covered by the present invention, as well as oligonucleotides comprising two, i.e. (a) and (b), (a) and (c) and/or (b) and (c), or all three of the modifications (a), (b) and (c), as defined above. In another preferred embodiment, any of the oligonucleotides as described in the previous paragraph may comprise:

(a) at least one (additional) base modification selected from 2-thiouracil, 2-thiothymine, 5-methylcytosine, 5-methyluracil, thymine, 2,6-diaminopurine; and/or
(b) at least one (additional) sugar modification selected from 2'-O-methyl, 2'-O-(2-methoxyl)ethyl, 2'-deoxy (DNA), morpholino, a bridged nucleotide or BNA, or the oligonucleotide comprises both bridged nucleotides and 2'-deoxy modified nucleotides (BNA/DNA mixmers); and/or
(c) at least one (additional) backbone modification selected from (another) phosphorothioate or phosphordiamidate.

In another preferred embodiment, the oligonucleotide according to the invention is modified over its entire length with one or more of the same modification, selected from (a) one of the base modifications; and/or (b) one of the sugar modifications; and/or (c) one of the backbone modifications.

With the advent of nucleic acid mimicking technology, it has become possible to generate molecules that have a similar, preferably the same hybridization characteristics in kind not necessarily in amount as nucleic acid itself. Such functional equivalents are of course also suitable for use in the invention.

The skilled person will understand that not each sugar, base, and/or backbone may be modified the same way. Several distinct modified sugars, bases and/or backbones may be combined into one single oligonucleotide of the invention.

A person skilled in the art will also recognize that there are many synthetic derivatives of oligonucleotides.

Preferably, said oligonucleotide comprises RNA, as RNA/RNA duplexes are very stable. It is preferred that an RNA oligonucleotide comprises a modification providing the RNA with an additional property, for instance resistance to endonucleases, exonucleases, and RNaseH, additional hybridisation strength, increased stability (for instance in a bodily fluid), increased or decreased flexibility, increased activity, reduced toxicity, increased intracellular transport, tissue-specificity, etc. In addition, the mRNA complexed with the oligonucleotide of the invention is preferably not susceptible to RNaseH cleavage. Preferred modifications have been identified above. Oligonucleotides containing at least in part naturally occurring DNA nucleotides are useful for inducing degradation of DNA-RNA hybrid molecules in the cell by RNase H activity (EC.3.1.26.4).

Naturally occurring RNA ribonucleotides or RNA-like synthetic ribonucleotides comprising oligonucleotides are encompassed herein to form double stranded RNA-RNA hybrids that act as enzyme-dependent antisense through the RNA interference or silencing (RNAi/siRNA) pathways, involving target RNA recognition through sense-antisense strand pairing followed by target RNA degradation by the RNA-induced silencing complex (RISC).

Alternatively or in addition, an oligonucleotide can interfere with the processing or expression of precursor RNA or messenger RNA (steric blocking, RNaseH independent processes) in particular but not limited to RNA splicing and exon skipping, by binding to a target sequence of RNA transcript and getting in the way of processes such as translation or blocking of splice donor or splice acceptor sites. Moreover, the oligonucleotide may inhibit the binding of proteins, nuclear factors and others by steric hindrance and/or interfere with the authentic spatial folding of the target RNA and/or bind itself to proteins that originally bind to the target RNA and/or have other effects on the target RNA, thereby contributing to the destabilization of the target RNA, preferably pre-mRNA, and/or to the decrease in amount of diseased or toxic transcript and/or protein in diseases like HD as identified later herein.

As herein defined, an oligonucleotide may comprise nucleotides with (RNaseH resistant) chemical substitutions at least one of its 5' or 3' ends, to provide intracellular stability, and comprises less than 9, more preferably less than 6 consecutive (RNaseH-sensitive) deoxyribose nucleotides in the rest of its sequence. The rest of the sequence is preferably the center of the sequence. Such oligonucleotide is called a gapmer. Gapmers have been extensively described in WO 2007/089611. Gapmers are designed to enable the recruitment and/or activation of RNaseH. Without wishing to be bound by theory, it is believed that RNaseH is recruited and/or activated via binding to the central region of the gapmer made of deoxyriboses. An oligonucleotide of the invention which is preferably substantially independent of or independent of RNaseH is designed in order to have a central region which is substantially not able or is not able to recruit and/or activate RNaseH. In a preferred embodiment, the rest of the sequence of said oligonucleotide, more preferably its central part comprises less than 9, 8, 7, 6, 5, 4, 3, 2, 1, or no deoxyribose. Accordingly, this oligonucleotide of the invention is preferably partly to fully replaced as earlier defined herein. "Partly replaced" means that the oligonucleotide comprises at least some of nucleotides that have been replaced, preferably at least 50% of its nucleotides have been replaced, or at least 55%, 60%, 65%, 70%, 75%, 80%, 85%, 90% or 95% have been replaced. 100% replacement of nucleotides corresponds to "fully replaced".

Accordingly, the invention provides an oligonucleotide comprising a 2'-O-methyl phosphorothioate RNA residue or consisting of 2'-O-methyl phosphorothioate RNA and comprising a 5-methylpyrimidine and/or a 2,6-diaminopurine base. Most preferably, this oligonucleotide consists of 2'-O-methyl RNA residues connected through a phosphorothioate backbone and all of its cytosines and/or all of its uracils and/or all of its adenines, independently, have been replaced by 5-methylcytosine, 5-methyluracil and/or 2,6-diaminopurine, respectively. Thus, an oligonucleotide of the invention may have:

At least one and preferably all cytosines replaced with 5-methylcytosines,

At least one and preferably all cytosines replaced with 5-methylcytosines and at least one and preferably all uracils replaced with 5-methyluracils, At least one and preferably all cytosines replaced with 5-methylcytosines and at least one and preferably all adenines replaced with 2,6-diaminopurines, At least one and preferably all cytosines replaced with 5-methylcytosines and at least one and preferably all uracils replaced with 5-methyluracils and at least one and preferably all adenines replaced with 2,6-diaminopurines, At least one and preferably all uracils replaced with 5-methyluracils, At least one and preferably all uracils replaced with 5-methyluracils and at least one and preferably all adenines replaced with 2,6-diaminopurines, or At least one and preferably all adenines replaced with 2,6-diaminopurines.

An oligonucleotide of the invention is for use as a medicament for preventing delaying and/or treating a human cis-element repeat instability associated genetic disorders preferably as exemplified herein. A human cis-element repeat instability associated genetic disorders as identified herein is preferably a neuromuscular disorder. Preferably said oligonucleotide is for use in therapeutic RNA modulation. Therefore, the oligonucleotide according to the invention may be described as an antisense oligonucleotide (AON). An antisense oligonucleotide is an oligonucleotide which binds (or is able to bind), targets, hybridizes to (or is able to hybridize to) and/or is reverse complementary to a specific sequence of a transcript of a gene which is known to be associated with or involved in a human cis-element repeat instability associated genetic neuromuscular disorder.

According to the invention, an antisense oligonucleotide comprising or consisting of 2'-O-methyl RNA nucleotide residues, having a backbone wherein at least one phosphate moiety is replaced by a phosphorothioate moiety, and further comprising at least one of a 5-methylcytosine and/or a 5-methyluracil and/or a 2,6-diaminopurine, is represented by a nucleotide sequence comprising or consisting of a sequence that binds (or is able to bind), hybridizes (or is able to hybridize), targets and/or is reverse complementary to a repetitive element in a RNA transcript having as repetitive nucleotide unit a repetitive nucleotide unit, which is selected from the $(CAG)_n$, $(GCG)_n$, $(CGG)_n$, $(GAA)_n$, $(GCC)_n$, $(CCG)_n$, $(AUUCU)_n$, $(GGGGCC)_n$ or $(CCUG)_n$. Said oligonucleotide is preferably a single stranded oligonucleotide.

Although it is to be understood that an oligonucleotide of the invention binds (or is able to bind), hybridizes (or is able to hybridize), targets and/or is reverse complementary to a repetitive element present in a RNA transcript as identified above, it can not be ruled out that such oligonucleotide may also interfere with or bind (or is able to bind) or hybridize to (or is able to hybridize) a corresponding DNA, this RNA transcript is derived from.

A repeat or repetitive element or repetitive sequence or repetitive stretch is herein defined as a repetition of at least 3, 4, 5, 10, 100, 1000 or more, of a repetitive unit or repetitive nucleotide unit or repeat nucleotide unit (as $(CAG)_n$, $(GCG)_n$, $(CGG)_n$, $(GAA)_n$, $(GCC)_n$, $(CCG)_n$, $(AUUCU)_n$, $(GGGGCC)_n$ or $(CCUG)_n$), comprising a trinucleotide repetitive unit, or alternatively a 4, 5 or 6 nucleotide repetitive unit, in a transcribed gene sequence in the genome of a subject, including a human subject. Accordingly, n is an integer and may be at least 3, 4, 5, 10, 100, 1000 or more. The invention is not limited to exemplified repetitive nucleotide units. Other repetitive nucleotide unit could be found on the following site http://neuromuscular.wustl.edu.mother/dnarep.htm. In the majority of patients, a "pure" repeat or repetitive element or repetitive sequence or repetitive stretch as identified above (as $(CAG)_n$, $(GCG)_n$, $(CGG)_n$, $(GAA)_n$, $(GCC)_n$, $(CCG)_n$, $(AUUCU)_n$, $(GGGGCC)_n$ or $(CCUG)_n$) is present in a transcribed gene sequence in the genome of said patient. However, it is also encompassed by the invention, that in some patients, said repeat or repetitive element or repetitive sequence or repetitive stretch as identified above is not qualified as "pure" or is qualified as a "variant" when for example said repeat or repetitive element or repetitive sequence or repetitive stretch as identified above is interspersed with at least 1, 2, or 3 nucleotide(s) that do not fit the nucleotide(s) of said repeat or repetitive element or repetitive sequence or repetitive stretch (Braida C., et al).

An oligonucleotide according to the invention therefore may not need to be 100% reverse complementary to a targeted repeat. Usually an oligonucleotide of the invention may be at least 90%, 95%, 97%, 99% or 100% reverse complementary to a targeted repeat.

In an embodiment, an antisense oligonucleotide comprises or consists of 2'-O-methyl phosphorothioate RNA, comprises a 5-methylcytosine and/or a 5-methyluracil and/or a 2,6-diaminopurine, is represented by a nucleotide sequence comprising or consisting of a sequence that binds (or is able to bind), hybridizes (or is able to hybridize), targets and/or is reverse complementary to a $(CAG)_n$ tract in a transcript and is particularly useful for the treatment, delay, amelioration and/or prevention of the human genetic diseases Huntington's disease (HD), spinocerebellar ataxia (SCA) type 1, 2, 3, 6, 7, 12 or 17, amyotrophic lateral sclerosis (ALS), frontotemporal dementia (FTD), X-linked spinal and bulbar muscular atrophy (SBMA) and/or dentatorubropallidoluysian atrophy (DRPLA) caused by CAG repeat expansions in the transcripts of the HTT (SEQ ID NO: 80), ATXN1 (SEQ ID NO:81), ATXN2 (SEQ ID NO: 82) ATXN3 (SEQ ID NO: 83), CACNA1A (SEQ ID NO:84), ATXN7 (SEQ ID NO: 85), PPP2R2B (SEQ ID NO: 86), TBP (SEQ ID NO: 87), AR (SEQ ID NO: 88) or ATN1 (SEQ ID NO: 89) genes. Preferably, these genes are from human origin. In this embodiment, an oligonucleotide comprises or consists of 2'-O-methyl phosphorothioate RNA, comprises a 5-methylcytosine and/or a 5-methyluracil and/or a 2,6-diaminopurine, is represented by a nucleotide sequence comprising or consisting of a sequence that binds (or is able to bind), hybridizes (or is able to hybridize), targets and/or is reverse complementary to a $(CAG)_n$ repeat as identified above and has as repetitive nucleotide unit $(CUG)_m$. The m in $(CUG)_m$ is preferably an integer which is 4, 5, 6, 7, 8, 9, 10, 11, 12. In a preferred embodiment, m is 5 or 6 or 7 or 8 or 9 or 10 or 11 or 12.

It is to be noted that for ALS and FTD, it is known that at least two distinct repeats in at least two distinct transcripts may be involved or may be responsible or linked with the disease. One has been identified in the previous paragraph (i.e. $(CAG)_n$ in a ATXN2 transcript). Another one is being identified later as a $(GGGGCC)_n$ repeat or tract in a C9ORF72 transcript. It means that for each of these two diseases, one may envisage to use either one of these two distinct oligonucleotides of the invention to specifically induce the specific degradation of the corresponding (toxic) expanded repeat transcripts.

Throughout the application, an oligonucleotide defined as being reverse complementary to, binding (being able to bind), hybridizing (being able to hybridize) or targeting a repeat as identified above and has or comprises a repetitive nucleotide unit may have any length comprised from 12 to 36 nucleotides. If we take the example of CUG as repetitive nucleotide unit comprised within said oligonucleotide, any oligonucleotide comprising UGC or GCU as repetitive nucleotide unit is also encompassed by the present invention. Depending on the length of said oligonucleotide (for example from 12 to 36 nucleotides), the given repetitive nucleotide unit may not be complete at the 5' and/or at the 3' side of said oligonucleotide. Each of said oligonucleotide is encompassed within the scope of said invention.

Alternatively, if we still take as an example the oligonucleotide having CUG as repetitive nucleotide unit, it may be represented by $H-(P)_p-(CUG)_m-(Q)_q-H$, wherein m is an integer as defined above. Each occurrence of P and Q is, individually, an abasic monomer as defined above or a nucleotide, such as A, C, G, U or an analogue or equivalent thereof and p and q are each individually an integer, preferably 0, 1, 2, 3, 4, 5, 6, 7, 8, 9, 10, 11, 12, 13, 14, 15, 16, 17, 18, 19, 20 or higher up to 100. Thus, p and q are each individually an integer from 0 to 100, preferably an integer from 0 to 20, more preferably an integer from 0 to 10, more preferably from 0 to 6, even more preferably from 0 to 3. Thus, when p is 0, P is absent and when q is 0, Q is absent. The skilled person will appreciate that an oligonucleotide will always start with and end with a hydrogen atom (H), regardless of the amount and nature of the nucleotides present in the oligonucleotide.

It will be appreciated that herein $(CUG)_m$ may be replaced by any repeating nucleotide unit within the context of the invention. Thus, a preferred oligonucleotide according to the invention may be represented by $H-(P)_p-(R)_r-(Q)_q-H$, wherein $(R)_r$ is a repeating nucleotide unit within the context of the invention and P, Q, p and q are as defined above.

In the context of the present invention, an "analogue" or an "equivalent" of a nucleotide is to be understood as a nucleotide which comprises at least one modification with respect to the nucleotides naturally occurring in RNA, such as A, C, G and U. Such a modification may be a internucleoside linkage modification and/or a sugar modification and/or a base modification, as explained and exemplified above. Again taking the oligonucleotide having CUG as repetitive nucleotide unit, it is to be understood that the repeating sequence may start with either a C, a U or a G. Thus, in a preferred embodiment, p is not 0, and $(P)_p$ is represented by $(P')_{p'}UG$ or $(P')_{p''}G$, wherein each occurrence of P' is, individually, an abasic site or a nucleotide, such as A, C, G, U or an analogue or equivalent thereof, and p' is p−2 and p'' is p−1. Such oligonucleotides may be represented as:

$H-(P')_{p'}UG-(CUG)_m-(Q)_q-H$ or $H-(P')_{p''}G-(CUG)_m-(Q)_q-H$.

In an equally preferred embodiment, q is not 0, and $(Q)_q$ is represented by $CU(Q')_{q'}$ or $C(Q')_{q''}$ and each occurrence of Q' is, individually, an abasic site or a nucleotide, such as A, C, G, U or an analogue or equivalent thereof, and q' is q−2 and q'' is q−1. Such oligonucleotides may be represented as:

$H-(P)_p-(CUG)_m-CU(Q')_{q'}-H$ or $H-(P)_p-(CUG)_m-C(Q')_{q''}-H$.

In another preferred embodiment, both p and q are not 0, and both $(P)_p$ and $(Q)_q$ are represented by $(P')_{p'}UG$ or $(P')_{p''}G$ and $CU(Q')_{q'}$ or $C(Q')_{q''}$ respectively, wherein P', Q', p', p'', q' and q'' are as defined above. Such oligonucleotides may be represented as:

$H-(P')_{p'}UG-(CUG)_m-CU(Q')_{q'}-H$, $H-(P')_{p''}G-(CUG)_m-CU(Q')_{q'}-H$, $H-(P')_{p'}UG-(CUG)_m-C(Q')_{q''}-H$, or $H-(P')_{p''}G-(CUG)_m-C(Q')_{q''}-H$.

It is to be understood that p', p'', q' and q'' may not be negative integers. Thus, when $(P)_p$ is represented by $(P')_{p'}UG$ or $(P')_{p''}G$, p is at least 1 or at least 2 respectively, and when $(Q)_q$ is represented by $CU(Q')_{q'}$ or $C(Q')_{q''}$, q is at least 1 or at least 2 respectively.

It is to be understood that all said here regarding the CUG repeat unit can be extended to any repeat unit within the context of the invention.

In a preferred embodiment, an oligonucleotide defined as being reverse complementary to, binding (or being able to bind), hybridizing (or being able to hybridize) or targeting a $(CAG)_n$ repeat comprises or consists of a repetitive nucleotide unit $(XYG)_m$ and has a length comprised from 12 to 36 nucleotides and wherein each X is C or 5-methylcytosine, and each Y is U or 5-methyluracil such that at least one X is 5-methylcytosine and/or at least one Y is 5-methyluracil. m is an integer. In the context of this embodiment, m may be 4, 5, 6, 7, 8, 9, 10, 11, 12. A preferred value for m is 7.

A more preferred oligonucleotide therefore comprises or consists of a repetitive nucleotide unit $(XYG)_m$, wherein each X is C or 5-methylcytosine, and each Y is U or 5-methyluracil such that at least one X is 5-methylcytosine and/or at least one Y is 5-methyluracil, and m is an integer from 4 to 12 (SEQ ID NO:2 to 12).

An even more preferred oligonucleotide comprises or consists of a repetitive nucleotide unit $(XYG)_m$, wherein each X is 5-methylcytosine, and/or each Y is 5-methyluracil, and m is an integer from 4 to 12 (SEQ ID NO:2 to 12).

An even more preferred oligonucleotide therefore comprises or consists of a repetitive nucleotide unit $(XYG)_5$, $(XYG)_6$ or $(XYG)_7$, $(XYG)_8$, or $(XYG)_9$ wherein each X is C or 5-methylcytosine, and each Y is U or 5-methyluracil such that at least one X is 5-methylcytosine and/or at least one Y is 5-methyluracil. More preferred is an oligonucleotide comprising or consisting of $(XYG)_7$, wherein each X is C or 5-methylcytosine, and each Y is U or 5-methyluracil such that at least one X is 5-methylcytosine and/or at least one Y is 5-methyluracil (SEQ ID NO:7).

An even more preferred oligonucleotide comprises or consists of a repetitive nucleotide unit $(XYG)_7$, wherein each X is 5-methylcytosine and each Y is a uracil (SEQ ID NO: 2), or each X is a cytosine and each Y is 5-methyluracil (SEQ ID NO:3). An even more preferred oligonucleotide comprises SEQ ID NO:2 or 3 and has a length of 21, 22, 23, 24, 25, 26, 27, 28, 29, 30 nucleotides.

Most preferred oligonucleotides sequences comprising or consisting of a repetitive nucleotide unit $(XYG)_m$ have been identified in table 2 as SEQ ID NO:90-118.

A preferred oligonucleotide comprising or consisting of 2'-O-methyl phosphorothioate RNA comprises one of base sequences SEQ ID NO: 90-106 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 90-106 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 90-106 and has a length of 21 nucleotides.

A preferred oligonucleotide comprising or consisting of 2'-O-methyl phosphorothioate RNA comprises one of base sequences SEQ ID NO: 107 or 108 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 107 or 108 and has a length from 21-36 nucleotides, more preferably 21, 22, 23, 24, 25, 26, 27, 28, 29, 30, 31, 32, 33, 34, 35 or 36 nucleotides. Even more preferred oligonucleotide consists of 2'-O-methyl phosphorothioate RNA, has a base sequence that consists of one of the base sequences SEQ ID NO: 107 or 108 and has a length of 21 nucleotides.

Most preferred oligonucleotide consists of 2'-O-methyl phosphorothioate RNA, has a base sequence that consists of one of the base sequences SEQ ID NO: 107 or 108, has a length of 21 nucleotides and additionally comprises 4 abasic monomers at one of its termini, preferably at the 3' terminus. Said most preferred oligonucleotide is represented by a base sequence consisting of SEQ ID NO: 220 or 221.

A preferred oligonucleotide comprising or consisting of 2'-O-methyl phosphorothioate RNA comprises one of base sequences SEQ ID NO: 109 or 110 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 109 or 110 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 109 or 110 and has a length of 24 nucleotides. A preferred oligonucleotide comprising or consisting of 2'-O-methyl phosphorothioate RNA comprises one of base sequences SEQ ID NO: 111 or 112 and has a length from 27-36 nucleotides, more preferably 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 111 or 112 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 111 or 112 and has a length of 27 nucleotides.

A preferred oligonucleotide comprising or consisting of 2'-O-methyl phosphorothioate RNA comprises one of base sequences SEQ ID NO: 113 or 114 and has a length from 30-36 nucleotides, more preferably 30, 31, 32, 33, 34, 35 or 36 nucleotides. An even more preferred oligonucleotide consists of 2'-O-methyl phosphorothioate RNA and comprises one of the base sequences SEQ ID NO: 113 or 114 and has a length from 30-36 nucleotides, more preferably 30, 31, 32, 33, 34, 35 or nucleotides. Most preferred oligonucleotide consists of 2'-O-methyl phosphorothioate RNA, has a base sequence that consists of one of the base sequences SEQ ID NO: 113 or 114 and has a length of 30 nucleotides.

A preferred oligonucleotide comprising or consisting of 2'-O-methyl phosphorothioate RNA comprises one of base sequences SEQ ID NO: 115 or 116 and has a length from 33-36 nucleotides, more preferably 33, 34, 35 or 36 nucleotides. An even more preferred oligonucleotide consists of 2'-O-methyl phosphorothioate RNA and comprises one of the base sequences SEQ ID NO: 115 or 116 and has a length from 33-36 nucleotides, more preferably 33, 34, 35 or 36 nucleotides. Most preferred oligonucleotide consists of 2'-O-methyl phosphorothioate RNA, has a base sequence that consists of one of the base sequences SEQ ID NO: 115 or 116 and has a length of 33 nucleotides.

A preferred oligonucleotide comprising or consisting of 2'-O-methyl phosphorothioate RNA comprises one of base sequences SEQ ID NO: 117 or 118 and has a length of 36 nucleotides. Most preferred oligonucleotide consists of 2'-O-methyl phosphorothioate RNA, has a base sequence that consists of one of the base sequences SEQ ID NO: 117 or 118 and has a length of 36 nucleotides.

In another embodiment, an antisense oligonucleotide comprising or consisting of 2'-O-methyl phosphorothioate RNA, and comprising a 5-methylcytosine is represented by a nucleotide sequence comprising or consisting of a sequence that binds to (or is able to bind to), hybridizes (or is able to hybridize), targets and/or is reverse complementary to a $(GCG)_n$ repeat in a transcript and is particularly useful for the treatment, delay, amelioration and/or prevention of the human genetic diseases: infantile spasm syndrome, deidocranial dysplasia, blepharophimosis, hand-foot-genital disease, synpolydactyly, oculopharyngeal muscular dystrophy and/or holoprosencephaly, which are caused by repeat expansions in the ARX, CBFA1, FOXL2, HOXA13, HOXD13, OPDM/PABP2, TCFBR1 or ZIC2 genes. Preferably, these genes are from human origin.

In a preferred embodiment, an oligonucleotide defined as being reverse complementary to, binding (or being able to bind), hybridizing (or being able to hybridize) or targeting a $(GCG)_n$ repeat comprises or consists of a repetitive nucleotide unit $(XGX)_m$ and has a length comprised from 12 to 36 nucleotides and wherein each X is C or 5-methylcytosine, such that at least one X is 5-methylcytosine. m is an integer. In the context of this embodiment, m may be 4, 5, 6, 7, 8, 9, 10, 11, 12. A preferred value for m is 7.

A more preferred oligonucleotide therefore comprises or consists of a repetitive nucleotide unit $(XGX)_m$, wherein at least one X is 5-methylcytosine, and m is an integer from 4 to 12 (SEQ ID NO: 13 to 21). An even more preferred oligonucleotide comprises or consists of a repetitive nucleotide unit $(XGX)_m$, wherein each X is 5-methylcytosine, and m is an integer from 4 to 12 (SEQ ID NO: 13 to 21).

An even more preferred oligonucleotide therefore comprises or consists of a repetitive nucleotide unit $(XGX)_7$ (SEQ ID NO: 16), wherein at least one X is 5-methylcytosine.

An even more preferred oligonucleotide comprises or consists of a repetitive nucleotide unit $(XGX)_7$ (SEQ ID NO: 16), wherein each X is 5-methylcytosine.

Most preferred oligonucleotides sequences comprising or consisting of a repetitive nucleotide unit $(XGX)_m$ have been identified in table 2 as SEQ ID NO:119-132.

A preferred oligonucleotide comprising or consisting of 2'-O-methyl phosphorothioate RNA comprises one of base sequences SEQ ID NO: 119 or 120 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 119 or 120 and has a length from 16-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 119 or 120 and has a length of 12 nucleotides.

A preferred oligonucleotide comprising or consisting of 2'-O-methyl phosphorothioate RNA comprises one of base sequences SEQ ID NO: 121 or 122 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 90-106 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 121 or 122 and has a length of 15 nucleotides.

A preferred oligonucleotide comprising or consisting of 2'-O-methyl phosphorothioate RNA comprises one of base sequences SEQ ID NO: 123 or 124 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 123 or 124 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 123 or 124 and has a length of 18 nucleotides.

A preferred oligonucleotide comprising or consisting of 2'-O-methyl phosphorothioate RNA comprises one of base sequences SEQ ID NO: 125 or 126 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 125 or 126 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 125 or 126 and has a length of 21 nucleotides.

A preferred oligonucleotide comprising or consisting of 2'-O-methyl phosphorothioate RNA comprises one of base sequences SEQ ID NO: 127 or 128 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 127 or 128 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 127 or 128 and has a length of 24 nucleotides. A preferred oligonucleotide comprising or consisting of 2'-O-methyl phosphorothioate RNA comprises one of base sequences SEQ ID NO: 129 or 130 and has a length from 27-36 nucleotides, more preferably 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 129 or 130 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 129 or 130 and has a length of 27 nucleotides.

A preferred oligonucleotide comprising or consisting of 2'-O-methyl phosphorothioate RNA comprises one of base sequences SEQ ID NO: 131 or 132 and has a length from 30-36 nucleotides, more preferably 30, 31, 32, 33, 34, 35 or 36 nucleotides. An even more preferred oligonucleotide consists of 2'-O-methyl phosphorothioate RNA and comprises one of the base sequences SEQ ID NO: 131 or 132 and has a length from 30-36 nucleotides, more preferably 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 131 or 132 and has a length of 30 nucleotides.

In another embodiment, an oligonucleotide comprising or consisting of 2'-O-methyl phosphorothioate RNA and comprising a 5-methylcytosine, is represented by a nucleotide sequence comprising or consisting of a sequence that binds (or is able to bind), targets, hybridizes (or is able to hybridize) and/or is reverse complementary to a $(CGG)_n$ repeat in a transcript and is particularly useful for the treatment, delay, amelioration and/or prevention of human fragile X syndromes, caused by repeat expansion in the FMR1 gene. Preferably, these genes are from human origin.

In a preferred embodiment, an oligonucleotide defined as being reverse complementary to, binding (or is able to bind), hybridizing (or is able to hybridize) or targeting a $(CGG)_n$ repeat comprises or consists of a repetitive nucleotide unit $(XXG)_m$ and has a length comprised from 12 to 36 nucleotides and wherein each X is C or 5-methylcytosine, such that at least one X is 5-methylcytosine.

m is an integer. In the context of this embodiment, m may be 4, 5, 6, 7, 8, 9, 10, 11, 12. A preferred value for m is 7.

A more preferred oligonucleotide therefore comprises or consists of a repetitive nucleotide unit (XXG), wherein each X is C or 5-methylcytosine, such that at least one X is 5-methylcytosine, and m is an integer from 4 to 12 (SEQ ID NO: 22 to 30).

An even more preferred oligonucleotide comprises or consists of a repetitive nucleotide unit $(XXG)_m$, wherein each X is 5-methylcytosine, and m is an integer from 4 to 12 (SEQ ID NO: 22 to 30).

An even more preferred oligonucleotide therefore comprises or consists of a repetitive nucleotide unit $(XXG)_7$ (SEQ ID NO: 25), wherein each X is C or 5-methylcytosine, such that at least one X is 5-methylcytosine.

An even more preferred oligonucleotide comprises or consists of a repetitive nucleotide unit $(XXG)_7$ (SEQ ID NO: 25), wherein each X is 5-methylcytosine.

Most preferred oligonucleotides sequences comprising or consisting of a repetitive nucleotide unit $(XXG)_m$ have been identified in table 2 as SEQ ID NO: 133-146.

A preferred oligonucleotide comprising or consisting of 2'-O-methyl phosphorothioate RNA comprises one of base sequences SEQ ID NO: 133 or 134 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 133 or 134 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 133 or 134 and has a length of 12 nucleotides.

A preferred oligonucleotide comprising or consisting of 2'-O-methyl phosphorothioate RNA comprises one of base sequences SEQ ID NO: 135 or 136 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 135 or 136 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 135 or 136 and has a length of 15 nucleotides. A preferred oligonucleotide comprising or consisting of 2'-O-methyl phosphorothioate RNA comprises one of base sequences SEQ ID NO: 137 or 138 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 137 or 138 and has a length from 18-36 nucleotides, more preferably 18, 19, 20, 21, 22, 23, 24, 25, 26, 27, 28, 29, 30, 31, 32, 33, 34, 35 or nucleotides. Most preferred oligonucleotide consists of 2'-O-methyl phosphorothioate RNA, has a base sequence that consists of one of the base sequences SEQ ID NO: 137 or 138 and has a length of 18 nucleotides.

A preferred oligonucleotide comprising or consisting of 2'-O-methyl phosphorothioate RNA comprises one of base sequences SEQ ID NO: 139 or 140 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 139 or 140 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 139 or 140 and has a length of 21 nucleotides.

A preferred oligonucleotide comprising or consisting of 2'-O-methyl phosphorothioate RNA comprises one of base sequences SEQ ID NO: 141 or 142 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 141 or 142 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 141 or 142 and has a length of 24 nucleotides. A preferred oligonucleotide comprising or consisting of 2'-O-methyl phosphorothioate RNA comprises one of base sequences SEQ ID NO: 143 or 144 and has a length from 27-36 nucleotides, more preferably 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 143 or 144 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 143 or 144 and has a length of 27 nucleotides.

A preferred oligonucleotide comprising or consisting of 2'-O-methyl phosphorothioate RNA comprises one of base sequences SEQ ID NO: 145 or 146 and has a length from 30-36 nucleotides, more preferably 30, 31, 32, 33, 34, 35 or 36 nucleotides. An even more preferred oligonucleotide consists of 2'-O-methyl phosphorothioate RNA and comprises one of the base sequences SEQ ID NO: 145 or 146 and has a length from 30-36 nucleotides, more preferably 30, 31, 32, 33, 34, 35 or nucleotides. Most preferred oligonucleotide consists of 2'-O-methyl phosphorothioate RNA, has a base sequence that consists of one of the base sequences SEQ ID NO: 145 or 146 and has a length of 30 nucleotides.

In another embodiment, an oligonucleotide comprising or consisting of 2'-O-methyl phosphorothioate RNA and comprising a 5-methylcytosine and/or a 5-methyluracil, is represented by a nucleotide sequence comprising or consisting of a sequence that binds (or is able to bind), targets, hybridizes (or is able to hybridize) and/or is reverse complementary to a $(GAA)_n$ repeat in a transcript and is particularly useful for the treatment, delay and/or prevention of the human genetic disorder Friedreich's ataxia.

In a preferred embodiment, an oligonucleotide defined as being reverse complementary to, binding (or being able to bind), hybridizing (or being able to hybridize) or targeting a $(GAA)_n$ repeat comprises or consists of a repetitive nucleotide unit $(YYX)_m$ and has a length comprised from 12 to 36 nucleotides and wherein each X is C or 5-methylcytosine, and each Y is U or 5-methyluracil such that at least one X is 5-methylcytosine and/or at least one Y is 5-methyluracil.

m is an integer. In the context of this embodiment, m may be 4, 5, 6, 7, 8, 9, 10, 11, 12. A preferred value for m is 7.

A more preferred oligonucleotide therefore comprises or consists of a repetitive nucleotide unit $(YYX)_m$, wherein each X is C or 5-methylcytosine, and each Y is U or 5-methyluracil such that at least one X is 5-methylcytosine and/or at least one Y is 5-methyluracil, and m is an integer from 4 to 12 (SEQ ID NO: 31 to 39).

An even more preferred oligonucleotide comprises or consists of a repetitive nucleotide unit $(YYX)_m$, wherein each X is 5-methylcytosine, and/or each Y is 5-methyluracil, and m is an integer from 4 to 12 (SEQ ID NO: 31 to 39).

An even more preferred oligonucleotide therefore comprises or consists of a repetitive nucleotide unit $(YYX)_7$ (SEQ ID NO: 34), wherein each X is C or 5-methylcytosine, and each Y is U or 5-methyluracil such that at least one X is 5-methylcytosine and/or at least one Y is 5-methyluracil.

An even more preferred oligonucleotide comprises or consists of a repetitive nucleotide unit $(YYX)_7$ (SEQ ID NO: 34), wherein each X is 5-methylcytosine, and/or each Y is 5-methyluracil.

Most preferred oligonucleotides sequences comprising or consisting of a repetitive nucleotide unit $(XYG)_m$ have been identified in table 2 as SEQ ID NO: 147-167.

A preferred oligonucleotide comprising or consisting of 2'-O-methyl phosphorothioate RNA comprises one of base sequences SEQ ID NO: 147 or 148 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 147 or 148 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 147 or 148 and has a length of 12 nucleotides.

A preferred oligonucleotide comprising or consisting of 2'-O-methyl phosphorothioate RNA comprises one of base sequences SEQ ID NO: 149 or 150 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 149 or 150 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 149 or 150 and has a length of 15 nucleotides.

A preferred oligonucleotide comprising or consisting of 2'-O-methyl phosphorothioate RNA comprises one of base sequences SEQ ID NO: 151 or 152 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 151 or 152 and has a length from 18-36 nucleotides, more preferably 18, 19, 20, 21, 22, 23, 24, 25, 26, 27, 28, 29, 30, 31, 32, 33, 34, 35 or nucleotides. Most preferred oligonucleotide consists of 2'-O-methyl phosphorothioate RNA, has a base sequence that consists of one of the base sequences SEQ ID NO: 151 or 152 and has a length of 18 nucleotides.

A preferred oligonucleotide comprising or consisting of 2'-O-methyl phosphorothioate RNA comprises one of base sequences SEQ ID NO: 153-157 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 153-157 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 153-157 and has a length of 21 nucleotides.

A preferred oligonucleotide comprising or consisting of 2'-O-methyl phosphorothioate RNA comprises one of base sequences SEQ ID NO: 158 or 159 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 158 or 159 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 158 or 159 and has a length of 24 nucleotides.

A preferred oligonucleotide comprising or consisting of 2'-O-methyl phosphorothioate RNA comprises one of base sequences SEQ ID NO: 160 or 161 and has a length from 27-36 nucleotides, more preferably 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 160 or 161 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 160 or 161 and has a length of 27 nucleotides.

A preferred oligonucleotide comprising or consisting of 2'-O-methyl phosphorothioate RNA comprises one of base sequences SEQ ID NO: 162 or 163 and has a length from 30-36 nucleotides, more preferably 30, 31, 32, 33, 34, 35 or 36 nucleotides. An even more preferred oligonucleotide consists of 2'-O-methyl phosphorothioate RNA and comprises one of the base sequences SEQ ID NO: 162 or 163 and has a length from 30-36 nucleotides, more preferably 30, 31, 32, 33, 34, 35 or nucleotides. Most preferred oligonucleotide consists of 2'-O-methyl phosphorothioate RNA, has a base sequence that consists of one of the base sequences SEQ ID NO: 162 or 163 and has a length of 30 nucleotides.

A preferred oligonucleotide comprising or consisting of 2'-O-methyl phosphorothioate RNA comprises one of base sequences SEQ ID NO: 164 or 165 and has a length from 33-36 nucleotides, more preferably 33, 34, 35 or 36 nucleotides. An even more preferred oligonucleotide consists of 2'-O-methyl phosphorothioate RNA and comprises one of the base sequences SEQ ID NO: 164 or 165 and has a length from 33-36 nucleotides, more preferably 33, 34, 35 or 36 nucleotides. Most preferred oligonucleotide consists of 2'-O-methyl phosphorothioate RNA, has a base sequence that consists of one of the base sequences SEQ ID NO: 164 or 165 and has a length of 33 nucleotides.

A preferred oligonucleotide comprising or consisting of 2'-O-methyl phosphorothioate RNA comprises one of base sequences SEQ ID NO: 166 or 167 and has a length of 36 nucleotides. An even more preferred oligonucleotide consists of 2'-O-methyl phosphorothioate RNA and has a base sequence that consists one of the base sequences SEQ ID NO: 166 or 167 and has a length of 36 nucleotides.

In another embodiment, an antisense oligonucleotide comprising or consisting of 2'-O-methyl phosphorothioate RNA and comprising a 5-methylcytosine, is represented by a nucleotide sequence comprising or consisting of a sequence that binds to (or is able to bind), hybridizes (or is able to hybridize), targets and/or is reverse complementary to a $(CCG)_n$ or $(GCC)_n$ repeat in a transcript and is particularly useful for the treatment, delay, amelioration and/or prevention of the human genetic disorder fragile XE mental retardation, caused by repeat expansion in the FMR2 gene. Preferably, these genes are from human origin.

In a preferred embodiment, an oligonucleotide defined as being reverse complementary to, binding (or being able to bind), hybridizing (or being able to hybridize) or targeting a $(CCG)_n$ repeat comprises or consists of a repetitive nucleotide unit $(XGG)_m$ or $(GGX)_m$ and has a length comprised from 12 to 36 nucleotides and wherein each X is C or 5-methylcytosine. m is an integer. In the context of this embodiment, m may be 4, 5, 6, 7, 8, 9, 10, 11, 12. A preferred value for m is 7.

A more preferred oligonucleotide therefore comprises or consists of a repetitive nucleotide unit $(XGG)_m$ or $(GGX)_m$, wherein each X is C or 5-methylcytosine, and m is an integer from 4 to 12 (SEQ ID NO: 49 to 57) or (SEQ ID NO: 40 to 48).

An even more preferred oligonucleotide comprises or consists of a repetitive nucleotide unit $(XGG)_m$ or $(GGX)_m$, wherein each X is 5-methylcytosine, and m is an integer from 4 to 12 (SEQ ID NO: 49 to 57) or (SEQ ID NO: 40 to 48).

An even more preferred oligonucleotide therefore comprises or consists of a repetitive nucleotide unit $(XGG)_7$ (SEQ ID NO: 52) or $(GGX)_7$ (SEQ ID NO: 43), wherein each X is C or 5-methylcytosine.

An even more preferred oligonucleotide comprises or consists of a repetitive nucleotide unit $(XGG)_7$ (SEQ ID NO: 52) or $(GGX)_7$ (SEQ ID NO: 43), wherein each X is 5-methylcytosine.

Most preferred oligonucleotides sequences comprising or consisting of a repetitive nucleotide unit $(GGX)_m$ have been identified in table 2 as SEQ ID NO: 168-177.

A preferred oligonucleotide comprising or consisting of 2'-O-methyl phosphorothioate RNA comprises base sequence SEQ ID NO: 168 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequences SEQ ID NO: 168 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequences SEQ ID NO: 168 and has a length of 12 nucleotides.

A preferred oligonucleotide comprising or consisting of 2'-O-methyl phosphorothioate RNA comprises base sequence SEQ ID NO: 169 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 169 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 169 and has a length of 15 nucleotides.

A preferred oligonucleotide comprising or consisting of 2'-O-methyl phosphorothioate RNA comprises base sequence SEQ ID NO: 170 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 170 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 170 and has a length of 18 nucleotides.

A preferred oligonucleotide comprising or consisting of 2'-O-methyl phosphorothioate RNA comprises one of base sequences SEQ ID NO: 171-174 has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 171-174 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 171-174 and has a length of 21 nucleotides.

A preferred oligonucleotide comprising or consisting of 2'-O-methyl phosphorothioate RNA comprises base sequence SEQ ID NO: 175 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 175 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 175 and has a length of 24 nucleotides.

A preferred oligonucleotide comprising or consisting of 2'-O-methyl phosphorothioate RNA comprises base sequence SEQ ID NO: 176 and has a length from 27-36 nucleotides, more preferably 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 176 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 176 and has a length of 27 nucleotides.

A preferred oligonucleotide comprising or consisting of 2'-O-methyl phosphorothioate RNA comprises base sequence SEQ ID NO: 177 and has a length from 30-36 nucleotides, more preferably 30, 31, 32, 33, 34, 35 or 36 nucleotides. An even more preferred oligonucleotide consists of 2'-O-methyl phosphorothioate RNA and comprises base sequence SEQ ID NO: 177 and has a length from 30-36 nucleotides, more preferably 30, 31, 32, 33, 34, 35 or 36 nucleotides. Most preferred oligonucleotide consists of 2'-O-methyl phosphorothioate RNA, has its base sequence that consists of base sequence SEQ ID NO: 177 and has a length of 30 nucleotides.

Most preferred oligonucleotides sequences comprising or consisting of a repetitive nucleotide unit $(XGG)_m$ have been identified in table 2 as SEQ ID NO: 178-184.

A preferred oligonucleotide comprising or consisting of 2'-O-methyl phosphorothioate RNA comprises base sequence SEQ ID NO: 178 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 178 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 178 and has a length of 12 nucleotides.

A preferred oligonucleotide comprising or consisting of 2'-O-methyl phosphorothioate RNA comprises base sequence SEQ ID NO: 179 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 179 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 179 and has a length of 15 nucleotides.

A preferred oligonucleotide comprising or consisting of 2'-O-methyl phosphorothioate RNA comprises base sequences SEQ ID NO: 180 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 180 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 180 and has a length of 18 nucleotides.

A preferred oligonucleotide comprising or consisting of 2'-O-methyl phosphorothioate RNA comprises base sequence SEQ ID NO: 181 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 181 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 181 and has a length of 21 nucleotides.

A preferred oligonucleotide comprising or consisting of 2'-O-methyl phosphorothioate RNA comprises base sequence SEQ ID NO: 182 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 182 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 182 and has a length of 24 nucleotides.

A preferred oligonucleotide comprising or consisting of 2'-O-methyl phosphorothioate RNA comprises base sequence SEQ ID NO: 183 and has a length from 27-36 nucleotides, more preferably 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 183 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 183 and has a length of 27 nucleotides.

A preferred oligonucleotide comprising or consisting of 2'-O-methyl phosphorothioate RNA comprises base sequence SEQ ID NO: 184 and has a length from 30-36 nucleotides, more preferably 30, 31, 32, 33, 34, 35 or 36 nucleotides. An even more preferred oligonucleotide consists of 2'-O-methyl phosphorothioate RNA and comprises base sequence SEQ ID NO: 184 and has a length from 30-36 nucleotides, more preferably 30, 31, 32, 33, 34, 35 or 36 nucleotides. Most preferred oligonucleotide consists of 2'-O-methyl phosphorothioate RNA, has its base sequence that consists of base sequence SEQ ID NO: 184 and has a length of 30 nucleotides.

In another embodiment, an oligonucleotide comprising or consisting of 2'-O-methyl phosphorothioate RNA and comprising a 5-methylcytosine and/or a 2,6-diaminopurine, is represented by a nucleotide sequence comprising or consisting of a sequence that binds (or is able to bind), hybridizes (or is able to hybridize), targets and/or is reverse complementary to a $(CCUG)_n$ repeat in a transcript and is particularly useful for the treatment, delay and/or prevention of the human genetic disorder myotonic dystrophy type 2 (DM2), caused by repeat expansions in the DM2/ZNF9 gene. Preferably, these genes are from human origin.

In a preferred embodiment, an oligonucleotide defined as being reverse complementary to, binding (or being able to bind), hybridizing (or being able to hybridize) or targeting a $(CCUG)_n$ repeat comprises or consists of a repetitive nucleotide unit $(XZGG)_m$ and has a length comprised from 12 to 36 nucleotides and wherein each X is C or 5-methylcytosine, and each Z is A or 2,6-diaminopurine such that at least one X is 5-methylcytosine and/or at least one Z is 2,6-diaminopurine.

m is an integer. In the context of this embodiment, m may be 3, 4, 5, 6, 7, 8, 9. A preferred value for m is 5.

A more preferred oligonucleotide therefore comprises or consists of a repetitive nucleotide unit $(XZGG)_m$, wherein each X is C or 5-methylcytosine, and each Z is A or 2,6-diaminopurine such that at least one X is 5methylcytosine and/or at least one A is 2,6-diaminopurine, and m is an integer from 3 to 9 (SEQ ID NO: 63 to 69).

An even more preferred oligonucleotide comprises or consists of a repetitive nucleotide unit $(XZGG)_m$, wherein each X is 5-methylcytosine, and/or each Z is 2,6-diaminopurine, and m is an integer from 3 to 9 (SEQ ID NO: 63 to 69).

An even more preferred oligonucleotide therefore comprises or consists of a repetitive nucleotide unit $(XZGG)_5$ (SEQ ID NO: 65), wherein each X is C or 5-methylcytosine, and each Z is A or 2,6-diaminopurine such that at least one X is 5-methylcytosine and/or at least one Z is 2,6-diaminopurine.

An even more preferred oligonucleotide comprises or consists of a repetitive nucleotide unit $(XZGG)_5$ (SEQ ID NO: 65), wherein each X is 5-methyl-cytosine, and/or each Z is 2,6-diaminopurine.

Most preferred oligonucleotides sequences comprising or consisting of a repetitive nucleotide unit $(XZGG)_m$ have been identified in table 2 as SEQ ID NO: 193-208.

A preferred oligonucleotide comprising or consisting of 2'-O-methyl phosphorothioate RNA comprises one of base sequences SEQ ID NO: 193 or 194 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 193 or 194 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 193 or 194 and has a length of 12 nucleotides.

A preferred oligonucleotide comprising or consisting of 2'-O-methyl phosphorothioate RNA comprises one of base sequences SEQ ID NO: 195 or 196 and has a length from 16-36 nucleotides, more preferably 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 195 or 196 and has a length from 16-36 nucleotides, more preferably 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 195 or 196 and has a length of 16 nucleotides.

A preferred oligonucleotide comprising or consisting of 2'-O-methyl phosphorothioate RNA comprises one of base sequences SEQ ID NO: 197-200 and has a length from 20-36 nucleotides, more preferably 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 197-200 and has a length from 20-36 nucleotides, more preferably 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 197-200 and has a length of 20 nucleotides.

A preferred oligonucleotide comprising or consisting of 2'-O-methyl phosphorothioate RNA comprises one of base sequences SEQ ID NO: 201 or 202 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 201 or 202 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 201 or 202 and has a length of 24 nucleotides. A preferred oligonucleotide comprising or consisting of 2'-O-methyl phosphorothioate RNA comprises one of base sequences SEQ ID NO: 203 or 204 and has a length from 28-36 nucleotides, more preferably 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 203 or 204 and has a length from 28-36 nucleotides, more preferably 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 203 or 204 and has a length of 28 nucleotides.

A preferred oligonucleotide comprising or consisting of 2'-O-methyl phosphorothioate RNA comprises one of base sequences SEQ ID NO: 205 or 206 and has a length from 32-36 nucleotides, more preferably 32, 33, 34, 35 or 36 nucleotides. An even more preferred oligonucleotide consists of 2'-O-methyl phosphorothioate RNA and comprises one of the base sequences SEQ ID NO: 205 or 206 and has a length from 32-36 nucleotides, more preferably 32, 33, 34, 35 or 36 nucleotides. Most preferred oligonucleotide consists of 2'-O-methyl phosphorothioate RNA, has its base sequence that consists of one of the base sequences SEQ ID NO: 205 or 206 and has a length of 32 nucleotides.

A preferred oligonucleotide comprising or consisting of 2'-O-methyl phosphorothioate RNA comprises one of base sequences SEQ ID NO: 207 or 208 and has a length of 36 nucleotides. An even more preferred oligonucleotide consists of 2'-O-methyl phosphorothioate RNA and has its base sequence that consists of one of the base sequences SEQ ID NO: 207 or 208 and has a length of 36 nucleotides.

In another embodiment, an oligonucleotide comprising or consisting of 2'-O-methyl phosphorothioate RNA and comprising a 5-methyluracil and/or a 2,6-diaminopurine, is represented by a nucleotide sequence comprising or consisting of a sequence that binds (or is able to bind), hybridizes (or is able to hybridize), targets and/or is reverse complementary to a $(AUUCU)_n$ repeat in an intron and is particularly useful for the treatment, delay, amelioration and/or prevention of the human genetic disorder spinocerebellar ataxia type 10 (SCA10). Preferably, this gene is from human origin.

In a preferred embodiment, an oligonucleotide defined as being reverse complementary to, binding (or being able to bind), hybridizing (or being able to hybridize) or targeting a $(AUUCU)_n$ repeat comprises or consists of a repetitive nucleotide unit $(ZGZZY)_m$ and has a length comprised from 12 to 36 nucleotides and wherein each Y is U or 5-methyluracil, and each Z is A or 2,6-diaminopurine such that at least one Y is 5-methyluracil and/or at least one Z is 2,6-diaminopurine. m is an integer. In the context of this embodiment, m may be 3, 4, 5, 6, 7. A preferred value for m is 4.

A more preferred oligonucleotide therefore comprises or consists of a repetitive nucleotide unit $(ZGZZY)_m$, wherein each Y is U or 5-methyluracil, and each Z is A or 2,6-diaminopurine such that at least one Y is 5-methyluracil and/or at least one Z is 2,6-diaminopurine, and m is an integer from 3 to 7 (SEQ ID NO: 58 to 62).

An even more preferred oligonucleotide comprises or consists of a repetitive nucleotide unit $(ZGZZY)_m$, wherein each Y is 5-methyluracil, and/or each Z is 2,6-diaminopurine, and m is an integer from 3 to 7 (SEQ ID NO: 58 to 62).

An even more preferred oligonucleotide therefore comprises or consists of a repetitive nucleotide unit $(ZGZZY)_4$ (SEQ ID NO: 59), wherein each Y is C or 5-methyluracil, and each Z is A or 2,6-diaminopurine such that at least one Y is 5-methyluracil and/or at least one Z is 2,6-diaminopurine.

An even more preferred oligonucleotide comprises or consists of a repetitive nucleotide unit $(ZGZZY)_4$ (SEQ ID NO: 59), wherein each Y is 5-methyluracil, and/or each Z is 2,6-diaminopurine.

Most preferred oligonucleotides sequences comprising or consisting of a repetitive nucleotide unit $(ZGZZY)_m$ have been identified in table 2 as SEQ ID NO:185-192.

A preferred oligonucleotide comprising or consisting of 2'-O-methyl phosphorothioate RNA comprises base sequence SEQ ID NO: 185 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 185 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 185 and has a length of 15 nucleotides.

A preferred oligonucleotide comprising or consisting of 2'-O-methyl phosphorothioate RNA comprises one of base sequences SEQ ID NO: 186-189 and has a length from 20-36 nucleotides, more preferably 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 186-189 and has a length from 20-36 nucleotides, more preferably 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 186-189 and has a length of 20 nucleotides.

A preferred oligonucleotide comprising or consisting of 2'-O-methyl phosphorothioate RNA comprises base sequence SEQ ID NO: 190 and has a length from 25-36 nucleotides, more preferably 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 190 and has a length from 25-36 nucleotides, more preferably 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 190 and has a length of 25 nucleotides.

A preferred oligonucleotide comprising or consisting of 2'-O-methyl phosphorothioate RNA comprises base sequence SEQ ID NO: 191 and has a length from 30-36 nucleotides, more preferably 30, 31, 32, 33, 34, 35 or 36 nucleotides. An even more preferred oligonucleotide consists of 2'-O-methyl phosphorothioate RNA and comprises base sequence SEQ ID NO: 191 and has a length from 30-36 nucleotides, more preferably 30, 31, 32, 33, 34, 35 or 36 nucleotides. Most preferred oligonucleotide consists of 2'-O-methyl phosphorothioate RNA, has its base sequence that consists of base sequence SEQ ID NO: 191 and has a length of 30 nucleotides.

A preferred oligonucleotide comprising or consisting of 2'-O-methyl phosphorothioate RNA comprises base sequence SEQ ID NO: 192 and has a length from 35-36 nucleotides, more preferably 35 or 36 nucleotides. An even more preferred oligonucleotide consists of 2'-O-methyl phosphorothioate RNA and comprises base sequence SEQ ID NO: 192 and has a length from 35-36 nucleotides, more preferably 35 or 36 nucleotides. Most preferred oligonucleotide consists of 2'-O-methyl phosphorothioate RNA, has its base sequence that consists of base sequence SEQ ID NO: 192 and has a length of 35 nucleotides.

In another embodiment, an oligonucleotide comprising or consisting of 2'-O-methyl phosphorothioate RNA and comprising a 5-methylcytosine and/or a abasic monomer, and/or a inosine, is represented by a nucleotide sequence comprising or consisting of a sequence that binds (or is able to bind), hybridizes (or is able to hybridize), targets and/or is reverse complementary to a $(GGGGCC)_n$ repeat present in a C9ORF72 human transcript and is particularly useful for the treatment, delay, amelioration and/or prevention of the human genetic disorder amylotrophic lateral sclerosis (ALS) or frontotemporal dementia (FTD). Preferably, this gene is from human origin.

In a preferred embodiment, an oligonucleotide defined as being reverse complementary to, binding (or being able to bind), hybridizing (or being able to hybridize) or targeting a $(GGGGCC)_n$ repeat comprises or consists of a repetitive nucleotide unit $(GGXUXX)_m$, $(GGXQXX)_m$, $(GGXIXX)_m$, or $(GGCCUC)_m$, and has a length comprised from 17 to 36 nucleotides and wherein each X is C or 5-methylcytosine such that at least one X is 5-methylcytosine, wherein each Q is an abasic monomer, wherein each I is an inosine, and wherein m is an integer. In the context of this embodiment, m may be 3, 4, 5, 6, 7. A preferred value for m is 3 or 4.

More preferably, said oligonucleotide comprises or consists of a repetitive nucleotide unit SEQ ID NO: 216-219 as defined in table 1. Even more preferred oligonucleotides sequences comprising or consisting of a repetitive nucleotide unit $(GGXUXX)_m$, (GGXQXX), (GGXIXX), or $(GGCCUC)_m$, have been identified in table 2 as SEQ ID NO:209-215.

A preferred oligonucleotide comprising or consisting of 2'-O-methyl phosphorothioate RNA comprises one of base sequences SEQ ID NO: 209 or 211 and has a length from 17-36 nucleotides, more preferably 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 209 or 211 and has a length from 17-36 nucleotides, more preferably 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 209 or 211 and has a length of 17 or 18 nucleotides.

A preferred oligonucleotide comprising or consisting of 2'-O-methyl phosphorothioate RNA comprises base sequence SEQ ID NO: 210 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 210 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 210 and has a length of 18 nucleotides.

A preferred oligonucleotide comprising or consisting of 2'-O-methyl phosphorothioate RNA comprises one of base sequences SEQ ID NO: 212 or 215 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 212 or 215 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 212 or 215 and has a length of 24 nucleotides.

A preferred oligonucleotide comprising or consisting of 2'-O-methyl phosphorothioate RNA comprises base sequence SEQ ID NO: 213 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 213 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequences SEQ ID NO: 213 and has a length of 24 nucleotides.

A preferred oligonucleotide comprising or consisting of 2'-O-methyl phosphorothioate RNA comprises base sequence SEQ ID NO: 214 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 214 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequences SEQ ID NO: 214 and has a length of 24 nucleotides.

In an embodiment, an oligonucleotide preferably comprises or consists of 2'-O-methyl phosphorothioate RNA, comprises a 5-methylcytosine and/or a 5-methyluracil and/or a 2,6-diaminopurine base, is represented by a nucleotide sequence comprising or consisting of at least 12 to 36 consecutive nucleotides, said oligonucleotide targeting, hybridizing (or is able to hybridize), binding (or is able to bind) and/or being reverse complementary to a repeat as earlier defined herein More preferably, said nucleotide sequence comprising or consisting of at least 12 to 36 nucleotides, even more preferably 15 to 24, and most preferably 20 or 21 nucleotides. The length of said oligonucleotide may be 12, 13, 14, 15, 16, 17, 18, 19, 20, 21, 22, 23, 24, 25, 26, 27, 28, 29, 30, 31, 32, 33, 34, 35, or 36 nucleotides. Said oligonucleotide may be reverse complementary to and/or capable of hybridizing to and/or capable of targeting and/or capable of binding to a repeat in a coding region of a transcript, preferably a polyglutamine $(CAG)_n$ coding tract. Said oligonucleotide may also be reverse complementary to and/or capable of hybridizing to and/or capable of targeting and/or capable of binding to a non-coding region for instance 5' or 3' untranslated regions, or intronic sequences present in precursor RNA molecules.

In the context of the invention, the expression "capable of" may be replaced with "is able to".

In a second aspect, the present invention relates to an oligonucleotide, which comprises one or more abasic sites, as defined further below, at one or both termini. Preferably 1 to 10, more preferably 2, 3, 4, 5, 6, 7, 8, 9 or 10 and most preferably 4 abasic sites are present at a single terminus or at both termini of the oligonucleotide. One or more abasic sites may be present and both free termini of the oligonucleotide (5' and 3'), or at only one. The oligonucleotide according to this aspect of the invention preferably is represented by a nucleotide or a base sequence comprising or consisting of a sequence that binds (or is able to bind), hybridizes (or is able to hybridize), targets and/or is reverse complementary to a repetitive element in a RNA transcript selected from the $(CAG)_n$, $(GCG)_n$, $(CGG)_n$, $(GAA)_n$, $(GCC)_n$, $(CCG)_n$, $(AUUCU)_n$, $(GGGGCC)_n$ or $(CCUG)_n$, as indicated above. Said oligonucleotide is preferably a single stranded oligonucleotide, and may further optionally comprise any of the modifications as discussed herein, such as one or more base modifications, sugar modifications and/or backbone modifications, such as 5-methyl-C, 5-methyl-U, 2,6-diaminopurine, 2'-O-methyl, phosphorothioate, and combinations thereof. It is to be understood that in this aspect of the invention, these modification are not compulsory.

The oligonucleotide according to this aspect of the invention, comprising one or more abasic sites at one or both termini has an improved parameter over the oligonucleotides without such abasic sites. In this context, parameters may include: binding affinity and/or kinetics, silencing activity, allelic selectivity, biostability, (intra-tissue) distribution, cellular uptake and/or trafficking, and/or immunogenicity of said oligonucleotide, as explained earlier herein in connection with the improved parameter of an oligonucleotide of the invention of the first aspect. Each of the assays and definitions provided herein in connection with the improvement of a parameter of an oligonucleotide of the first aspect also hold for an oligonucleotide of the second aspect.

Below, an oligonucleotide comprising or consisting of 2'-O-methyl phosphorothioate RNA, comprising a 5-methylcytosine and/or a 5-methyluracil base and being represented by a nucleotide or a base sequence comprising $(CUG)_m$ and thus binding to (or being able to bind to), hybridizing (or being able to hybridize), targeting and/or being reverse complementary to $(CAG)_n$ is taken as an example to further illustrate the invention. Similar parameters defined in the context of such oligonucleotide could be defined by the skilled person for other oligonucleotides falling under the scope of the invention and binding to (or being able to bind to), hybridizing (or being able to hydridize), targeting and/or being reverse complementary to other repeats as identified herein. Other or similar symptoms may be identified by the skilled person concerning other diseases as identified herein.

In a preferred embodiment, in the context of the invention, an oligonucleotide as designed herein is able to delay and/or cure and/or treat and/or prevent and/or ameliorate a human genetic disorder as Huntington's disease (HD), spinocerebellar ataxia (SCA) type 1, 2, 3, 6, 7, 12 or 17, amyotrophic lateral sclerosis (ALS), frontotemporal dementia (FTD), X-linked spinal and bulbar muscular atrophy (SBMA) and/or dentatorubropallidoluysian atrophy (DRPLA) caused by CAG repeat expansions in the transcripts of a HTT (SEQ ID NO: 80), ATXN1 (SEQ ID NO: 81), ATXN2 (SEQ ID NO: 82) ATXN3 (SEQ ID NO: 83), CACNA1A (SEQ ID NO: 84), ATXN7 (SEQ ID NO: 85), PPP2R2B (SEQ ID NO: 86), TBP (SEQ ID NO: 87), AR (SEQ ID NO: 88), ATN1 (SEQ ID NO: 89) genes when this oligonucleotide is able to reduce or decrease the amount of (toxic) transcript of a diseased allele of a HTT, ATXN1, ATXN2 ATXN3, CACNA1A, ATXN7, PPP2R2B, TBP, AR or ATN1 gene in a cell of a patient, in a tissue of a patient and/or in a patient. In an embodiment, said HTT, ATXN1, ATXN2 ATXN3, CACNA1A, ATXN7, PPP2R2B, TBP, AR or ATN1 genes are human genes.

In the case of HD, an expanded CAG repeat region is present in exon 1 of the HTT gene in the genome of a patient. An expanded CAG repeat region may be defined herein as comprising a consecutive repetition of 38 to 180 repetitive units comprising a CAG trinucleotide, in a transcribed sequence of the HTT gene In the case of SCA1, an expanded CAG repeat region is present in exon 8 of the ATXN1 gene in the genome of a patient. An expanded CAG repeat region may be defined herein as comprising a consecutive repetition of 41 to 83 repetitive units comprising a CAG trinucleotide, in a transcribed sequence of the ATXN1 gene.

In the case of SCA2, an expanded CAG repeat region is present in exon 1 of the ATXN2 gene in the genome of a patient. An expanded CAG repeat region may be defined herein as comprising a consecutive repetition of 32 to 200 repetitive units comprising a CAG trinucleotide in a transcribed sequence of the ATXN2 gene.

In the case of SCA3, an expanded CAG repeat region is present in exon 8 of the ATXN3 gene in the genome of a patient. An expanded CAG repeat region may be defined herein as comprising a consecutive repetition of 52 to 86 repetitive units comprising a CAG trinucleotide in a transcribed sequence of the ATXN3 gene.

In the case of SCA6, an expanded CAG repeat region is present in exon 47 of the CACNA1A gene in the genome of a patient. An expanded CAG repeat region may be defined herein as comprising a consecutive repetition of 20 to 33 repetitive units comprising a CAG trinucleotide in a transcribed sequence of the CACNA1A gene.

In the case of SCAT, an expanded CAG repeat region is present in exon 3 of the ATXN7 gene in the genome of a patient. An expanded CAG repeat region may be defined herein as comprising a consecutive repetition of 36 to at least 460 repetitive units comprising a CAG trinucleotide in a transcribed sequence of the ATXN7 gene.

In the case of SCA12, an expanded CAG repeat region may be present in the 5' untranslated region (UTR), in an intron or within an open reading frame of the PPP2R2B gene in the genome of a patient. An expanded CAG repeat region may be defined herein as comprising a consecutive repetition of 66 to 78 repetitive units comprising a CAG trinucleotide in a transcribed sequence of the PPP2R2B gene.

In the case of SCA17, an expanded CAG repeat region is present in exon 3 of the TBP gene in the genome of a patient. An expanded CAG repeat region may be defined herein as comprising a consecutive repetition of 45 to 66 repetitive units comprising a CAG trinucleotide in a transcribed sequence of the TBP gene.

In the case of ALS or FTD, an expanded CAG repeat region is present in exon 1 of the ATXN2 gene in the genome of a patient. An expanded CAG repeat region may be defined herein as comprising a consecutive repetition of 27 to 33 repetitive units comprising a CAG trinucleotide in a transcribed sequence of the ATXN2 gene.

In the case of ALS or FTD, an expanded GGGGCC repeat region is present in the first intron of the C9ORF72 gene in the genome of a patient. An expanded GGGGCC repeat region may be defined herein as comprising a consecutive repetition of >30 repetitive units comprising a GGGGCC hexanucleotide in a transcribed sequence of the C9ORF72 gene.

In the case of SBMA, an expanded CAG repeat region is present in exon 1 of the AR gene in the genome of a patient. An expanded CAG repeat region may be defined herein as comprising a consecutive repetition of 40 repetitive units comprising a CAG trinucleotide in a transcribed sequence of the AR gene.

In the case of DRPLA, an expanded CAG repeat region is present in exon 5 of the ATN1 gene in the genome of a patient. An expanded CAG repeat region may be defined herein as comprising a consecutive repetition of 49 to 88 repetitive units comprising a CAG trinucleotide in a transcribed sequence of the ATN1 gene.

Throughout the invention, the term CAG repeat may be replaced by $(CAG)_n$, and vice versa, wherein n is an integer that may be 6 to 29 when the repeat is present in exon 1 of the HTT transcript of a healthy individual, 6 to 39 when the repeat is present in exon 8 of the ATXN1 gene of a healthy individual, less than 31 when the repeat is present in exon 1 of the ATXN2 gene of a healthy individual, 12 to 40 when the repeat is present in exon 8 of the ATXN3 gene of a healthy individual, less than 18 when the repeat is present in exon 47 of the CACNA1A gene of a healthy individual, 4 to 17 when the repeat is present in exon 3 of the ATXN7 gene of a healthy individual, 7 to 28 when the repeat is present in the 5'UTR of the PPP2R2B gene of a healthy individual, 25 to 42 when the repeat is present in exon 3 of the TBP gene of a healthy individual, 13 to 31 when the repeat is present in exon 1 of the AR gene of a healthy individual, 12 to 40 when the repeat is present in exon 8 of the ATXN3 gene of a healthy individual, or 6 to 35 when the repeat is present in exon 5 of the ATN1 gene of a healthy individual.

It preferably means that an oligonucleotide of the invention reduces a detectable amount of disease-associated or disease-causing or mutant transcript containing an extending or unstable number of CAG repeats in a cell of said patient, in a tissue of said patient and/or in a patient. Alternatively or in combination with previous sentence, said oligonucleotide may reduce the translation of said mutant transcript and thus the amount of mutant (toxic) protein. The reduction or decrease of the amount of expanded CAG repeat transcripts may be at least 1%, 5%, 10%, 15%, 20%, 25%, 30%, 35%, 40%, 45%, 50%, 55%, 60%, 65%, 70%, 75%, 80%, 85%, 90%, 95%, 100% by comparison to the amount of expanded CAG repeat transcripts before the treatment. Another parameter may be the decrease in $(CAG)_n$ transcript or of the quantity of said mutant transcript. This may be of at least. 1%, 5%, 10%, 15%, 20%, 25%, 30%, 35%, 40%, 45%, 50%, 55%, 60%, 65%, 70%, 75%, 80%, 85%, 90%, 95%, 100% by comparison to the quantity of said transcript detected at the onset of the treatment The reduction or decrease may be assessed by Northern Blotting or Q-RT-PCR, preferably as carried out in the experimental part. An oligonucleotide of the invention may first be tested in the cellular system as described in Example 1 in the experimental part.

Alternatively or in combination with previous preferred embodiment, in the context of the invention, an oligonucleotide as designed herein is able to delay and/or cure and/or treat and/or prevent and/or ameliorate a human genetic disorder as Huntington's disease (HD), spinocerebellar ataxia (SCA) type 1, 2, 3, 6, 7, 12 or 17, amyotrophic lateral sclerosis (ALS), frontotemporal dementia (FTD), X-linked spinal and bulbar muscular atrophy (SBMA) and/or dentatorubropallidoluysian atrophy (DRPLA) caused by CAG repeat expansions in the transcripts of the HTT, ATXN1, ATXN2 ATXN3, CACNA1A, ATXN7, PPP2R2B, TBP, AR or ATN1 genes when this oligonucleotide is able to alleviate one or more symptom(s) and/or characteristic(s) and/or to improve a parameter linked with or associated with Huntington's disease (HD), spinocerebellar ataxia (SCA) type 1, 2, 3, 6, 7, 12 or 17, amyotrophic lateral sclerosis (ALS), frontotemporal dementia (FTD), X-linked spinal and bulbar muscular atrophy (SBMA) and/or dentatorubropallidoluysian atrophy (DRPLA) in an individual. An oligonucleotide as defined herein is able to improve one parameter or reduce a symptom or characteristic if after at least one week, one month, six month, one year or more of treatment using a dose of said oligonucleotide of the invention as identified herein said parameter is said to have been improved or said symptom or characteristic is said to have been reduced.

Improvement in this context may mean that said parameter had been significantly changed towards a value of said parameter for a healthy person and/or towards a value of said parameter that corresponds to the value of said parameter in the same individual at the onset of the treatment.

Reduction or alleviation in this context may mean that said symptom or characteristic had been significantly changed towards the absence of said symptom or characteristic which is characteristic for a healthy person and/or towards a change of said symptom or characteristic that corresponds to the state of the same individual at the onset of the treatment.

In this context, symptoms for Huntington's Disease are choreiform movements, progressive dementia and psychiatric manifestations (depression, psychosis, etc.). Choreiform movements consist of involuntary, rapid, irregular, jerky motor actions including facial twitching or writhing and twitching of distal extremities, and later more generalized forms that may impair gait (Ropper and Brown, 2005). Each of these symptoms may be assessed by the physician using known and described methods. A preferred method is monitoring of total functional capacity (TFC), a validated scale or symptom progression regarding the three main symptomatic areas of HD, measured by validated rating scales. These areas are specifically progression of motor signs, progression of neuropsychiatric symptoms and progression of cognitive decline. Another preferred scale therefore is the Unified HD Rating Scale (UHDRS; Huntington Study Group (Kieburtz K. et al. 1996; 11:136-142).

Huntington's disease (HD), spinocerebellar ataxia (SCA) type 1, 2, 3, 6, 7, or 17, X-linked spinal and bulbar muscular atrophy (SBMA) and dentatorubropallidoluysian atrophy (DRPLA) are all caused by CAG triplet repeat expansions in the coding region of the gene. Although the disease causing proteins in these diseases are different, in each case the resulting expanded stretch of glutamines results in a toxic-gain-of function of the protein and this leads to neurodegeneration. Protein aggregates are found in the nucleus and cytoplasm of cells, indicating that protein misfolding is a common feature of these disorders. A common preferred parameter is therefore (mutant) protein levels which can be determined by western blot analysis (Evers et al.), or the presence of protein aggregates in the nucleus and/or cytoplasm which can be monitored by in situ hybridization. An improvement of a HD parameter may be the decrease in the detection of the quantity or amount of protein aggregate. Such decrease may be at least 1%, 5%, 10%, 15%, 20%, 25%, 30%, 35%, 40%, 45%, 50%, 55%, 60%, 65%, 70%, 75%, 80%, 85%, 90%, 95%, 100% by comparison to the quantity or amount of protein aggregate before the onset of the treatment.

In the context of HD, various other proteins have been found to co-localize with htt aggregates, i.e. TATA box binding protein (TBP), CREB binding protein (CBP) and several molecular chaperones (Huang et al.; Muchowski et al.; Roon-Mom et al.; Steffan et al.). Also many affected cellular processes have been identified in HD, such as transcriptional de-regulation, mitochondrial dysfunction, and impaired vesicle transport, which may provide alternative parameters for HD (Bauer et al., 2009; Ross et al.). An improvement of each of these possible alternative HD parameters (i.e. TATA box binding protein (TBP), CREB binding protein (CBP) and several molecular chaperones) may be defined as for the improvement of protein aggregate as defined above.

Composition

In a second aspect, there is provided a composition comprising an oligonucleotide as described in the previous section entitled "Oligonucleotide". This composition preferably comprises or consists of or essentially consists of an oligonucleotide as described above.

As explained in the first aspect of the invention for ALS and FTD, it is known that at least two distinct repeats in at least two distinct transcripts may be involved in, responsible for, or linked with the disease. All preferred features relating to each of these oligonucleotides have been disclosed in the section entitled "oligonucleotide".

In a preferred embodiment, said composition is for use as a medicament. Said composition is therefore a pharmaceutical composition. A pharmaceutical composition usually comprises a pharmaceutically accepted carrier, diluent and/or excipient. In a preferred embodiment, a composition of the current invention comprises a compound as defined herein and optionally further comprises a pharmaceutically acceptable formulation, filler, preservative, solubilizer, carrier, diluent, excipient, salt, adjuvant and/or solvent. Such pharmaceutically acceptable carrier, filler, preservative, solubilizer, diluent, salt, adjuvant, solvent and/or excipient may for instance be found in Remington: The Science and Practice of Pharmacy, 20th Edition. Baltimore, Md.: Lippincott Williams & Wilkins, 2000. The compound as described in the invention possesses at least one ionizable group. An ionizable group may be a base or acid, and may be charged or neutral. An ionizable group may be present as ion pair with an appropriate counterion that carries opposite charge(s). Examples of cationic counterions are sodium, potassium, cesium, Tris, lithium, calcium, magnesium, trialkylammonium, triethylammonium, and tetraalkylammonium. Examples of anionic counterions are chloride, bromide, iodide, lactate, mesylate, acetate, trifluoroacetate, dichloroacetate, and citrate. Examples of counterions have been described [e.g. Kumar L. et al, 2008, which is incorporated here in its entirety by reference].

A pharmaceutical composition may be further formulated to further aid in enhancing the stability, solubility, absorption, bioavailability, pharmacokinetics and cellular uptake of said compound, in particular formulations comprising excipients capable of forming complexes, nanoparticles, microparticles, nanotubes, nanogels, hydrogels, poloxamers or pluronics, polymersomes, colloids, microbubbles, vesicles, micelles, lipoplexes, and/or liposomes. Examples of nanoparticles include polymeric nanoparticles, gold nanoparticles, magnetic nanoparticles, silica nanoparticles, lipid nanoparticles, sugar particles, protein nanoparticles and peptide nanoparticles.

A preferred composition comprises at least one excipient that may further aid in enhancing the targeting and/or delivery of said composition and/or said oligonucleotide to and/or into muscle and/or brain tissue and/or to a neuronal tissue and/or a cell. A cell may be a muscular or a neuronal cell.

Many of these excipients are known in the art (e.g. see Bruno, 2011) and may be categorized as a first type of excipient. Examples of first type of excipients include polymers (e.g. polyethyleneimine (PEI), polypropyleneimine (PPI), dextran derivatives, butylcyanoacrylate (PBCA), hexylcyanoacrylate (PHCA), poly(lactic-co-glycolic acid) (PLGA), polyamines (e.g. spermine, spermidine, putrescine, cadaverine), chitosan, poly(amido amines) (PAMAM), poly (ester amine), polyvinyl ether, polyvinyl pyrrolidone (PVP), polyethylene glycol (PEG) cyclodextrins, hyaluronic acid, colominic acid, and derivatives thereof), dendrimers (e.g. poly(amidoamine)), lipids {e.g. 1,2-dioleoyl-3-dimethylammonium propane (DODAP), dioleoyldimethylammonium chloride (DODAC), phosphatidylcholine derivatives [e.g. 1,2-distearoyl-sn-glycero-3-phosphocholine (DSPC)], lysophosphatidylcholine derivaties [e.g. 1-stearoyl-2-lyso-sn-glycero-3-phosphocholine (S-LysoPC)], sphingomyeline, 2-{3-[bis-(3-amino-propyl)-amino]-propylamino}-N-ditetracedyl carbamoyl methylacetamide (RPR209120), phosphoglycerol derivatives [e.g. 1,2-dipalmitoyl-sn-glycero-3-phosphoglycerol sodium salt (DPPG-Na), phosphaticid acid derivatives [1,2-distearoyl-sn-glycero-3-phosphaticid acid, sodium salt (DSPA), phosphatidylethanolamine derivatives [e.g. dioleoyl-phosphatidylethanolamine (DOPE), 1,2-distearoyl-sn-glycero-3-phosphoethanolamine (DSPE),2-diphytanoyl-sn-glycero-3-phosphoethanolamine (DPhyPE),], N-[1-(2,3-dioleoyloxy)propyl]-N,N,N-trimethylammonium (DOTAP), N-[1-(2,3-dioleyloxy)propyl]-N,N,N-trimethylammonium (DOTMA), 1,3-dioleoyloxy-2-(6-carboxy-spermyl)-propylamid (DOSPER), (1,2-dimyristyolxypropyl-3-dimethylhydroxy ethyl ammonium (DMRIE), (N1-cholesteryloxycarbonyl-3,7-diazanonane-1,9-diamine (CDAN), dimethyldioctadecylammonium bromide (DDAB), 1-palmitoyl-2-oleoyl-sn-glycerol-3-phosphocholine (POPC), (b-L-arginyl-2,3-L-diaminopropionic acid-N-palmityl-N-olelyl-amide trihydrochloride (AtuFECT01), N,N-dimethyl-3-aminopropane derivatives [e.g. 1,2-distearoyloxy-N,N-dimethyl-3-aminopropane (DSDMA), 1,2-dioleyloxy-N,N-dimethyl-3-aminopropane (DoDMA), 1,2-dilinoleyloxy-N,N-3-dimethylaminopropane (DLinDMA), 2,2-dilinoleyl-4-dimethylaminomethyl[1,3]-dioxolane (DLin-K-DMA), phosphatidylserine derivatives [1,2-dioleyl-sn-glycero-3-phospho-L-serine, sodium salt (DOPS)], cholesterol}proteins (e.g. albumin, gelatins, atellocollagen), and peptides (e.g. protamine, PepFects, NickFects, polyarginine, polylysine, CADY, MPG).

Another preferred composition may comprise at least one excipient categorized as a second type of excipient. A second type of excipient may comprise or contain a conjugate group as described herein to enhance targeting and/or delivery of the composition and/or of the oligonucleotide of the invention to a tissue and/or cell and/or into a tissue and/or cell, as for example muscle or neuronal tissue or cell. Both types of excipients may be combined together into one single composition as identified herein.

The skilled person may select, combine and/or adapt one or more of the above or other alternative excipients and delivery systems to formulate and deliver a compound for use in the present invention.

Such a pharmaceutical composition of the invention may be administered in an effective concentration at set times to an animal, preferably a mammal More preferred mammal is a human being. An oligonucleotide or a composition as defined herein for use according to the invention may be suitable for direct administration to a cell, tissue and/or an organ in vivo of individuals affected by or at risk of developing a disease or condition as identified herein, and may be administered directly in vivo, ex vivo or in vitro. Administration may be via systemic and/or parenteral routes, for example intravenous, subcutaneous, intraventricular, intrathecal, intramuscular, intranasal, enteral, intravitreal, intracerebral, epidural or oral route.

Preferably, such a pharmaceutical composition of the invention may be encapsulated in the form of an emulsion, suspension, pill, tablet, capsule or soft-gel for oral delivery, or in the form of aerosol or dry powder for delivery to the respiratory tract and lungs.

In an embodiment an oligonucleotide of the invention may be used together with another compound already known to be used for the treatment of said disease. Such other compounds may be used for slowing down progression of disease, for reducing abnormal behaviors or movements, for reducing muscle tissue inflammation, for improving muscle fiber and/or neuronal function, integrity and/or survival and/or improve, increase or restore cardiac function. Examples are, but not limited to, a steroid, preferably a (gluco)corticosteroid, an ACE inhibitor (preferably perindopril), an angiotensin II type 1 receptor blocker (preferably losartan), a tumor necrosis factor-alpha (TNFα) inhibitor, a TGFβ inhibitor (preferably decorin), human recombinant biglycan, a source of mIGF-1, a myostatin inhibitor, mannose-6-phosphate, dantrolene, halofuginone, an antioxidant, an ion channel inhibitor, a protease inhibitor, a phosphodiesterase inhibitor (preferably a PDES inhibitor, such as sildenafil or tadalafil, and/or PDE10A inhibitors and/or MP-10), L-arginine, dopamine blockers, amantadine, tetrabenazine, co-enzyme Q10, antidepressants, anti-psychotics, anti-epileptics, mood-stabilizers in general, omega-3-fatty acids, creatine monohydrate, KMO inhibitors (Kynurenine mono oxigenase) such as CHDI246, or HDAC4 inhibitors such as PBT2. Such combined use may be a sequential use: each component is administered in a distinct composition. Alternatively each compound may be used together in a single composition.

Use

In a further aspect, there is provided the use of a composition or an oligonucleotide as described in the previous sections for use as a medicament or part of therapy, or applications in which said oligonucleotide exerts its activity intracellularly.

Preferably, an oligonucleotide or composition of the invention is for use as a medicament or part of a therapy for preventing, delaying, curing, ameliorating and/or treating a human cis-element repeat instability associated genetic disorder. A human cis-element repeat instability associated genetic disorder is preferably a neuromuscular genetic disorder, more preferably as identified earlier herein.

Method

In a further aspect, there is provided a method for preventing, treating, curing, ameliorating and/or delaying a condition or disease as defined in the previous section in an individual, in a cell, tissue or organ of said individual. The method comprising administering an oligonucleotide or a composition of the invention to said individual or a subject in the need thereof.

The method according to the invention wherein an oligonucleotide or a composition as defined herein may be suitable for administration to a cell, tissue and/or an organ in vivo of individuals affected by any of the herein defined diseases or at risk of developing said disease, and may be administered in vivo, ex vivo or in vitro. An individual or a subject in need is preferably a mammal, more preferably a human being.

In a further aspect, there is provided a method for diagnosis wherein the oligonucleotide of the invention is provided with a radioactive label or fluorescent label. In this method, an oligonucleotide of the invention may be used as an in situ probe to detect foci (RNA/protein aggregates resulting from the repeat expansion) in a sample from a subject. Said sample comprises cells from said subject.

In an embodiment, in a method of the invention, a concentration of an oligonucleotide or composition is ranged from 0.01 nM to 1 μM. More preferably, the concentration used is from 0.05 to 500 nM, or from 0.1 to 500 nM, or from 0.02 to 500 nM, or from 0.05 to 500 nM, even more preferably from 1 to 200 nM.

Dose ranges of an oligonucleotide or composition according to the invention are preferably designed on the basis of rising dose studies in clinical trials (in vivo use) for which rigorous protocol requirements exist. An oligonucleotide as defined herein may be used at a dose which is ranged from 0.01 to 200 mg/kg or 0.05 to 100 mg/kg or 0.1 to 50 mg/kg or 0.1 to 20 mg/kg, preferably from 0.5 to 10 mg/kg.

Dose ranges of an oligonucleotide or composition according to the invention may also be used at a dose which is Ranged from 100 to 300 μg/week, 8 to 12 injections in total or Ranged from 150 to 250 μg/week, 9 to 11 injections in total or 200 μg/week, 11 injections in total or Ranged from 10 to 350 μg/day during two weeks or Ranged from 50 to 250 μg/day during two weeks or Ranged from 100 to 200 μg/day during two weeks or Ranged from 20 to 80 μg/day during two weeks or Ranged from 200 to 320 μg/day during two weeks or 320 μg/day, during two weeks or 30 μg/day, during two weeks.

The ranges of concentration or dose of oligonucleotide or composition as given above are preferred concentrations or doses for in vitro or ex vivo uses. The skilled person will understand that depending on the identity of the oligonucleotide used, the target cell to be treated, the gene target and its expression levels, the medium used and the transfection and incubation conditions, the concentration or dose of oligonucleotide used may further vary and may need to be optimised any further.

In this document and in its claims, the verb "to comprise" and its conjugations is used in its non-limiting sense to mean that items following the word are included, but items not specifically mentioned are not excluded. The verb "to comprise" is synonymous with the verb "to have" unless otherwise indicated. In addition the verb "to consist" may be replaced by "to consist essentially of" meaning that an oligonucleotide or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each embodiment as identified herein may be combined together unless otherwise indicated. All patent and literature references cited in the present specification are hereby incorporated by reference in their entirety.

DEFINITIONS

Throughout the application, the word "binds", "targets", "hybridizes" could be used interchangeably when used in the context of an antisense oligonucleotide which is reverse complementary to a part of a pre-mRNA as identified herein. In the context of the invention, "hybridizes" or "binds" is used under physiological conditions in a cell, preferably a human cell unless otherwise indicated.

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymine, 5-methyluracil and uracil which pair through the formation of hydrogen bonds. The natural base guanine is nucleobase complementary to the natural bases cytosine and 5-methyl-cytosine. Hybridization can occur under varying circumstances. In particular, hybridization of an oligonucleotide of the invention with a targeted pre-mRNA can occur under varying circumstances. Similarly, binding of an oligonucleotide of the invention to a targeted pre-mRNA can occur under varying circumstances. Preferably, said hybridization or said binding is assessed under physiological conditions in a cell, more preferably in a human cell. An oligonucleotide of the invention is preferably said to be able to bind to, or capable of binding to, or able to hybridize with, or capable of hybridizing with, when said binding or hybridization occurs under physiological conditions in a cell, preferably a human cell.

As used herein, "nucleotide" refers to a nucleoside further comprising a modified or unmodified phosphate linking group or a non-phosphate internucleoside linkage.

As used herein, "nucleotide analogue" or "nucleotide equivalent" refers to a nucleotide, which comprises at least one modification with respect to the nucleotides naturally occurring in RNA, such as A, C, G and U. Such a modification may be an internucleoside linkage modification and/or a sugar modification and/or a base modification.

As used herein, "monomer" refers to a precursor in the synthesis of an oligomeric or polymeric compound. Also the monomeric unit or residue within such an oligomeric or polymeric compound is encompassed in the term "monomer". Thus, "monomer" and "nucleotide residue" may be used interchangeably throughout the description. Within the context of the present invention, a monomer is preferably a nucleotide. Preferred monomers to be incorporated in the oligonucleotides according to the invention are nucleotides comprising a 2'-O-methyl substituent, a phosphorothioate internucleoside linkage and a 5-methylpyrimidine and/or a 2,6-diaminopurine nucleobase.

As used herein, "nucleobase" refers to the heterocyclic base portion of a nucleoside. Nucleobases may be naturally occurring or may be modified and therefore include, but are not limited to adenine, cytosine, guanine, uracil, thymine and analogues thereof such as 5-methyl-cytosine. In certain embodiments, a nucleobase may comprise any atom or group of atoms capable of hydrogen bonding to a base of another nucleic acid.

As used herein, "$T_m$" means melting temperature which is the temperature at which the two strands of a duplex nucleic acid separate. $T_m$ is often used as a measure of duplex stability or the binding affinity of an antisense compound toward a complementary RNA molecule.

As used herein, "2'-modified" or "2'-substituted" refers to a nucleoside comprising a pentose sugar comprising a substituent at the 2' position other than H or OH. 2'-modified nucleosides include, but are not limited to, bicyclic nucleosides wherein the bridge connecting two carbon atoms of the sugar ring connects the 2' carbon and another carbon of the sugar ring; and nucleosides with non-bridging 2'-substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(═O)—N$(R_m)(R_n)$, wherein each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, "2'-O-Me", "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, the term "adenine analogue" means a chemically-modified purine nucleobase that, when incorporated into an oligomer, is capable of forming a base pair with either a thymine or uracil of a complementary strand of RNA or DNA. Preferably, such base pair is a Watson-Crick base pair, but analogues and slight deviations thereof are also considered allowable within the context of the present invention.

As used herein, the term "uracil analogue" means a chemically-modified pyrimidine nucleobase that, when incorporated into an oligomer, is capable of forming a base pair with either a adenine of a complementary strand of RNA or DNA. Preferably, such base pair is a Watson-Crick base pair, but analogues and slight deviations thereof are also considered allowable within the context of the present invention.

As used herein, the term "thymine analogue" means a chemically-modified pyrimidine nucleobase that, when incorporated into an oligomer, is capable of forming a base pair with an adenine of a complementary strand of RNA or DNA. Preferably, such base pair is a Watson-Crick base pair, but analogues and slight deviations thereof are also considered allowable within the context of the present invention.

As used herein, the term "cytosine analogue" means a chemically-modified pyrimidine nucleobase that, when incorporated into an oligomer, is capable of forming a base pair with a guanine of a complementary strand of RNA or DNA. For example, cytosine analogue can be a 5-methylcytosine. Preferably, such base pair is a Watson-Crick base pair, but analogues and slight deviations thereof are also considered allowable within the context of the present invention.

As used herein, the term "guanine analogue" means a chemically-modified purine nucleobase that, when incorporated into an oligomer, is capable of forming a base pair with a cytosine of a complementary strand of RNA or DNA. Preferably, such base pair is a Watson-Crick base pair, but analogues and slight deviations thereof are also considered allowable within the context of the present invention.

As used herein, the term "guanosine" refers to a nucleoside or sugar-modified nucleoside comprising a guanine or guanine analog nucleobase.

As used herein, the term "uridine" refers to a nucleoside or sugar-modified nucleoside comprising a uracil or uracil analog nucleobase.

As used herein, the term "thymidine" refers to a nucleoside or sugar-modified nucleoside comprising a thymine or thymine analog nucleobase.

As used herein, the term "cytidine" refers to a nucleoside or sugar-modified nucleoside comprising a cytosine or cytosine analog nucleobase.

As used herein, the term "adenosine" refers to a nucleoside or sugar-modified nucleoside comprising an adenine or adenine analog nucleobase.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

As used herein, "internucleoside linkage" refers to a covalent linkage between adjacent nucleosides. An internucleoside linkage may be a naturally occurring internucleoside linkage, i.e. a 3' to 5' phosphodiester linkage, or a modified internucleoside linkage.

As used herein, "modified internucleoside linkage" refers to any internucleoside linkage other than a naturally occurring internucleoside linkage.

As used herein, "backbone" refers to the chain of alternating sugar moieties and internucleoside linkages, as it occurs in an oligonucleotide. The oligonucleotide of the invention comprises at least one phosphorodithioate internucleoside linkage, but it has to be understood that more backbone modifications, such as sugar modifications and/or internucleoside linkage modifications may be present in the backbone.

As used herein, "oligomeric compound" refers to a polymeric structure comprising two or more sub-structures. In certain embodiments, an oligomeric compound is an oligonucleotide. In certain embodiments, an oligomeric compound is a single-stranded oligonucleotide. In certain embodiments, an oligomeric compound is a double-stranded duplex comprising two oligonucleotides. In certain embodiments, an oligomeric compound is a single-stranded or double-stranded oligonucleotide comprising one or more conjugate groups and/or terminal groups.

As used herein, "conjugate" refers to an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to the parent compound such as an oligomeric compound. In certain embodiments, conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. In certain embodiments, conjugates are terminal groups. In certain embodiments, conjugates are attached to a 3' or 5' terminal nucleoside or to an internal nucleoside of an oligonucleotide.

As used herein, "conjugate linking group" refers to any atom or group of atoms used to attach a conjugate to an oligonucleotide or oligomeric compound. Linking groups or bifunctional linking moieties such as those known in the art are amenable to the present invention.

As used herein, "antisense compound" refers to an oligomeric compound, at least a portion of which is at least partially complementary to, or at least partially directed to, a target nucleic acid to which it hybridizes and modulates the activity, processing or expression of said target nucleic acid.

As used herein, "expression" refers to the process by which a gene ultimately results in a protein. Expression includes, but is not limited to, transcription, splicing, post-transcriptional modification, and translation.

As used herein, "antisense oligonucleotide" refers to an antisense compound that is an oligonucleotide.

As used herein, "antisense activity" refers to any detectable and/or measurable activity attributable to the hybridization of an anti sense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. In certain embodiments, antisense activity is assessed by observing a phenotypic change in a cell or animal.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is miRNA, mRNA, pre-mRNA, non-coding RNA, or natural antisense transcripts. For example, the target nucleic acid can be a cellular gene (or mRNA transcribed from the gene) whose expression is associated with a particular disorder or disease state, As used herein, "target mRNA" refers to a pre-selected RNA molecule that encodes a protein.

As used herein, "targeting" or "targeted to" refers to the association of an antisense compound to a particular target nucleic acid molecule or a particular region of nucleotides within a target nucleic acid molecule. An antisense compound targets a target nucleic acid if it is sufficiently reverse complementary to the target nucleic acid to allow hybridization under physiological conditions. In this context "sufficiently reverse complementary" may be at least 90%, 95%, 97%, 99% or 100% reverse complementary with said targeted nucleic acid molecule.

As used herein, "target site" refers to a region of a target nucleic acid that is bound by an antisense compound. In certain embodiments, a target site is at least partially within the 3' untranslated region of an RNA molecule. In certain embodiments, a target site is at least partially within the 5' untranslated region of an RNA molecule. In certain embodiments, a target site is at least partially within the coding region of an RNA molecule. In certain embodiments, a target site is at least partially within an exon of an RNA molecule. In certain embodiments, a target site is at least partially within an intron of an RNA molecule. In certain embodiments, a target site is at least partially within a miRNA target site of an RNA molecule. In certain embodiments, a target site is at least partially within a repeat region of an RNA molecule.

As used herein, "target protein" refers to a protein, the expression of which is modulated by an antisense compound. In certain embodiments, a target protein is encoded by a target nucleic acid. In certain embodiments, expression of a target protein is otherwise influenced by a target nucleic acid.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases refers to a pair of nucleobases that do not form hydrogen bonds with one another or otherwise support hybridization.

As used herein, "complementary" in reference to linked nucleosides, oligonucleotides, or nucleic acids, refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid or reverse complementarity to a target nucleic acid.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, "motif" refers to a pattern of modifications in an oligomeric compound or a region thereof. Motifs may be defined by modifications at certain nucleosides and/or at certain linking groups of an oligomeric compound.

As used herein, "the same modifications" refer to modifications relative to naturally occurring molecules that are the same as one another, including absence of modifications. Thus, for example, two unmodified DNA nucleoside have "the same modification," even though the DNA nucleoside is unmodified.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "pharmaceutically acceptable salts" refers to salts of active compounds that retain the desired biological activity of the active compound and do not impart undesired toxicological effects thereto.

As used herein, the term "independently" means that each occurrence of a repetitive variable within a claimed oligonucleotide is selected independent of one another. For example, each repetitive variable can be selected so that (i) each of the repetitive variables are the same, (ii) two or more are the same, or (iii) each of the repetitive variables can be different.

General Chemistry Definitions

As used herein, "alkyl" refers to a saturated straight or branched hydrocarbon substituent or radical, typically containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to 24 carbon atoms, more typically from 1 to 12 carbon atoms ($C_1$-$C_{12}$ alkyl) with from 1 to 6 carbon atoms ($C_1$-$C_6$ alkyl) being more preferred. The term "lower alkyl" as used herein includes from 1 to 6 carbon atoms ($C_1$-$C_6$ alkyl). Alkyl groups as used herein may optionally contain one or more further substituents.

As used herein, "alkenyl" refers to a straight or branched hydrocarbon chain radical or substituent, typically containing up to twenty four carbon atoms, and having at least one carbon-carbon double bond. Examples of alkenyl groups include, but are not limited to, ethenyl, propenyl, butenyl, 1-methyl-2-buten-1-yl, dienes such as 1,3-butadienyl and the like. Alkenyl groups typically include from 2 to 24 carbon atoms, more typically from 2 to 12 carbon atoms with from 2 to 6 carbon atoms being more preferred. Alkenyl groups as used herein may optionally contain one or more further substituents.

As used herein, "alkynyl" refers to a straight or branched hydrocarbon radical or substituent, typically containing up to twenty four carbon atoms, and having at least one carbon-carbon triple bond. Examples of alkynyl groups include, but are not limited to, ethynyl, 1-propynyl, 1-butynyl, and the like. Alkynyl groups typically include from 2 to 24 carbon atoms, more typically from 2 to 12 carbon atoms with from 2 to 6 carbon atoms being more preferred. Alkynyl groups as used herein may optionally contain one or more further substituents.

As used herein, "aminoalkyl" refers to an amino substituted alkyl radical or substituent. This term is meant to include $C_1$-$C_{12}$ alkyl groups having an amino substituent at any position and wherein the aminoalkyl group is attached to the parent molecule via its alkyl moiety. The alkyl and/or amino portions of the aminoalkyl group may optionally be further substituted with further substituents.

As used herein, "aliphatic" refers to a straight or branched hydrocarbon radical or substituent, typically containing up to twenty four carbon atoms, wherein the saturation between any two carbon atoms is a single, double or triple bond. An aliphatic group preferably contains from 1 to 24 carbon atoms, more typically from 1 to 12 carbon atoms with from 1 to 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally contain further substituents.

As used herein, "alicyclic" or "alicyclyl" refers to a cyclic radical or substituent, wherein the ring system is aliphatic. The ring system can comprise one or more rings wherein at least one ring is aliphatic. Preferred alicyclic moieties include rings having from 5 to 9 carbon atoms in the ring. Alicyclic groups as used herein may optionally contain further substituents.

As used herein, "alkoxy" refers to a radical or substituent comprising an alkyl group and an oxygen atom, wherein the alkoxy group is attached to a parent molecule via its oxygen atom. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally contain further substituents.

As used herein, "halo", "halide" and "halogen" refer to an atom, radical or substituent selected from fluorine, chlorine, bromine and iodine.

As used herein, "aryl" and "aromatic" refer to a radical or substituent comprising a mono- or polycyclic carbocyclic ring system having one or more aromatic rings. Examples of aryl groups include, but are not limited to, phenyl, naphthyl, tetrahydronaphthyl, indanyl, idenyl and the like. Preferred aryl ring systems have from 5 to 20 carbon atoms in one or more rings. Aryl groups as used herein may optionally contain further substituents.

As used herein, "aralkyl" and "arylalkyl" refer to a radical or substituent comprising an alkyl group and an aryl group, wherein the aralkyl or arylalkyl group is attached to a parent molecule via its alkyl moiety. Examples include, but are not limited to, benzyl, phenethyl and the like. Aralkyl groups as used herein may optionally contain further substituents attached to the alkyl, the aryl or both moieties that form the radical or substituent.

As used herein, "heterocyclyl" refers to a radical or substituent comprising a mono- or polycyclic ring system that includes at least one heteroatom and is unsaturated, partially saturated or fully saturated, thereby including heteroaryl groups. Heterocyclyl is also meant to include fused ring system moieties wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include[1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally contain further substituents.

As used herein, "heteroaryl" and "heteroaromatic" refer to a radical or substituent comprising a mono- or polycyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals or substituents can be attached to a parent molecule directly or through a linking moiety such as an aliphatic group or a heteroatom. Heteroaryl groups as used herein may optionally contain further substituents.

As used herein, "heteroarylalkyl" refers to a radical or substituent comprising a heteroaryl group as previously defined and an alkyl moiety, wherein the heteroarylalkyl group is attached to a parent molecule via its alkyl moiety. Examples include, but are not limited to, pyridinylmethyl, pyrimidinylethyl, napthyridinylpropyl and the like. Heteroarylalkyl groups as used herein may optionally contain further substituents on one or both of the heteroaryl or alkyl portions.

As used herein, "mono or polycyclic" refers to any ring systems, such as a single ring or a polycyclic system having rings that are fused or linked, and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and polycyclic structures can contain rings that have a uniform or varying degree of saturation, including fully saturated, partially saturated or fully unsaturated rings. Each ring can comprise ring atoms selected from C, N, O and S to give rise to heterocyclic rings as well as rings comprising only C ring atoms. Heterocyclic and all-carbon rings can be present in a mixed motif, such as for example benzimidazole wherein one ring of the fused ring system has only carbon ring atoms and the other ring has two nitrogen atoms. The mono or polycyclic structures can be further substituted with substituents such as for example phthalimide which has two oxo groups (=O) attached to one of the rings. In another aspect, mono or polycyclic structures can be attached to a parent molecule directly through a ring atom, through a substituent or a bifunctional linking moiety.

As used herein, "acyl" refers to a radical or substituent comprising a carbonyl moiety (C═O or —C(O)—) and a further substituent X, wherein the acyl group is attached to a parent molecule via its carbonyl moiety. As such, an acyl group is formally obtained by removal of a hydroxyl group from an organic acid and has the general formula —C(O)—X, wherein X is typically aliphatic, alicyclic or aromatic. The term "acyl" is also meant to include heteroacyl radicals or substituents with general formula $—Y(O)_n—X$, wherein X is as defined above and $Y(O)_n$ is typically sulfonyl, sulfinyl or phosphate. Examples of acyl groups include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally contain further substituents.

As used herein, "substituent" and "substituent group" include groups that are typically added to other substituents or parent compounds to enhance desired properties or give desired effects. Substituent groups can be protected or unprotected and can be attached to one available site or to many available sites in a parent compound. Substituent groups may also be further substituted with other substituent groups and may be attached directly or via a linking group such as an alkyl or hydrocarbyl group to a parent compound. Herein, "hydrocarbyl" refers to any group comprising C, O and H. Included are straight, branched and cyclic groups having any degree of saturation. Such hydrocarbyl groups can include one or more heteroatoms selected from N, O and S and can be further substituted with one or more substituents.

Unless otherwise indicated, the term "substituted" or "optionally substituted" refers to the (optional) presence of any of the following substituents: halogen, hydroxyl, alkyl, alkenyl, alkynyl, acyl ($—C(O)R_{aa}$), carboxyl ($—C(O)O—R_{aa}$), aliphatic groups, alicyclic groups, alkoxy, substituted oxo ($—O—R_{aa}$), aryl, aralkyl, heterocyclic, heteroaryl, heteroarylalkyl, amino ($—NR_{bb}R_{cc}$), imino ($═NR_{bb}$), amido ($—C(O)NR_{bb}R_{cc}$ or $—N(R_{bb})C(O)R_{aa}$), azido ($—N_3$), nitro ($—NO_2$), cyano (—CN), carbamido ($—OC(O)NR_{bb}R_{cc}$ or $—N(R_{bb})C(O)OR_{aa}$), ureido ($—N(R_{bb})C(O)NR_{bb}R_{cc}$), thioureido ($—N(R_{bb})C(S)NR_{bb}R_{cc}$), guanidinyl ($—N(R_{bb})C(═NR_{bb})NR_{bb}R_{cc}$), amidinyl ($—C(═NR_{bb})NR_{bb}R_{cc}$ or $—N(R_{bb})C(NR_{bb})R_{aa}$), thiol ($—SR_{bb}$), sulfinyl ($—S(O)R_{bb}$), sulfonyl ($—S(O)_2R_{bb}$), sulfonamidyl ($—S(O)_2NR_{bb}R_{cc}$ or $—N(R_{bb})S(O)_2R_{bb}$) and conjugate groups. Herein, each $R_{aa}$, $R_{bb}$ and $R_{cc}$ is, independently, H, an optionally linked chemical functional group or a further substituent, preferably but without limitation chosen from the group consisting of H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

As used herein, a zero (0) in a range indicating number of a particular unit means that the unit may be absent. For example, an oligomeric compound comprising 0-2 regions of a particular motif means that the oligomeric compound may comprise one or two such regions having the particular motif, or the oligomeric compound may not have any regions having the particular motif. In instances where an internal portion of a molecule is absent, the portions flanking the absent portion are bound directly to one another. Likewise, the term "none" as used herein, indicates that a certain feature is not present.

As used herein, "analogue" or "derivative" means either a compound or moiety similar in structure but different in respect to elemental composition from the parent compound regardless of how the compound is made. For example, an analogue or derivative compound does not need to be made from the parent compound as a chemical starting material.

The following examples are offered for illustrative purposes only, and are not intended to limit the scope of the present invention in any way.

LEGENDS TO THE FIGURE

Figure 1B:
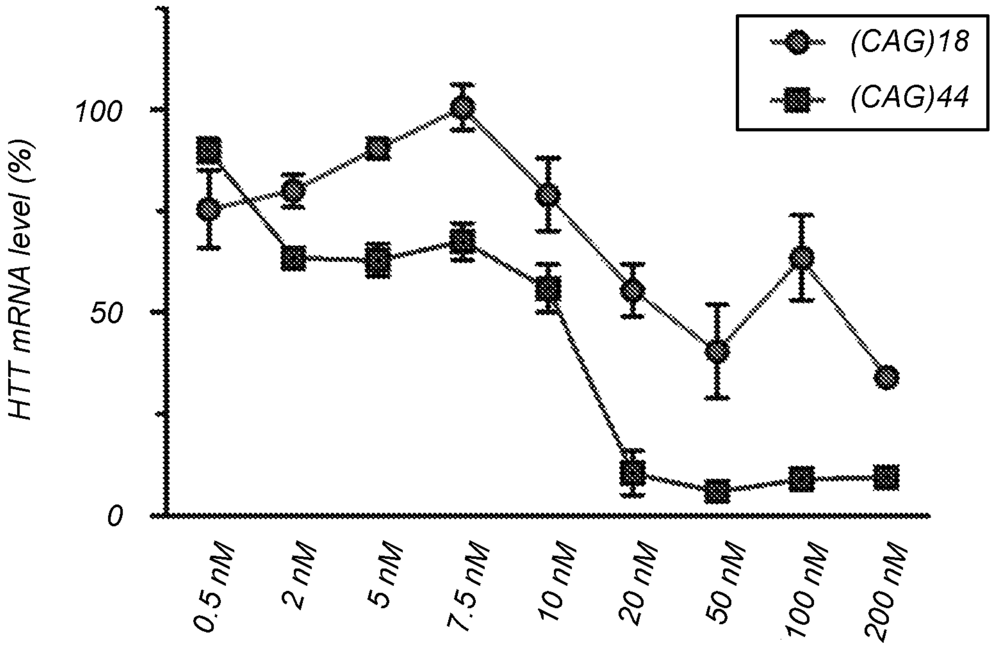
Figures 2A, 2B, 2C, 2D:
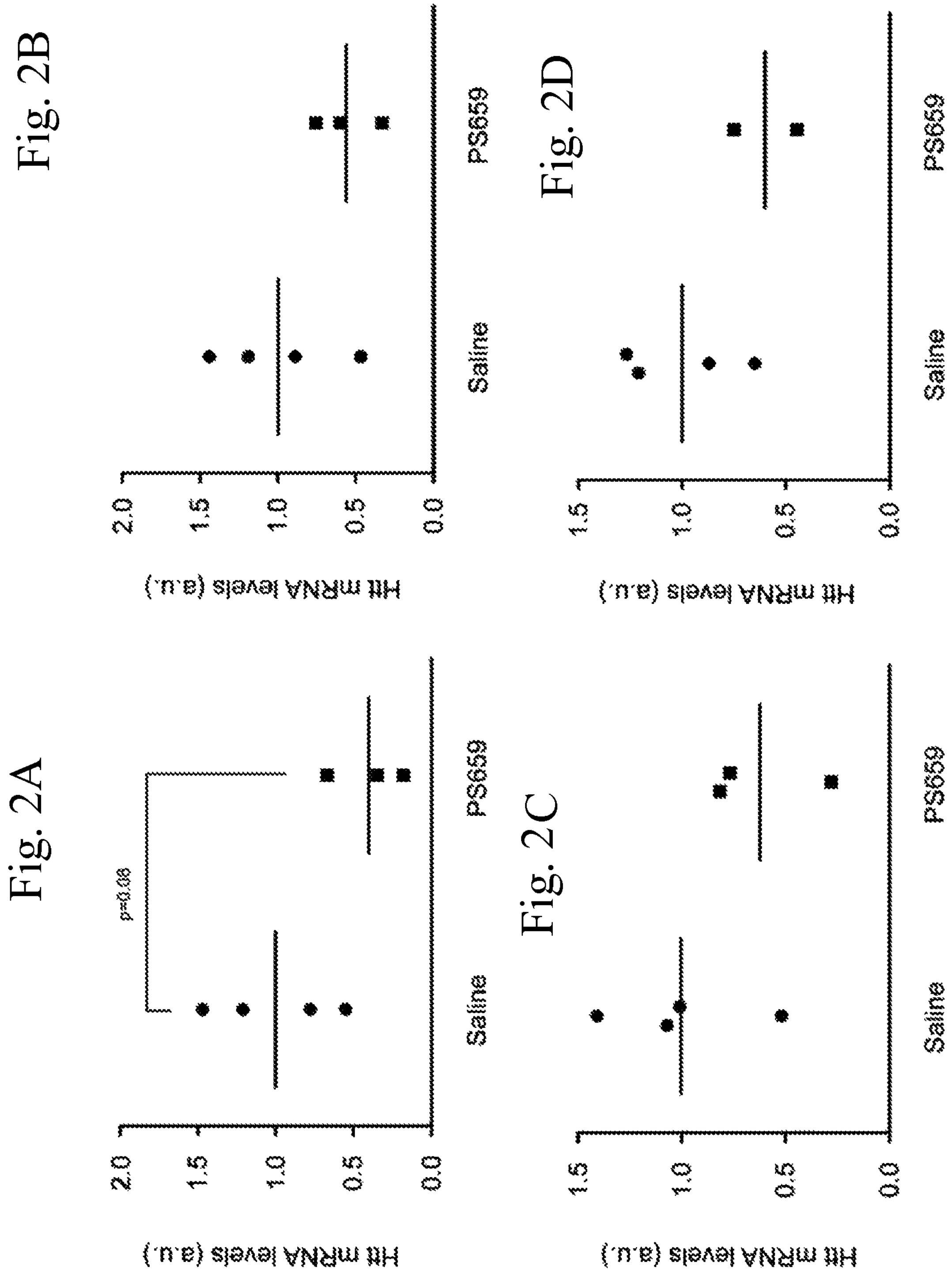

FIGS. 1A-1B. In vitro activity assay for $(XYG)_7$ in which X=5-methylcytosine and Y═U (PS659 SEQ ID NO:90; derived from SEQ ID NO:2) and $(XYG)_7$ in which X═C and Y is 5-methyluracil (PS661 SEQ ID NO: 97; derived from SEQ ID NO:3). PS659 (1A) and PS661 (1B) were transfected into HD fibroblasts (GM04022) at increasing concentrations (0.5-200 nM). Efficacy and selectivity was determined with RT-PCR and lab-on-a-chip analysis. Silencing of the expanded ($(CAG)_{44}$) and healthy ($(CAG)_{18}$) HTT transcripts were compared to the relative HTT transcript levels in mock samples. For all AONs n=2 except for mock (n=3).

FIGS. 2A-2D. In vivo efficacy of PS659 ($(XYG)_7$ in which X=5-methylcytosine and Y═U; SEQ ID NO:2) in a transgenic HD rat model. Transgenic HD rats ($(CAG)_{51}$ repeat) received 15 times an intraventricular injection with PS659 (SEQ ID NO:90 derived from SEQ ID NO: 2), during 18 weeks at a final dose of 200 μg per injection, control HD rats received vehicle only. Rats were sacrificed one week after the final injection. From all rats tissue was isolated and HTT levels were determined with Q-RT-PCR analysis. Reduced levels of HTT transcript were found in (2A) cortex, (2B) hippocampus, (2C) olfactory bulb and (2D) thalamus after PS659 treatment compared to control.

TABLE 1

General structures of AONs. X = C or 5-methylcytosine Y = U or 5-methyluracil, Z = A or 2,6-diaminopurine, I = inosine, and Q = abasic monomer.

| Target Repeat | AON Sequence (5'→3') | SEQ ID NO |
|---|---|---|
| (CAG)n | (XYG)7 (PS57)<br>X = C, Y = U | 1 |
| | (XYG)7 (PS659)<br>X = 5-methylcytosine,Y = U | 2 |

TABLE 1-continued

General structures of AONs. X = C or 5-methylcytosine Y = U or 5-methyluracil, Z = A or 2,6-diaminopurine, I = inosine, and Q = abasic monomer.

| Target Repeat | AON Sequence (5'→3') | SEQ ID NO |
|---|---|---|
| | (XYG)7 (PS661) X = C, Y = 5-methyluracil | 3 |
| | (XYG)4 | 4 |
| | (XYG)5 | 5 |
| | (XYG)6 | 6 |
| | (XYG)7 | 7 |
| | (XYG)8 | 8 |
| | (XYG)9 | 9 |
| | (XYG)10 | 10 |
| | (XYG)11 | 11 |
| | (XYG)12 | 12 |
| (GCG)n | (XGX)4 | 13 |
| | (XGX)5 | 14 |
| | (XGX)6 | 15 |
| | (XGX)7 | 16 |
| | (XGX)8 | 17 |
| | (XGX)9 | 18 |
| | (XGX)10 | 19 |
| | (XGX)11 | 20 |
| | (XGX)12 | 21 |
| (CGG)n | (XXG)4 | 22 |
| | (XXG)5 | 23 |
| | (XXG)6 | 24 |
| | (XXG)7 | 25 |
| | (XXG)8 | 26 |
| | (XXG)9 | 27 |
| | (XXG)10 | 28 |
| | (XXG)11 | 29 |
| | (XXG)12 | 30 |
| (GAA)n | (YYX)4 | 31 |
| | (YYX)5 | 32 |
| | (YYX)6 | 33 |
| | (YYX)7 | 34 |
| | (YYX)8 | 35 |
| | (YYX)9 | 36 |
| | (YYX)10 | 37 |
| | (YYX)11 | 38 |
| | (YYX)12 | 39 |
| (GCC)n | (GGX)4 | 40 |
| | (GGX)5 | 41 |
| | (GGX)6 | 42 |
| | (GGX)7 | 43 |
| | (GGX)8 | 44 |
| | (GGX)9 | 45 |
| | (GGX)10 | 46 |
| | (GGX)11 | 47 |
| | (GGX)12 | 48 |
| (CCG)n | (XGG)4 | 49 |
| | (XGG)5 | 50 |
| | (XGG)6 | 51 |
| | (XGG)7 | 52 |
| | (XGG)8 | 53 |
| | (XGG)9 | 54 |
| | (XGG)10 | 55 |
| | (XGG)11 | 56 |
| | (XGG)12 | 57 |
| (AUUCU)n | (ZGZZY)3 | 58 |
| | (ZGZZY)4 | 59 |
| | (ZGZZY)5 | 60 |
| | (ZGZZY)6 | 61 |
| | (ZGZZY)7 | 62 |
| (CCUG)n | (XZGG)3 | 63 |
| | (XZGG)4 | 64 |
| | (XZGG)5 | 65 |
| | (XZGG)6 | 66 |
| | (XZGG)7 | 67 |
| | (XZGG)8 | 68 |
| | (XZGG)9 | 69 |
| (GGGGCC)n | (GGXUXX)3 | 216 |
| | (GGXUXX)4 | 217 |
| | (GGXIXX)4 | 218 |
| | (GGXQXX)4 | 219 |

Note:
All AONs with SEQ ID NO: 4-69, or 216-219 comprise at least one base modification selected from 5-methylcytosine, 5-methyluracil, and 2,6-diaminopurine.

TABLE 2

General structures of AONs. All AONs are 2'-O-methyl phosphorothioate AONs wherein C is 5-methylcytosine, U is 5-methyluracil, A is 2,6-diaminopurine, I is inosine and Q is an abasic monomer.

| Target Repeat | AON ID | AON Sequence (5'→3') | SEQ ID NO |
|---|---|---|---|
| (CAG)n | PS659 | CUG CUG CUG CUG CUG CUG CUG | 90 |
| | | CUG CUG CUG CUG CUG CUG CUG | 91 |
| | | CUG CUG CUG CUG CUG CUG CUG | 92 |
| | | CUG CUG CUG CUG CUG CUG CUG | 93 |
| | | CUG CUG CUG CUG CUG CUG CUG | 94 |
| | | CUG CUG CUG CUG CUG CUG CUG | 95 |
| | | CUG CUG CUG CUG CUG CUG CUG | 96 |
| | PS661 | CUG CUG CUG CUG CUG CUG CUG | 97 |
| | | CUG CUG CUG CUG CUG CUG CUG | 98 |
| | | CUG CUG CUG CUG CUG CUG CUG | 99 |
| | | CUG CUG CUG CUG CUG CUG CUG | 100 |
| | | CUG CUG CUG CUG CUG CUG CUG | 101 |
| | | CUG CUG CUG CUG CUG CUG CUG | 102 |
| | | CUG CUG CUG CUG CUG CUG CUG | 103 |
| | PS660 | CUG CUG CUG CUG CUG CUG CUG | 104 |
| | | CUG CUG CUG CUG CUG CUG CUG | 105 |
| | | CUG CUG CUG CUG CUG CUG CUG | 106 |
| | PS684 | CUG CUG CUG CUG CUG CUG CUG | 107 |
| | | CUG CUG CUG CUG CUG CUG CUG QQQQ | 220 |
| | | CUG CUG CUG CUG CUG CUG CUG | 108 |
| | | CUG CUG CUG CUG CUG CUG CUG QQQQ | 221 |

TABLE 2-continued

General structures of AONs. All AONs are 2'-O-methyl phosphorothioate AONs wherein C is 5-methylcytosine, U is 5-methyluracil, A is 2,6-diaminopurine, I is inosine and Q is an abasic monomer.

| Target Repeat | AON ID | AON Sequence (5'→3') | SEQ ID NO |
|---|---|---|---|
| | | CUG CUG CUG CUG CUG CUG CUG CUG | 109 |
| | | CUG CUG CUG CUG CUG CUG CUG CUG | 110 |
| | | CUG CUG CUG CUG CUG CUG CUG CUG CUG | 111 |
| | | CUG CUG CUG CUG CUG CUG CUG CUG CUG | 112 |
| | | CUG CUG CUG CUG CUG CUG CUG CUG CUG CUG | 113 |
| | | CUG CUG CUG CUG CUG CUG CUG CUG CUG CUG | 114 |
| | | CUG CUG CUG CUG CUG CUG CUG CUG CUG CUG CUG | 115 |
| | | CUG CUG CUG CUG CUG CUG CUG CUG CUG CUG CUG | 116 |
| | | CUG CUG CUG CUG CUG CUG CUG CUG CUG CUG CUG CUG | 117 |
| | | CUG CUG CUG CUG CUG CUG CUG CUG CUG CUG CUG CUG | 118 |
| (GCG)n | | CGC CGC CGC CGC | 119 |
| | | CGC CGC CGC CGC | 120 |
| | | CGC CGC CGC CGC CGC | 121 |
| | | CGC CGC CGC CGC CGC | 122 |
| | | CGC CGC CGC CGC CGC CGC | 123 |
| | | CGC CGC CGC CGC CGC CGC | 124 |
| | | CGC CGC CGC CGC CGC CGC CGC | 125 |
| | | CGC CGC CGC CGC CGC CGC CGC | 126 |
| | | CGC CGC CGC CGC CGC CGC CGC CGC | 127 |
| | | CGC CGC CGC CGC CGC CGC CGC CGC | 128 |
| | | CGC CGC CGC CGC CGC CGC CGC CGC CGC | 129 |
| | | CGC CGC CGC CGC CGC CGC CGC CGC CGC | 130 |
| | | CGC CGC CGC CGC CGC CGC CGC CGC CGC CGC | 131 |
| | | CGC CGC CGC CGC CGC CGC CGC CGC CGC CGC | 132 |
| (CGG)n | | CCG CCG CCG CCG | 133 |
| | | CCG CCG CCG CCG | 134 |
| | | CCG CCG CCG CCG CCG | 135 |
| | | CCG CCG CCG CCG CCG | 136 |
| | | CCG CCG CCG CCG CCG CCG | 137 |
| | | CCG CCG CCG CCG CCG CCG | 138 |
| | | CCG CCG CCG CCG CCG CCG CCG | 139 |
| | | CCG CCG CCG CCG CCG CCG CCG | 140 |
| | | CCG CCG CCG CCG CCG CCG CCG CCG | 141 |
| | | CCG CCG CCG CCG CCG CCG CCG CCG | 142 |
| | | CCG CCG CCG CCG CCG CCG CCG CCG CCG | 143 |
| | | CCG CCG CCG CCG CCG CCG CCG CCG CCG | 144 |
| | | CCG CCG CCG CCG CCG CCG CCG CCG CCG CCG | 145 |
| | | CCG CCG CCG CCG CCG CCG CCG CCG CCG CCG | 146 |
| (GAA)n | | UUC UUC UUC UUC | 147 |
| | | UUC UUC UUC UUC | 148 |
| | | UUC UUC UUC UUC UUC | 149 |
| | | UUC UUC UUC UUC UUC | 150 |
| | | UUC UUC UUC UUC UUC UUC | 151 |
| | | UUC UUC UUC UUC UUC UUC | 152 |
| | | UUC UUC UUC UUC UUC UUC UUC | 153 |
| | | UUC UUC UUC UUC UUC UUC UUC | 154 |
| | | UUC UUC UUC UUC UUC UUC UUC | 155 |
| | | UUC UUC UUC UUC UUC UUC UUC | 156 |
| | | UUC UUC UUC UUC UUC UUC UUC | 157 |
| | | UUC UUC UUC UUC UUC UUC UUC UUC | 158 |
| | | UUC UUC UUC UUC UUC UUC UUC UUC | 159 |
| | | UUC UUC UUC UUC UUC UUC UUC UUC UUC | 160 |
| | | UUC UUC UUC UUC UUC UUC UUC UUC UUC | 161 |
| | | UUC UUC UUC UUC UUC UUC UUC UUC UUC UUC | 162 |
| | | UUC UUC UUC UUC UUC UUC UUC UUC UUC UUC | 163 |
| | | UUC UUC UUC UUC UUC UUC UUC UUC UUC UUC UUC | 164 |
| | | UUC UUC UUC UUC UUC UUC UUC UUC UUC UUC UUC | 165 |
| | | UUC UUC UUC UUC UUC UUC UUC UUC UUC UUC UUC UUC | 166 |
| | | UUC UUC UUC UUC UUC UUC UUC UUC UUC UUC UUC UUC | 167 |
| (GCC)n | | GGC GGC GGC GGC | 168 |
| | | GGC GGC GGC GGC GGC | 169 |
| | | GGC GGC GGC GGC GGC GGC | 170 |
| | | GGC GGC GGC GGC GGC GGC GGC | 171 |
| | | GGC GGC GGC GGC GGC GGC GGC | 172 |
| | | GGC GGC GGC GGC GGC GGC GGC | 173 |

TABLE 2-continued

General structures of AONs. All AONs are 2'-O-methyl phosphorothioate AONs wherein C is 5-methylcytosine, U is 5-methyluracil, A is 2,6-diaminopurine, I is inosine and Q is an abasic monomer.

| Target Repeat | AON ID | AON Sequence (5'→3') | SEQ ID NO |
|---|---|---|---|
| | | GGC GGC GGC GGC GGC GGC GGC | 174 |
| | | GGC GGC GGC GGC GGC GGC GGC GGC | 175 |
| | | GGC GGC GGC GGC GGC GGC GGC GGC GGC | 176 |
| | | GGC GGC GGC GGC GGC GGC GGC GGC GGC GGC | 177 |
| (CCG)n | | CGG CGG CGG CGG | 178 |
| | | CGG CGG CGG CGG CGG | 179 |
| | | CGG CGG CGG CGG CGG CGG | 180 |
| | | CGG CGG CGG CGG CGG CGG CGG | 181 |
| | | CGG CGG CGG CGG CGG CGG CGG CGG | 182 |
| | | CGG CGG CGG CGG CGG CGG CGG CGG CGG | 183 |
| | | CGG CGG CGG CGG CGG CGG CGG CGG CGG CGG | 184 |
| (AUUCU)n | | AGAAU AGAAU AGAAU | 185 |
| | | AGAAU AGAAU AGAAU AGAAU | 186 |
| | | AGAAU AGAAU AGAAU AGAAU | 187 |
| | | AGAAU AGAAU AGAAU AGAAU | 188 |
| | | AGAAU AGAAU AGAAU AGAAU | 189 |
| | | AGAAU AGAAU AGAAU AGAAU AGAAU | 190 |
| | | AGAAU AGAAU AGAAU AGAAU AGAAU AGAAU | 191 |
| | | AGAAU AGAAU AGAAU AGAAU AGAAU AGAAU AGAAU | 192 |
| (CCUG)n | | CAGG CAGG CAGG | 193 |
| | | CAGG CAGG CAGG | 194 |
| | | CAGG CAGG CAGG CAGG | 195 |
| | | CAGG CAGG CAGG CAGG | 196 |
| | | CAGG CAGG CAGG CAGG CAGG | 197 |
| | | CAGG CAGG CAGG CAGG CAGG | 198 |
| | | CAGG CAGG CAGG CAGG CAGG | 199 |
| | | CAGG CAGG CAGG CAGG CAGG | 200 |
| | | CAGG CAGG CAGG CAGG CAGG CAGG | 201 |
| | | CAGG CAGG CAGG CAGG CAGG CAGG | 202 |
| | | CAGG CAGG CAGG CAGG CAGG CAGG CAGG | 203 |
| | | CAGG CAGG CAGG CAGG CAGG CAGG CAGG | 204 |
| | | CAGG CAGG CAGG CAGG CAGG CAGG CAGG CAGG | 205 |
| | | CAGG CAGG CAGG CAGG CAGG CAGG CAGG CAGG | 206 |
| | | CAGG CAGG CAGG CAGG CAGG CAGG CAGG CAGG CAGG | 207 |
| | | CAGG CAGG CAGG CAGG CAGG CAGG CAGG CAGG CAGG | 208 |
| (GGGGCC)n | PS1252 | GGCUCC GGCUCC GGCUC | 209 |
| | | GGCQCC GGCQCC GGCQCC | 210 |
| | | GGCUCC GGCUCC GGCUCC | 211 |
| | | GGCUCC GGCUCC GGCUCC GGCUCC | 212 |
| | | GGCQCC GGCQCC GGCQCC GGCQCC | 213 |
| | | GGCICC GGCICC GGCICC GGCICC | 214 |
| | | GGCCUC GGCCUC GGCCUC GGCCUC | 215 |

EXAMPLES

Example 1

Introduction

The particular characteristics of a chosen antisense oligonucleotide (AON) chemistry may at least in part enhance binding affinity and stability, enhance activity, improve safety, and/or reduce cost of goods by reducing length or improving synthesis and/or purification procedures. This example describes the comparative analysis of the activity of AONs designed to target the expanded $(CAG)_n$ repeat in HTT transcripts in HD fibroblasts in vitro, and includes AONs with either 5-methylcytosines $(XYG)_7$, wherein X is 5-methylcytosine and Y=U being also identified as SEQ ID NO:90 (and derived from SEQ ID NO:2), or 5-methyluracils $(XYG)_7$, wherein X=C and Y=5-methyluracil being also identified as SEQ ID NO: 97 (and derived from SEQ ID NO:3).

Materials and Methods

Cell Culture.

Patient derived HD fibroblasts (GM04022) (purchased from Coriell Cell Repositories, Camden, USA) were cultured at 37° C. and 5% $CO_2$ in Minimal Essential Medium (MEM) (Gibco Invitrogen, Carlsbad, USA) with 15% heat inactivated Fetal Bovine Serum (FBS) (Clontech, Palo Alto USA), 1% Glutamax (Gibco) and 100 Um' penicillin/streptomycin (P/S) (Gibco).

Oligonucleotides.

The AONs were fully 2'-O-methyl phosphorothioate modified: PS659; $(XYG)_7$, wherein X is 5-methylcytosine and Y=U being also identified as SEQ ID NO: 90 (and derived from SEQ ID NO:2), and PS661; $(XYG)_7$, wherein X=C and Y=5-methyluracil being also identified as SEQ ID NO:97 (and derived from SEQ ID NO:3).

Transfection.

Cells were transfected with AONs complexed with PEI (2 μL per μg AON, in 0.15 M NaCl). AON-PEI complex was added in MEM medium with 5% FBS to cells to a final AON concentration varying from 0.5-200 nM. Fresh medium was supplemented after four hours and after 24 hours RNA was isolated.

RNA Isolation.

RNA from cultured cells was isolated using the *Aurum* Total RNA Mini Kit (Bio-Rad, Hercules, Calif.) according to the manufacturer's protocol.

RT-PCR and Lab-on-a-Chip Analysis.

Approximately 200 ng RNA was subjected to cDNA synthesis with random hexamers using the SuperScript first-strand synthesis system (Invitrogen) in a total volume of 20 μL. PCR was performed with primers for HTT (across the CAG repeat) and β-actin. The PCR program started with a 4 min initial denaturation at 95° C., followed by 35 cycles of 30 sec denaturation at 94° C., 30 sec annealing at 60° C., 45 sec elongation at 72° C., after which a final elongation step was performed at 72° C. for 7 min Lab-on-a-Chip was performed on the Agilent 2100 Bioanalyzer (Agilent Technologies, Waldbronn, Germany), using the Agilent DNA 1000 Kit. Expression levels were normalized for β-actin levels and relative to transcript levels without transfection. The following primers were used:

```
HTT forward;
                                    (SEQ ID NO: 70)
5'-ATGGCGACCCTGGAAAAGCTGAT-3'

HTT reverse:
                                    (SEQ ID NO: 71)
5'-TGAGGCAGCAGCGGCTG-3'

β-actin forward;
                                    (SEQ ID NO: 72)
5'-GGACTTCGAGCAAGAGATGG-3'

β-actin reverse;
                                    (SEQ ID NO: 73)
5'-AGCACTGTGTTGGCGTACAG-3'
```

Results

Both PS659 (SEQ ID NO: 90 derived from SEQ ID NO:2) and PS661 (SEQ ID NO: 97 derived from SEQ ID NO:3) were highly effective and reduced the HTT transcripts in HD fibroblasts in a dose-dependent manner (FIG. 1*a, b*). Both AONs also showed a preference for the allele with the expanded CAG repeats. PS659 (SEQ ID NO: 90 derived from SEQ ID NO:2) was more effective and more allele-specific at lower concentrations (strongest effect at 5 nM) (1*a*) than PS661 (SEQ ID NO: 97 derived from SEQ ID NO:3) (strongest effect at 20 nM) (1*b*).

Example 2

Introduction

PS659 $(XYG)_7$, wherein X is 5-methylcytosine and Y=U also identified as SEQ ID NO: 90 (derived from SEQ ID NO:2), was selected from in vitro studies as most efficient and safe candidate. This example describes its activity in a transgenic HD rat model after a series of direct intraventricular injections.

Materials and Methods

Animals.

Transgenic HD rats carry a truncated Huntington cDNA fragment with 51 CAG repeats under the control of the native rat Huntington promoter. The expressed gene product is about 75 kDa, corresponding to 22% of the full-length Huntington (cDNA position 324-2321, amino acid position 1-709/825, corresponding to exon 1-16), under the control of 886 bp of the rat Huntington promoter (von Horsten S. et al.). All animal experiments were approved by the Institutional Animal Care and Use Committees of the Maastricht University, Maastricht.

Oligonucleotides.

PS659 $(XYG)_7$, wherein X is 5-methylcytosine and Y=U also identified as SEQ ID NO: 90 (derived from SEQ ID NO:2), is a fully 2'-O-methyl phosphorothioate modified AON.

In Vivo Treatment.

Transgenic HD rats received 15 times an intraventricular injection at a final dose of 200 ng PS659 also identified as SEQ ID NO: 90 (derived from SEQ ID NO:2) during 18 weeks. Control HD rats received vehicle only. Rats were sacrificed one week after the final injection.

RNA Isolation.

RNA from brain tissue was isolated using RNA-Bee reagent (Tel Test, Inc). In brief, tissue samples were homogenized in MagNA Lyser green bead tubes (Roche) by adding RNA-Bee (50 mg tissue/mL RNA-Bee) and homogenizing using a MagNA Lyser instrument (Roche). Lysate was transferred to a new tube, chloroform (SIGMA) was added (0.2 mL per mL RNA-Bee), mixed, incubated on ice for 5 minutes and centrifuged at 13,000 rpm for 15 minutes at 4° C. The upper aqueous phase was collected and an equal volume isopropanol (SIGMA) was added, followed by a 1 hour incubation period at 4° C. and centrifugation (13,000 rpm, 15 min, 4° C.). The RNA precipitate was washed with 70% (v/v) ethanol (BioSolve), air dried and dissolved in MilliQ.

Quantitative RT-PCR Analysis.

Approximately 200 ng was subjected to cDNA synthesis with random hexamers using the SuperScript first-strand synthesis system (Invitrogen) in a total volume of 20 μL 3 μL of 1/40 cDNA dilution preparation was subsequently used in a quantitative PCR analysis according to standard procedures in presence of iQ™ SYBR® Green Supermix (Bio-Rad). Quantitative PCR primers were designed based on NCBI database sequence information. Product identity was confirmed by DNA sequencing. The signal for Rab2 and YWHAZ was used for normalization. The following primers were used:

```
Rat Htt-F;
                                    (SEQ ID NO: 74)
5'-CGCCGCCTCCTCAGCTTC-3'

Rat Htt-R;
                                    (SEQ ID NO: 75)
5'-GAGAGTTCCTTCTTTGGTCGGTGC-3'

Rab2-F;
                                    (SEQ ID NO: 76)
5'-TGGGAAACAGATAAAACTCCAGA-3'

Rab2-R;
                                    (SEQ ID NO: 77)
5'-AATATGACCTTGTGATAGAACGAAAG-3'
```

-continued

```
YWHAZ-F;
                                        (SEQ ID NO: 78)
5'-AAATGAGCTGGTGCAGAAGG-3'

YWHAZ-R;
                                        (SEQ ID NO: 79)
5'-GGCTGCCATGTCATCGTAT-3'
```

Results

PS659 (also identified as SEQ ID NO: 90 or derived from SEQ ID NO: 2) reduced transgenic Htt transcript levels in cortex (FIG. 2*a*), hippocampus (FIG. 2*b*), olfactory bulb (FIG. 2*c*) as well as in thalamus (FIG. 3*d*) when compared to saline treated rats. These results demonstrate that PS659 (also identified as SEQ ID NO: 90 or derived from SEQ ID NO; 2) is effective in vivo after direct intraventricular injection.

LIST OF REFERENCES

Aartsma-Rus et al., Hum Mol Gen 2003; 12(8):907-14.
Arai K et al. Bioorg. Med. Chem. 2011, 21, 6285
Bauer et al., 2009; J Neurochem. 110:1737-65
Braida C., et al, Human Molecular Genetics, 2010, vol 9: 1399-1412
Bruno et al., Adv Drug Deliv Rev. 2011; 63(13):1210-26
Diebold et al., 2006, Eur J Immunol; 36(12): 3256-67
Evers et al. PLoS ONE 2011, 6 (9) e24308
Huang et al., 1998 Somat Cell Molec Gen 24:217-33;
Krieg A M. et al., Nature 1995; 374: 546-549.
Krieg, A. M., Curr. Opin. Immunol. 2000; 12: 35-43.
Kumar L, Pharm. Technol. 2008, 3, 128.
Muchowski et al., 2002 PNAS 99: 727-32
Mulders et al. PNAS 2009 106(33); p 13915-20
Peacock H et al. J. Am. Chem. Soc. 2011, 133, 9200
Popovic P J. et al. J of Immunol 2006; 177: 8701-8707.
Roon-Mom et al., 2002 Mol Brain Res 109: 1-10
Ropper A H. and Brown R H., 2005 Principles of neurology. $8^{th}$ Ed. New York: McGraw-Hill, 2005.
Ross et al., 2011; Lancet Neurol. 10:83-98
Rigo, F, et al, 2012, Nature chemical biology, 8: 555-561.
Steffan et al., 2000 PNAS 97: 6763-68
von Horsten S. et al. Hum Mol Genet. 2003; 12(6):617-24
Wagner, H., Adv. Immunol. 1999; 73: 329-368.
Yu R Z., Anal Biochem 2002; 304: 19-25.

The invention claimed is:

1. A 2'-O-methyl phosphorothioate oligoribonucleotide consisting of the base sequence $(XYG)_7$, wherein each X is 5-methyl cytosine and each Y is uracil (SEQ ID NO: 2) or wherein each X is cytosine and each Y is 5-methyluracil (SEQ ID No:3).

2. An oligoribonucleotide according to claim 1, wherein said oligoribonucleotide is single stranded.

3. A composition comprising an oligoribonucleotide according to claim 1.

4. A composition according to claim 3, said composition comprising at least one excipient for enhancing the targeting and/or delivery of said composition to a tissue and/or cell and/or into a tissue and/or cell.

5. A method for treating a subject having a human cis-element repeat instability associated genetic disorder by administering an oligoribonucleotide according to claim 2 to said subject.

6. The method of claim 5, wherein said subject has the human cis-element repeat instability associated genetic disorder-Huntington Disease.

* * * * *